(12) United States Patent
Johnston

(10) Patent No.: US 12,018,250 B2
(45) Date of Patent: Jun. 25, 2024

(54) COMPOSITIONS AND METHODS FOR EVADING BACTERIAL DEFENSE MECHANISMS

(71) Applicant: Fred Hutchinson Cancer Center, Seattle, WA (US)

(72) Inventor: Christopher D. Johnston, Seattle, WA (US)

(73) Assignee: FRED HUTCHINSON CANCER CENTER, Seattle, WA (US)

(*) Notice: Subject to any disclaimer, the term of this patent is extended or adjusted under 35 U.S.C. 154(b) by 802 days.

(21) Appl. No.: 16/341,290

(22) PCT Filed: Oct. 13, 2017

(86) PCT No.: PCT/US2017/056626
§ 371 (c)(1),
(2) Date: Apr. 11, 2019

(87) PCT Pub. No.: WO2018/071841
PCT Pub. Date: Apr. 19, 2018

(65) Prior Publication Data
US 2021/0277384 A1     Sep. 9, 2021

Related U.S. Application Data

(60) Provisional application No. 62/408,693, filed on Oct. 14, 2016.

(51) Int. Cl.
| | | |
|---|---|---|
| C12Q 1/689 | (2018.01) | |
| C12N 15/10 | (2006.01) | |
| C12N 15/11 | (2006.01) | |
| C12N 15/113 | (2010.01) | |
| C12N 15/09 | (2006.01) | |
| C12N 15/64 | (2006.01) | |
| C12N 15/74 | (2006.01) | |

(52) U.S. Cl.
CPC ......... *C12N 15/1027* (2013.01); *C12N 15/10* (2013.01); *C12N 15/102* (2013.01); *C12N 15/11* (2013.01); *C12N 15/113* (2013.01); *C12Q 1/689* (2013.01); *C12N 15/09* (2013.01); *C12N 15/64* (2013.01); *C12N 15/74* (2013.01); *C12N 2310/20* (2017.05); *C12N 2310/33* (2013.01); *C12N 2310/333* (2013.01); *C12N 2330/50* (2013.01); *C12Q 2600/154* (2013.01); *C12Q 2600/156* (2013.01)

(58) Field of Classification Search
CPC ...... C12N 15/102; C12N 15/11; C12N 15/09; C12N 15/64; C12Q 1/689
See application file for complete search history.

(56) References Cited

U.S. PATENT DOCUMENTS

| | | |
|---|---|---|
| 2006/0194214 A1 | 8/2006 | Church et al. |
| 2010/0076057 A1 | 3/2010 | Sontheimer et al. |
| 2013/0216579 A1 | 8/2013 | Fidock et al. |
| 2016/0074505 A1 | 3/2016 | Kovarik et al. |
| 2016/0186147 A1 | 6/2016 | Cady et al. |

FOREIGN PATENT DOCUMENTS

WO   2015148680 A1   10/2015

OTHER PUBLICATIONS

Marraffini et al. Science. 2008. 322:1843-1845. (Year: 2008).*
Huo et al. Journal of Bacteriology. 2015. 197(11):1939-1951. (Year: 2015).*
Price et al. mSphere. 2016. 1(3):1-13. (Year: 2016).*
Kim, et al., "Improvement of Transformation Efficiency Through in vitro Methylation and SacII Site Mutation of Plasmid in Bifidobacterium longum MG1," J. Microbiol., vol. 20(6), pp. 1022-1026 (2010).
Motherway, et al, "Identification of Restriction-Modification Systems of *Bifidobacterium animalis* subsp. *lactic* CNCM I-2494 by SMRT Sequencing and Associate Methylome Analysis," PLOS One, vol. 9, Issue 4, pp. e94895, 1-10 (2014).
Oliveira, et al., The interplay of restriction-modification systems with mobile genetic elements and their prokaryotic hosts, Nucleic Acids Research, vol. 42, No. 16, pp. 10618-10631, Aug. 12, 2014.
International Search Report and Written Opinion for corresponding PCT Patent Application No. PCT/US2017/055626, dated Jan. 18, 2018 (17 pages).

* cited by examiner

*Primary Examiner* — Joseph G. Dauner
(74) *Attorney, Agent, or Firm* — Seed IP Law Group LLP

(57) ABSTRACT

The present invention features modified polynucleotide sequences that mimic host cell DNA and methods of using such sequences for the genetic engineering of bacteria that are otherwise genetically intractable.

19 Claims, 25 Drawing Sheets
Specification includes a Sequence Listing.

*T. denticola* strain ATCC 35405 (publically available data)

MTases active in the genome:

| Enzymes | DNA | Locus | Type/subtype | Length | Recognition sequence | Unique | Genuine | % Detected | Coverage |
|---|---|---|---|---|---|---|---|---|---|
| M.TdeII | - | 0227 | II alpha | 877 aa | CTCTTC | no | y | 99.3/100 | |
| M.TdeIII | - | 0909 | II alpha | 535 aa | GGNCC | no | y | 80.0/80.0 | |
| M.TdeIV | - | 0099 | III beta | 428 aa | CTAAT | yes | y | 95.7 | |
| M.TdeV | - | 0706 | II alpha | 370 aa | RAATTY | no | y | 99.9/99.9 | |

PacBio data not yet assigned to known enzymes:

| Recognition sequence | Type/subtype | Unique | Genuine | % Detected | Coverage |
|---|---|---|---|---|---|
| CAGNNNNNNTDCC | - | yes | y | 95.7/98.8 | |
| CNACNNNNNTTC | - | yes | y | 99.9/99.2 | |

FIG. 6A

*T. denticola* strain ATCC 33520

MTases active in the genome:
PacBio data not yet assigned to known enzymes:

| Recognition sequence | Type/subtype | Unique | Genuine | % Detected | Coverage |
|---|---|---|---|---|---|
| CCANNNNNNNTDCC | I | yes | y | 94.0/94.6 | 52.6 |
| CTAAT | II | no | y | 69.0 | 52.3 |
| DTAAYNNNNNTCC | II | yes | y | 89.7 | 52.2 |
| GATC | II | no | y | 97.2/97.2 | 52.5 |
| GGANNNNNRTTA | II | yes | y | 90.8 | 54.1 |
| RAATTY | II | no | y | 97.7/97.7 | 50.9 |

T. denticola strain ATCC 35405 (publically available data)

Array 1  367153-370952          ** Predicted by CRISPRDetect 2.1 **
>gi|42516522|ref|NC_002967|-Treponema denticola ATCC 35405 chromosime, complete genome.

```
36  100.0  30  ..............................  TATAGGAGGTTTCAAAATGGAAAAATCGAA
36  100.0  30  ..............................  TATCAAGTTGAGCCTTCTTTAAAGCTCCGC
36  100.0  30  ..............................  TATAGGAGTTCCAGACCCAGCACCATCACC
36  100.0  30  ..............................  AAAATCGAATGTATCGCAAGATTCAAACCA
36  100.0  30  ..............................  TACAAAATCGAAGCAGAAGAAAGGAACTTC
36  100.0  30  ..............................  GGTTCCAATCTTTTTTGGAATGATTAACAAT
36  100.0  30  ..............................  GATTCTGTATTTCAACGCGATGTTGCTAAT
36  100.0  30  ..............................  CTAACAAAAGGTGGAATTTTACCGAACAAT
36  100.0  30  ..............................  AATTAGTTGTCATTGAAGGTGAAGCCGGA
36  100.0  30  ..............................  GCGGAAAAACTATATCGTAATCTTCATAGA
36  100.0  30  ..............................  GCTGGAACGCCTATAGCGACGCAAGCTCCT
36  100.0  30  ..............................  CGCTGGAACGCCTATAGCGACGCAAGCTCC
36  100.0  30  ..............................  GGTTCCAATCTTTTTTGGAATGATTAACAAT
36  100.0  30  ..............................  CATCTAGAATCCTATAAGGCACGAAGTAAT
36  100.0  30  ..............................  CCTTTTTTGTAACTCCTATTTGCAGCTATG
36  100.0  30  ..............................  ATTACTTTTCGAAAAAAAGCCGTATTATAG
36  100.0  30  ..............................  TCTTTGTATTATAAAGTTAGCAGAGGAAAA
36  100.0  30  ..............................  GAATCTACCACCCTCAATACTCCGCCTATT
36  100.0  30  ..............................  GTCAACATCACCGCGATCACTACAAACAGC
36  100.0  30  ..............................  GAATGAAAAGGACAAGGAAAAAGCTGCCCT
36  100.0  30  ..............................  TGATTATTTGGAAGGCATGAGTAAATGCTG
36  100.0  30  ..............................  GCAGTAACTCACAAGCCACTTTGAGAGTTG
36  100.0  30  ..............................  TTCGACGCTTGTCGAAAAGGCAATCAAGGC
36  100.0  30  ..............................  CGAGAAGTTATTATTCTGAACTTCACATCG
36  100.0  30  ..............................  CTTTGGTATCAATTAGGATTTCCTAAAGTC
36  100.0  30  ..............................  TACAATGATTGCTTGTTGTTCTGATGGAAC
36  100.0  30  ..............................  TAGCCTCACCATTATAAAGCAATTCGCATG
36  100.0  30  ..............................  TGTTACGTCAAAAAATCCAATAAGTTGAAG
36  100.0  30  ..............................  CCTGATAAGGAAGATTGGCGAAAGAAGGTA
36  100.0  30  ..............................  TGCTACATCAAATAACCCTACAAGTTGAAG
36  100.0  30  ..............................  CCAAAAGTTCACAGTCATCCGAGTAGACGT
36  100.0  30  ..............................  CTATCTACTTTTGGGAACCCTAATTGGTAC
36  100.0  30  ..............................  TTTCTTCTGTTTTGTCCATGTCCAAACCTCC
36  100.0  30  ..............................  AACAATGTGTGATTTTTCGGACTTAGTCCC
36  100.0  30  ..............................  AAGGGAATAAACCTTACCATTCTGTCTTATG
36  100.0  30  ..............................  TTCCCAAAAGTTGATGCTGATACCGATTGGT
36  100.0  30  ..............................  AACAATCAGCCGTGAGGGAATACGCCGCGT
36  100.0  30  ..............................  AGGTTAATGATGAAAAAAATAATAACTACT
36  100.0  30  ..............................  GGGCATATTATGCAGATATGCAACGAAACG
36  100.0  30  ..............................  CTTGGAAAAGAATTTATAAAAATGCGAAGTT
36  100.0  30  ..............................  GAACATATGCTCGCTCTTTCTCGAGTACTC
36  100.0  30  ..............................  AAACTTTGAGGTACTAAATAAAACAAGTCA
36   97.2  30  .........................G......  ACCTTTCAATAGTAGCATCGGGCAAACCAG
36   97.2  30  ............A............G......  GTCTCTAGTTACTTTACGTATAAACTCTAT
36   94.4  30  ............A............G......  GGGCATATTATGCAGATATGCAACGAAACG
36  100.0  30  ..............................  CTTGGAAAAGAATTTATAAAAATGCGAAGTT
36  100.0  30  ..............................  ATGCGATATATCTATGACTTTACCTATTCT
36  100.0  30  ..............................  AAACTTTGAGGTACTAAATAAAACAAGTCA
36  100.0  30  ..............................  ATATCTTTTGTCGTTAAAGTTAGTAAAAAA
36  100.0  30  ..............................  TTTGAAATTCCCCAAATGTCAATTGTTTTC
36  100.0  30  ..............................  GAAAATGCAGGCGGTTCCACTGGACAGGGT
36  100.0  30  ..............................  TAATTCAAAAAAAGGTCTTGGTTTGAAAGG
36  100.0  30  ..............................  AGCCCGCCCTGCGGAATTGCACGGCCCGTT
36  100.0  30  ..............................  ATTGAGCGTCAAGCACCCGGTAAGCCCACC
36  100.0  30  ..............................  TTGGTTATCGACTTTTGATTTGAGCTATC
36  100.0  30  ..............................  CTCGCTCGAGCACAACAGGTGGCTGTCCAC
36  100.0  30  ..............................  TTTCCAGCTAGAGCATCAAAGTTTATAGGG
35   91.7   0  ..............C.A.-......        |
======  ======  ======  ==============================  ==============================
36   99.7  30  GTTTGAGAGTTGTGTAATTTAAGATGGATCTCAAAC
```

FIG. 7B
*T. denticola* strain ATCC 35405

| Repeat | %id | Spacer | Repeat_Sequence | Spacer_Sequence |
|---|---|---|---|---|
| 36 | 100.0 | 30 | ..................................... | AATCAGCAGGTAAATCAAAGATGTGCTGTA |
| 36 | 100.0 | 30 | ..................................... | GATAAAATTGTGCTTAAATTATAGCCACTC |
| 36 | 100.0 | 30 | ..................................... | ATTAAAAAAAACAGCGGAATGACTTGAACC |
| 36 | 100.0 | 30 | ..................................... | GATTTGCTGCGCGAGGCTTTGGATAAGGCT |
| 36 | 100.0 | 30 | ..................................... | AGTTGCTGCCTCGTTAAAATTTCCTTTTAC |
| 36 | 100.0 | 30 | ..................................... | AGGAGCTAATTGAACACCTTATCACTTTAC |
| 36 | 100.0 | 30 | ..................................... | CCACCGCGTAGTGGCGAACCGCGCCTATAT |
| 36 | 100.0 | 30 | ..................................... | ATTTCCGTCAAGTACTTTTCTTCATTTTCT |
| 36 | 100.0 | 30 | ..................................... | TTATTAAGTCTATCTAGAGGAGTTAATATG |
| 36 | 100.0 | 30 | ..................................... | TTTCTTCTGCTTGTCCATGTCCAAACCTCC |
| 36 | 100.0 | 30 | ..................................... | TTATCAACCTTAGGAAATCCTAACTGATAC |
| 36 | 100.0 | 30 | ..................................... | ACAAAGGCTATTACAACACAGGCCCTTCAA |
| 36 | 100.0 | 30 | ..................................... | TTAAAAAGTTACACTCTAGCGAGATATTGG |
| 36 | 100.0 | 30 | ..................................... | TGAGTTTATCGGTCCAATAAATAAGTTGG |
| 36 | 100.0 | 30 | ..................................... | GAAAGCTATACACAATCCTCTTTTGCTCAA |
| 36 | 100.0 | 30 | ..................................... | TAGGGCTTCACCCCTTAGAAACCACCTTAA |
| 36 | 100.0 | 30 | ..................................... | GTCGTAGCACCTTTGATAAGTTTGCCACCA |
| 36 | 100.0 | 30 | ..................................... | CAACTTGACATTTGTCGGAGACGATTACT |
| 36 | 100.0 | 30 | ..................................... | GCTCAATTTGAATATGAAAAGCAGCTCCAG |
| 36 | 100.0 | 30 | ..................................... | AGATAAGCGGGCGGTTATCTATGCTGGTCT |
| 36 | 100.0 | 30 | ..................................... | CTAAGGCTTTCTCTATGTCACGATACCAAA |
| 36 | 100.0 | 30 | ..................................... | CTCTTAGTTTGTAGATGTCGTTTAATATTA |
| 36 | 100.0 | 30 | ..................................... | ATCAAATCTGTCTAAAGGAGATTTTAAATG |
| 36 | 100.0 | 30 | ..................................... | TCCAAATATTGTTGCAAAATGACAGCCTGA |
| 36 | 100.0 | 30 | ..................................... | TAGGAGGTGTATACCTCTCTAAGCCTCTGT |
| 36 | 100.0 | 30 | ..................................... | AGAGAAATTATTGTTCTGGACTTCGCACTT |
| 36 | 100.0 | 30 | ..................................... | CATAGAGATTTTGACTTCTTAAATAAACAG |
| 36 | 100.0 | 30 | ..................................... | ATAAGAGTAGCGGCACCTTTAAAGCCTTTC |
| 36 | 100.0 | 30 | ..................................... | AAAAAATTCATTTTAAACCTCCATTAGCCA |
| 36 | 100.0 | 30 | ..................................... | TTACACCAAAATTCTTTTTAATAAAATCAG |
| 36 | 100.0 | 29 | ..................................... | TTGAATCTTTAATTAAGTCTAGACTTGAT |
| 36 | 100.0 | 30 | ..................................... | ACTTTACCCTGATTTTGGGTTCGGACTTTA |
| 36 | 100.0 | 30 | ..................................... | AGCAGAAAGCGGAGCGGTAGCAAGCGAAAG |
| 36 | 100.0 | 30 | ..................................... | TTTGGCGGAGCGTTAAAAAAAGCTCAACTT |
| 36 | 100.0 | 30 | ..................................... | TTGACCACGTTGCCGATAGGGAAGGGCCGT |
| 36 | 100.0 | 30 | ..................................... | TTAAATGGTGCGACTGGCTCCGAGCTTGGT |
| 36 | 100.0 | 30 | ..................................... | CTCAGATTGAGGATTATTTAAAAATAGATT |
| 36 | 100.0 | 30 | ..................................... | ACTTTCTCCATTTCAACCCGAATATCTTCA |
| 36 | 100.0 | 30 | ..................................... | TTCATCTACGCCTAAGTTAGGAAAAGAGTT |
| 36 | 100.0 | 30 | ..................................... | CCTAAGCCGGGAAAAGGGCTAAGACTGTA |
| 36 | 100.0 | 30 | ..................................... | TTTAAACTCAGCTGCAACTTCGGGAGAGGC |
| 36 | 100.0 | 30 | ..................................... | TACTAGGTCTGCTGAGTTTTATGTGGATTT |
| 36 | 100.0 | 31 | ..................................... | TCCTCCCATGTTTTGTTCTTCCGAGGTTGAG |
| 36 | 100.0 | 30 | ..................................... | CATAGAACAGATTGGCGTAGACTTGTTTAC |
| 36 | 100.0 | 30 | ..................................... | TGAAAAATTGTTATTTTGGACTTCGCATTT |
| 36 | 100.0 | 30 | ..................................... | AAGCTCTTCTTGTTGTCTTCTTACTTGTT |
| 36 | 100.0 | 30 | ..................................... | ATTAAAGCTAAGCCTTGTTATTGTTTCTTG |
| 36 | 100.0 | 30 | ..................................... | ACCAAAATTGGTGGCGAATCGCGCCTATAT |
| 36 | 100.0 | 30 | .................................G... | CGTTCTCTTTCTGAGATTTGGTCTTTAAGT |
| 34 | 91.7 | 0 | .................................G.--.... | |
| 36 | 99.8 | 30 | GTTTGAGAGTTGTGTAATTTAAGATGGATCTCAAAC | |

| Motif | modificationType | Number Detected | Number of sites in Genome | RM system Group Tag | Partner Motif |
|---|---|---|---|---|---|
| ACANNNNNRTGG | m6A | 497 | 502 | ACANNNNNRTGG/CCAYNNNNNTGT | CCAYNNNNNTGT |
| CCAYNNNNNTGT | m6A | 496 | 502 | ACANNNNNRTGG/CCAYNNNNNTGT | ACANNNNNRTGG |
| ATCNNNNNCCT | m6A | 693 | 702 | ATCNNNNNCCT/AGGNNNNNGAT | AGGNNNNNGAT |
| AGGNNNNNGAT | m6A | 693 | 702 | ATCNNNNNCCT/AGGNNNNNGAT | ATCNNNNNCCT |

MTases active in the genome:

| Enzymes | DNA | Locus | Type/subtype | Length | Recognition sequence | Unique | Genuine | % Detected |
|---|---|---|---|---|---|---|---|---|
| M.SauJE2I | chromosome | - | I gamma | 579 | CCAYNNNNNTGT | no | y | 98.8/99.0 |
| M.SauJE2II | chromosome | - | I gamma | 518 | AGGNNNNNGAT | no | y | 98.7/98.7 |

FIG. 11B

Other genes:

| Enzymes | DNA | Type/subtype | Length | Recognition sequence |
|---|---|---|---|---|
| S.SauJE2I | chromosome | I | 399 | CCAYNNNNNTGT |
| S.SauJE2II | chromosome | I | 403 | AGGNNNNNGAT |
| SauJE2ORFAP | chromosome | IV Methyl-directed | 953 | SCNGS |

CLUSTAL O(1.2.4) multiple sequence alignment

```
originalORF      atgagtattcaacatttccgtgtcgcccttattccctttttgcggcattttgccttcct
modifiedORF      atgagtattcaacatttccgtgtcgcccttattccctttttgcggcattttgccttcct
                 ************************************************************ originalORF      gttttgctcacccagaaacgctggtgaaagtaaaagatgctgaagatcagttgggtgca
modifiedORF      gttttgctcacccagaaacgctggtgaaagtaaaagatgctgaagatcagttgggtgca
                 ************************************************************ originalORF      cgagtgggttacatcgaactggatctcaacagcggtaagatccttgagagttttcgcccc
modifiedORF      cgagtgggttacatcgaactggatctcaacagcggtaagatccttgagagttttcgcccc
                 ************************************************************ originalORF      gaagagcgttttccaatgatgagcacttttaaagttctgctatgtggcgcggtattatcc
modifiedORF      gaagagcgttttccaatgatgagcacttttaaagttctgctatgtggcgcggtattatcc
                 ************************************************************ originalORF      cgtgttgacgccgggcaagagcaactcggtcgccgcatacactattctcagaatgacttg
modifiedORF      cgtgttgacgccgggcaagagcaactcggtcgccgcatacactattctcagaatgacttg
                 ************************************************************ originalORF      gttgagtactcaccagtcacagaaaagcatcttacggatggcatgacagtaagagaatta
modifiedORF      gttgagtactcaccagtcacagaaaagcatcttacggatggcatgacagtaagagaatta
                 ************************************************************ originalORF      tgcagtgctgccataaccatgagtgataacactgcggccaacttacttctgacaacgatc
modifiedORF      tgcagtgctgccataaccatgagtgataacactgcggccaacttacttctgacaacgatc
                 ************************************************************ originalORF      ggaggaccgaaggagctaaccgcttttttgcacaacatgggggatcatgtaactcgcctt
modifiedORF      ggaggaccgaaggagctaaccgcttttttgcacaacatgggggatcatgtaactcgcctt
                 ************************************************************ originalORF      gatcgttgggaaccggagctgaatgaagccataccaaacgacgagcgtgacaccacgatg
modifiedORF      gatcgttgggaaccggagctgaatgaagccataccaaacgacgagcgtgacacTacgatg
                 *************************************************  *** originalORF      cctgtagcaatggcaacaacgttgcgcaaactattaactggcgaactacttactctagct
modifiedORF      ccAgtagcaatggcaacaacgttgcgcaaactattaactggcgaactacttactctagct CLUSTAL O(1.2.4) multiple sequence alignment

```
originalORF     MSIQHFRVALIPFFAAFCLPVFAHPETLVKVKDAEDQLGARVGYIELDLNSGKILESFRP
modifiedORF     MSIQHFRVALIPFFAAFCLPVFAHPETLVKVKDAEDQLGARVGYIELDLNSGKILESFRP
                ************************************************************ originalORF     EERFPMMSTFKVLLCGAVLSRVDAGQEQLGRRIHYSQNDLVEYSPVTEKHLTDGMTVREL
modifiedORF     EERFPMMSTFKVLLCGAVLSRVDAGQEQLGRRIHYSQNDLVEYSPVTEKHLTDGMTVREL
                ************************************************************ originalORF     CSAAITMSDNTAANLLLTTIGGPKELTAFLHNMGDHVTRLDRWEPELNEAIPNDERDTTM
modifiedORF     CSAAITMSDNTAANLLLTTIGGPKELTAFLHNMGDHVTRLDRWEPELNEAIPNDERDTTM
                ************************************************************ originalORF     PVAMATTLRKLLTGELLTLASRQQLIDWMEADKVAGPLLRSALPAGWFIADKSGAGERGS
modifiedORF     PVAMATTLRKLLTGELLTLASRQQLIDWMEADKVAGPLLRSALPAGWFIADKSGAGERGS
                ************************************************************ originalORF     RGIIAALGPDGKPSRIVVIYTTGSQATMDERNRQIAEIGASLIKHW
modifiedORF     RGIIAALGPDGKPSRIVVIYTTGSQATMDERNRQIAEIGASLIKHW
                **********************************************
```

FIG. 14B

COMPOSITIONS AND METHODS FOR EVADING BACTERIAL DEFENSE MECHANISMS

CROSS-REFERENCE TO RELATED APPLICATION

This application is the U.S. national phase application, pursuant to 35 U.S.C. § 371, of PCT International Application Ser. No.: PCT/US2017/056626, filed Oct. 13, 2017, designating the United States and published in English, which claims the benefit of the following U.S. Provisional Application No. 62/408,693, filed Oct. 14, 2016, the entire contents of which are incorporated herein by reference.

STATEMENT OF RIGHTS TO INVENTIONS MADE UNDER FEDERALLY SPONSORED RESEARCH

This invention was made with government support under Grant No: R01DE022380-05 awarded by National Institutes of Health. The government has certain rights in the invention.

BACKGROUND OF THE INVENTION

The vast majority of bacteria that can be grown in a laboratory remain genetically intractable, meaning they cannot be genetically manipulated using conventional molecular biology methods. For example, research on *Clostridium difficile*, which was responsible for almost half a million infections and approximately 29,000 deaths within the United States in 2011 alone, was hindered by genetic intractability for over 20 years. The lack of genetic tractability in bacteria is a widespread and pervasive problem. Currently, the ability of scientists to understand the human microbiome is constrained by the paucity of genetically tractable members of the human microbiome.

The difficulties associated with the genetic engineering of many bacteria impede the biotechnological and commercial development of probiotic bacterial species and the use of bacteria within industrial biofuel production or industrial processes. Most importantly, however, genetic intractability, or limited tractability, makes it difficult to study many disease-causing bacteria of relevance to clinical and public health. For example, *Fusobacterium* species, which are associated with multiple clinical pathologies including periodontal disease, preterm birth, and colorectal cancer, and *Staphylococcus epidermidis*, which a common cause of hospital-associated infections (e.g., orthopedic-device infections, catheter-associated bloodstream infections, and prosthetic-valve endocarditis) are not amenable to genetic manipulation.

To facilitate the investigation of bacteria, both deadly human pathogens and industrial work horses alike, the standard model for genetic manipulation over the past 40 years has been for researchers to engage in arduous, time consuming and expensive construction of ad hoc genetic systems, one bacterial species at a time. Conventional methods of making an intractable organism accessible to genetic manipulation are expensive, time consuming, technically challenging, and do not generalize among species. Therefore, improved methods of genetically manipulating intractable organisms are urgently needed.

SUMMARY OF THE INVENTION

As described below, the present invention features modified polynucleotide sequences that mimic host cell DNA and methods of using such sequences for the genetic engineering of bacteria that are otherwise genetically intractable.

In one aspect, the invention provides a polynucleotide containing alterations at selected restriction sites or Clustered Regularly Interspaced Short Palindromic Repeat (CRISPR) system targets relative to a reference sequence, where the alterations reduce the degradation of the polynucleotide when it is transformed in a bacterial host.

In another aspect, the invention provides a method for obtaining a syngenic polynucleotide, the method including, identifying recognition sites for Restriction Modification (RM) and Clustered Regularly Interspaced Short Palindromic Repeat (CRISPR) system in a polynucleotide sequence derived from a bacteria of interest, detecting the recognition sites identified in a heterologous polynucleotide, and modifying the polynucleotide sequence of the heterologous polynucleotide to alter one or more of the recognition sites, thereby obtaining a syngenic polynucleotide that resists degradation when transformed into the bacteria of interest.

In yet another aspect, the invention provides a method for obtaining a syngenic polynucleotide, the method including identifying recognition sites for Restriction Modification and CRISPR system in a polynucleotide sequence derived from a bacteria of interest, detecting the recognition sites identified in a heterologous polynucleotide, modifying the polynucleotide sequence of the heterologous polynucleotide to alter one or more of the recognition sites, and synthesizing the modified polynucleotide molecule, thereby obtaining a syngenic polynucleotide that resists degradation when transformed into the bacteria of interest.

In various embodiments of any of the above aspects, or any other aspect of the invention delineated herein, the coding region of the polynucleotide is altered by synonymous codon substitution. In various embodiments of any of the above aspects, the noncoding region of the polynucleotide is altered by single nucleotide polymorphisms. In various embodiments of any of the above aspects, the polynucleotide is selected from the group consisting of a plasmid, replication origin, antibiotic resistance cassette, promoter, repressor, terminator, protein coding domain, transposon, operon, linear DNA knockout cassette, detectable reporter, and a bacterial genome. In various embodiments of any of the above aspects, the alterations confer resistance to restriction endonuclease degradation or Clustered Regularly Interspaced Short Palindromic Repeat (CRISPR) degradation. In various embodiments of any of the above aspects, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or 100% of the of restriction sites or Clustered Regularly Interspaced Short Palindromic Repeat (CRISPR) system targets are altered. In some embodiments, 1, 2, 3, 4, 5, 6, 7, 8, 9, 10 or more nucleotides are altered. In some embodiments, about 10, 20, 30, 40, 50, 60 70, 80, 90, 100 or more nucleotides are altered. In some embodiments the bacterial cell contains the polynucleotide, where the bacterial cell expresses a restriction endonuclease capable of degrading foreign DNA or a Clustered Regularly Interspaced Short Palindromic Repeat (CRISPR) system.

In various embodiments of any of the above aspects, or any other aspect of the invention delineated herein, the bacteria naturally occurs in the human microbiome, soil, or a marine environment. In various embodiments of any of the above aspects, or any other aspect of the invention delineated herein, the bacteria is selected from the group consisting of *Actinobacteria, Armatimonadetes, Aquificae,*

*Bacteroidetes, Chlamydiae, Chloroflexi, Caldiserica, Chlorobi, Chrysiogenetes, Cyanobacteria, Deferribacteres, Deinococcus-Thermus, Dictyoglomi, Elusimicrobia, Euryarchaeota, Firmicutes, Fusobacteria, Fibrobacteres, Gemmatimonadetes, Lentisphaerae, Nitrospirae, Planctomycetes, Proteobacteria, Spirochaetes,* SRI, *Synergistetes, Tenericutes,* TM7, *Thermodesulfobacteria, Thermomicrobia, Thermotogae,* and *Verrucomicrobia*. In various embodiments of any of the above aspects, the bacteria is a gram negative or gram positive bacteria.

In various embodiments of any of the above aspects, or any other aspect of the invention delineated herein, the gram positive bacteria is selected from the group consisting of any one or more of *Pasteurella* species, *Staphylococci* species, and *Streptococcus* species. In various embodiments of any of the above aspects, the gram negative bacteria is selected from the group consisting of any one or more of *Escherichia coli, Pseudomonas* species, and *Salmonella* species.

In various embodiments of any of the above aspects, or any other aspect of the invention delineated herein, the bacteria is an infectious bacteria. In various embodiments of any of the above aspects, the infectious bacteria is selected from the group consisting of any one or more of *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus antracis, Corynebacterium diphtherias, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia,* and *Actinomyces israelli.*

In various embodiments of any of the above aspects, or any other aspect of the invention delineated herein, the bacteria is a health promoting or probiotic bacteria. In various embodiments of any of the above aspects, the health promoting or probiotic bacteria is selected from the group consisting of any one or more of *Lactobacillus* species, *Lactococcus* species, *Bifidobacterium* species, *Saccharomyces* species, *Enterococcus* species, *Streptococcus* species, *Pediococcus* species, *Leuconostoc* species, *Bacillus* species, and *Escherichia coli* species. In various embodiments of any of the above aspects, the bacteria is *Prevotella*. In various embodiments of any of the above aspects, the bacteria is *P. Intermedia*.

In various embodiments of any of the above aspects, or any other aspect of the invention delineated herein, the syngenic polynucleotide is obtained by mutagenesis or de novo synthesis. In various embodiments of any of the above aspects, the coding region of the polynucleotide is altered by synonymous codon substitution. In various embodiments of any of the above aspects, a noncoding region of the polynucleotide is altered by single nucleotide polymorphisms.

In various embodiments of any of the above aspects, or any other aspect of the invention delineated herein, the polynucleotide is selected from the group consisting of a plasmid, replication origin, antibiotic resistance cassette, promoter, repressor, terminator, protein coding domain, transposon, operon, linear DNA knockout cassette and a bacterial genome. In various embodiments of any of the above aspects, the alterations confer resistance to restriction endonuclease degradation or Clustered Regularly Interspaced Short Palindromic Repeat (CRISPR) degradation. In various embodiments of any of the above aspects, the polynucleotide is deoxyribonucleic acid (DNA) or ribonucleic acid (RNA). In various embodiments of any of the above aspects, the polynucleotide sequence is altered relative to a reference sequence. In various embodiments of any of the above aspects, the polynucleotide sequence of the bacteria is obtained by Single Molecule Real Time (SMRT) sequencing of the bacterial genome.

In various embodiments of any of the above aspects, or any other aspect of the invention delineated herein, the syngenic polynucleotide is a replicative plasmid. In various embodiments of any of the above aspects, the syngenic polynucleotide recapitulates the preferential codon bias of the bacteria of interest. In various embodiments of any of the above aspects, the methylations are altered via synonymous codon substitution using splicing by overlap extension (SOEing). In various embodiments of any of the above aspects, the methylations are altered via an enzyme that methylates adenine residues.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "host-mimicking DNA" or "syngenic DNA" is meant a heterogenous polynucleotide molecule or fragment thereof that includes modifications relative to a reference sequence, wherein the modifications are sufficient to ensure that the polynucleotide is not degraded when introduced into a bacterial cell of interest.

By "analog" is meant a molecule that is not identical, but has analogous functional or structural features. For example, a polynucleotide analog retains the biological activity of a corresponding naturally-occurring polynucleotide, while having certain biochemical modifications that enhance the analog's function relative to a naturally occurring polynucleotide. Such biochemical modifications could increase the analog's resistance to polynucleotide degrading enzymes without altering, for example, the biological activity of the molecule.

By "alteration" is meant a change in a polynucleotide sequence as detected by standard art known methods such as those described herein. As used herein, an alteration includes a 5% change in polynucleotide sequence, 10% change in polynucleotide sequence, preferably a 25% change, more preferably a 40% change, and most preferably a 50% or greater change in polynucleotide sequence. In one embodiment, about 5%, about 10%, about 15%, about 20%, about 25%. about 30%. about 35%, about 40%, about 45%, about 50%, about 55%, about 60%, about 65%, about 70%, about 75%, about 80%, about 85%, about 90%, about 95%, about 99%, or even 100% of the Restriction Modification (RM) target sequence (i.e., restriction sites) or regularly interspaced short palindromic repeat (CRISPR) system target sites are altered.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable reporter" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "plasmid" is meant a circular polynucleotide molecule that is separate from the chromosomal DNA and can replicate independently. Furthermore, a plasmid may comprise a selectable marker to indicate the success of the transformation or other procedures meant to introduce foreign DNA into a cell and a multiple cloning site which includes multiple restriction enzyme consensus sites to enable the insertion of an insert. Plasmid vectors can be referred to as cloning or donor vectors. Such vectors are used to ease cloning and to amplify a sequence of interest. Plasmid vectors called expression or acceptor vectors are specifically for the expression of a gene of interest in a defined target cell. Those plasmid vectors generally show an expression cassette, consisting of a promoter, the transgene and a terminator sequence. Expression plasmids can be shuttle plasmids containing elements that enable their propagation and selection in different host cells.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers. A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell. By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide.

"Hybridization" refers to hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry or biochemical techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA molecule) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, "obtaining" as in "obtaining an agent" includes synthesizing, purchasing, or otherwise acquiring the agent.

By "polypeptide" is meant any chain of amino acids, regardless of length or post-translational modification.

By "positioned for expression" is meant that the polynucleotide of the invention (e.g., a DNA molecule) is positioned adjacent to a DNA sequence that directs transcription and translation of the sequence (e.g., facilitates the production of, for example, a recombinant polypeptide of the invention, or an RNA molecule).

By "promoter" is meant a polynucleotide sufficient to direct transcription. As used herein, a promoter refers to a polynucleotide that directs transcription of a segment of a polynucleotide to which it is operatively linked. The promoter can include specific sequences that are sufficient for RNA polymerase recognition, binding and transcription initiation. In addition, the promoter region includes sequences that modulate transcription initiation, such as cis acting elements which may be responsive to trans acting factors. Exemplary promoters include nucleic acid sequences of lengths 100, 250, 300, 400, 500, 750, 900, 1000, 1250, and 1500 nucleotides that are upstream (e.g., immediately upstream) of the translation start site.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. And S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those of ordinary skill in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100·mu·g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those of ordinary skill in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those of ordinary skill in the art. Hybridization techniques are well known to those of ordinary skill in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, inclusive of the first and last values in the range.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

BRIEF DESCRIPTION OF THE DRAWINGS

FIG. 6 (including FIG. 6A and FIG. 6B) shows restriction modification (RM) system targets in *T. denticola* strains, ATCC 35405 and ATCC 33520. FIG. 6A includes the sequences: cagnnnnnnnn tdcc (SEQ ID NO:7) and cnacnnnnnn ttc (SEQ ID NO:8). FIG. 6B includes ccannnnnnn ntdcc (SEQ ID NO:20); dtaaynnnnn tcc (SEQ ID NO: 21); ggannnnnrt tc (SEQ ID NO:22).

FIG. 7 (including FIG. 7A and FIG. 7B) shows CRISPR system targets in *T. denticola* strains. Sequences in FIG. 7A and FIG. 7B include: tataggaggt ttcaaaatgg aaaaatcgaa (SEQ ID NO:27); tatcaagttg agccttcttt aaagctccgc (SEQ ID NO:28); tataggagtt ccagacccag caccatcacc (SEQ ID NO:29); aaaatcgaat gtatcgcaag attcaaacca (SEQ ID NO:30); tacaaaatcg aagcagaaga aaggaacttc (SEQ ID NO:31); ggttccaatc tttttggaat gattaacaat (SEQ ID NO:32); gattctgtat ttcaacgcga tgttgctaat (SEQ ID NO:33); ctaacaaaag gtggaatttt accgaacaat (SEQ ID NO: 34); aattagttgt cattgaaggt gaagccgga (SEQ ID NO:35); gcggaaaaac tatatcgtaa tcttcataga (SEQ ID NO: 36); gctggaacgc ctatagcgac gcaagctcct (SEQ ID NO: 37); cgctggaacg cctatagcga cgcaagctcc (SEQ ID NO: 38); ggttccaatc tttttggaat gattaacaat (SEQ ID NO:39); catctagaat cctataaggc acgaagtaat (SEQ ID NO:40); ccttttttgt aactcctatt tgcagctatg (SEQ ID NO:41); attacttttc gaaaaaaagc cgtattatag (SEQ ID NO:42); tctttgtatt ataagttag cagaggaaaa (SEQ ID NO:43); gaatctacca ccctcaatac tccgcctatt (SEQ ID NO:44); gtcaacatca ccgcgatcac tacaaacagc (SEQ ID NO:45); gaatgaaaag gacaaggaaa aagctgccct (SEQ ID NO:46) tgattatttg gaaggcatga gtaaatgctg (SEQ ID NO: 47); gcagtaactc acaagccact ttgagagttg (SEQ ID NO: 48); ttcgacgctt gtcgaaaagg caatcaaggc (SEQ ID NO: 49); cgagaagtta ttattctgaa cttcacatcg (SEQ ID NO: 50); ctttggtatc aattaggatt tcctaaagtc (SEQ ID NO: 51); tacaatgatt gcttgttgtt ctgatggaac (SEQ ID NO: 52); tagcctcacc attataaagc aattcgcatg (SEQ ID NO:53); tgttacgtca aaaaatccaa taagttgaag (SEQ ID NO: 54); cctgataagg aagattggcg aaagaaggta (SEQ ID NO: 55); tgctacatca aataaccccta caagttgaag (SEQ ID NO: 56); ccaaaagttc acagtcatcc gagtagacgt (SEQ ID NO: 57); ctatctactt ttgggaaccc taattggtac (SEQ ID NO: 58); tttcttctgt ttgtccatgt ccaaacctcc (SEQ ID NO: 59); aacaatgtgt gattttttcgg acttagtccc (SEQ ID NO: 60); aagggaataa ccttaccatt ctgtcttatg (SEQ ID NO: 61); ttcccaaaag ttgatgctga tacgattggt (SEQ ID NO: 62); aacaatcagc cgtgagggaa tacgccgcgt (SEQ ID NO: 63); aggttaatga tgaaaaaaat aataactact (SEQ ID NO: 64); gggcatatta tgcagatatg caacgaaacg (SEQ ID NO: 65); cttggaaaag aattttataaa atgcgaagtt (SEQ ID NO: 66); gaacatatgc tcgctcttttc tcgagtactc (SEQ ID NO: 67); aaactttgag gtactaaata aacaagtca (SEQ ID NO:68); accttcaat agtagcatcg ggcaaaccag (SEQ ID NO:69); gtctctagtt actttacgta taaactctat (SEQ ID NO: 70); gggcatatta tgcagatatg caacgaaacg (SEQ ID NO: 71); cttggaaaag aattttataaaa atgcgaagtt (SEQ ID NO: 72); atgcgatata tctatgactt tacctattct (SEQ ID NO: 73); aaactttgag gtactaaata aaacaagtca (SEQ ID NO: 74); atatcttttg tcgttaaagt tagtaaaaaa (SEQ ID NO: 75); tttgaaattc cccaaatgtc aattgttttc (SEQ ID NO: 76); gaaaatgcag gcggttccac tggagaggtt (SEQ ID NO: 77); taattcaaaa aaaggtcttg gttt-gaaagg (SEQ ID NO: 78); agcccgccct gcggaattgc acggcccgtt (SEQ ID NO: 79); attgagcgtc aagcacccgg taagcccacc (SEQ ID NO: 80); ttggttattc gactttttgat ttgagctatc (SEQ ID NO: 81); ctcgctcgag cacaacaggt ggctgtccac (SEQ ID NO: 82); tttccagcta gagcatcaaa gtttataggg (SEQ ID NO: 83); gttt-gagagt tgtgtaattt aagatggagc aaac (SEQ ID NO: 84); aatcagcagg taaatcaaag atgtgctgta (SEQ ID NO: 85); gataaaattg tgcttaaatt atagccactc (SEQ ID NO: 86); attaaaaaaa acagcggaat gacttgaacc (SEQ ID NO:87); gatttgctgc gcgaggcttt ggataaggct (SEQ ID NO: 88); agttgctgcc tcgt-taaaat ttccttttac (SEQ ID NO: 89); aggagctaat tgaacacctt (SEQ ID NO: 90); ccaccgcgta gtggcgaacc gcgcc-tatat (SEQ ID NO: 91); atttccgtca agtacttttc ttcattttct (SEQ ID NO: 92); ttattaagtc tatctagagg agttaatatg (SEQ ID NO: 93); tttcttctgc ttgtccatgt ccaaacctcc (SEQ ID NO: 94); ttat-caacct taggaaatcc taactgatac (SEQ ID NO: 95); acaaaggcta ttacaacaca ggccctttcaa (SEQ ID NO: 96); ttaaaaagtt acactctagc gagatattgg (SEQ ID NO: 97); tgagtttat cggtc-caata aataagttgg (SEQ ID NO: 98); gaaagctata cacaatcctc ttttgctcaa (SEQ ID NO: 99); tagggcttca ccccttagaa accaccttaa (SEQ ID NO:100); gtcgtagcac ctttgataag tttgccacca (SEQ ID NO: 101); caacttgaca ttttgtcgga gacgattact (SEQ ID NO: 102); gctcaatttg aatatgaaaa gcagctccag (SEQ ID NO: 103); agataagcgg gcggttatct atgctggtct (SEQ ID NO: 104); ctaaggcttt ctctatgtca cgataccaaa (SEQ ID NO: 105); ctcttagttt gtagatgtcg tttaatatta (SEQ ID NO: 106); atcaaatctg tctaaggag attttaaatg (SEQ ID NO: 107); tccaaatatt gttgcaaaat gacagcctga (SEQ ID NO: 108); taggaggtgt atacctctct aagcctctgt (SEQ ID NO: 109); agagaaatta ttgttctgga cttcgcactt (SEQ ID NO: 110); catagagatt ttgacttctt aaataaacag (SEQ ID NO: 111); ataagagtag cggcaccttt aaagcctttc (SEQ ID NO: 112); aaaaaattca ttttaaacct ccattagcca (SEQ ID NO:113); ttacaccaaa attcttttta ataaaatcag (SEQ ID NO: 114); ttgaatcttt aattaagtct agacttgat (SEQ ID NO: 115); actttaccct gattttgggt tcggacttta (SEQ ID NO: 116); agcagaaagc ggagcggtag caagcgaaag (SEQ ID NO: 117); tttggcggag cgttaaaaaa agctcaactt (SEQ ID NO: 118); ttgaccacgt tgccgatagg gaagggccgt (SEQ ID NO: 119); ttaaatggtg cgactggctc cgagcttggt (SEQ ID NO: 120); ctcagattga ggattattta aaaatagatt (SEQ ID NO: 121); actttctcca tttcaacccg aatatcttca (SEQ ID NO: 122); ttcatctacg cctaagttag gaaaagagtt (SEQ ID NO: 123); cctaagccgg ggaaaagggc taagactgta (SEQ ID NO: 124); tttaaactca gctgcaactt cgg-gagaggc (SEQ ID NO: 125); tactaggtct gctgagtttt atgtggattt (SEQ ID NO: 126); tcctcccatg ttttgttctt ccgaggttga g (SEQ ID NO: 127); cataganacag attggcgtag acttgtttac (SEQ ID NO: 128); tgaaaaattg ttattttgga cttcgcattt (SEQ ID NO: 129); aagctcttct tgttgtcttc ttacttgttc (SEQ ID NO: 130); attaaagcta agccttgtta ttgtttcttg (SEQ ID NO: 131); accaaaattg gtggcgaatc gcgcctatat (SEQ ID NO: 132); cgttctcttt ctgagatttg gtctttaagt (SEQ ID NO: 133).

FIG. 10 shows a table of the Single Molecule Real Time (SMRT) sequencing analysis of modified bases in the genome (Basemod analysis). Sequences in FIG. 10 include: acannnnnnr tgg (SEQ ID NO: 134); ccaynnnnnn tgt (SEQ ID NO:11); atcnnnnncc t (SEQ ID NO: 135); and (SEQ ID NO: 12).

FIG. 11A and FIG. 11B provides two images of tables showing the processing of the sequence and methylome data through the Restriction Enzyme Database (REBASE). FIG. 11A shows the methyltransferase genes and corresponding methylated motifs in *S. aureus* JE2. FIG. 11B shows the restriction enzyme genes and corresponding target motifs in *S. aureus* JE2. FIG. 11A and FIG. 11B both include the sequences ccaynnnnnn tgt (SEQ ID NO:11) and aggnnnnnga t (SEQ ID NO:12).

FIG. 14A and FIG. 14B provides two images of Clustal omega alignment between the original pEPSA5 and modified pEPSA5 sequences. FIG. 14A and FIG. 14B provide a sequence identified as an "original ORF" (SEQ ID NO:136) and a sequence identified as a "modified ORF" (SEQ ID NO:137).

DETAILED DESCRIPTION OF THE INVENTION

As described below, the present invention features modified polynucleotide sequences that mimic host cell DNA and methods of using such sequences for the genetic engineering of bacteria that are otherwise genetically intractable.

Figure 1A:
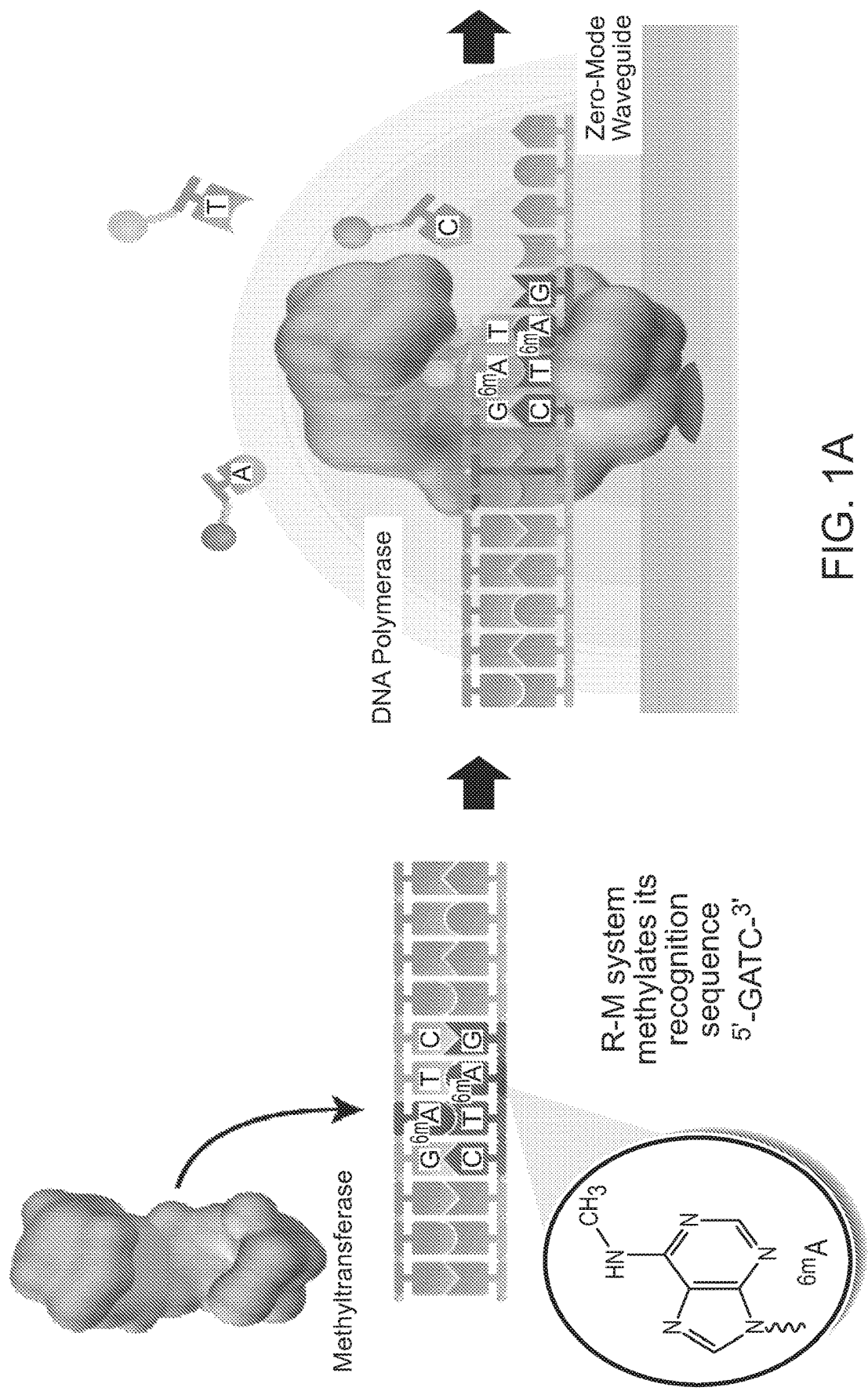
FIG. 1 (including FIG. 1A and FIG. 1B) provides a schematic showing Single Molecule Real Time (SMRT) sequencing to identify sequences associated with the Restriction Modification (RM) and clustered regularly interspaced short palindromic repeat (CRISPR) systems.
FIG. 1B provides the unmodified gDNA sequences cgagctagtt catgt (SEQ ID NO:18) and aaagaccccg ggaccttac tataccttgg tattggcatc aggtgcggat (SEQ ID NO: 19).
Figure 1B:
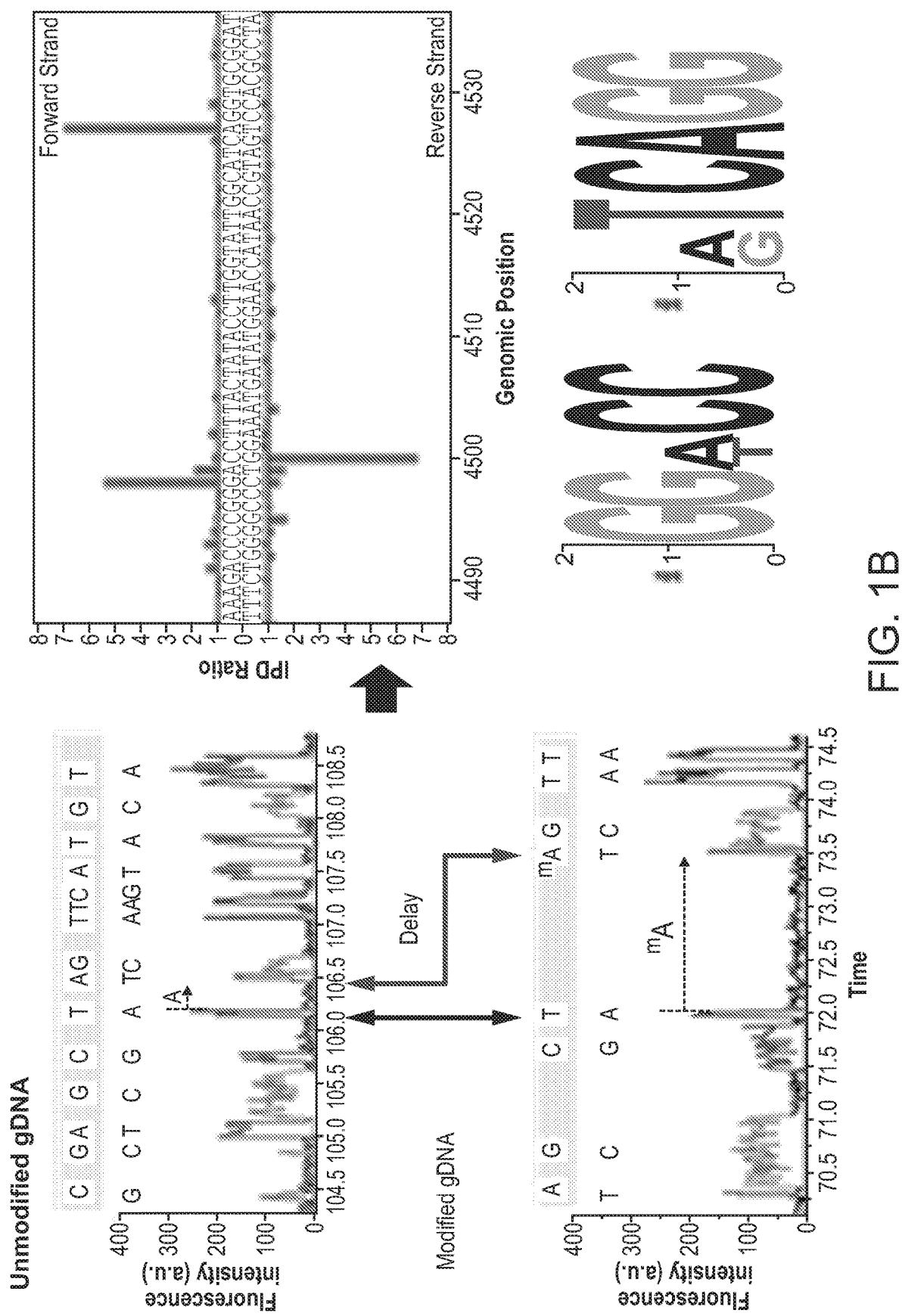

Without being bound by theory, the difficulty in transformation of genetically intractable organisms likely results from the presence of complex bacterial defense mechanisms that degrade foreign or "non-host" DNA. Bacteria utilize Restriction Modification (RM) and Clustered Regularly Interspaced Short Palindromic Repeat (CRISPR)-CAS arrays, which are systems utilized by such microorganisms as defense mechanisms to identify and degrade foreign non-host DNA. Restriction-modification (RM) systems operate through a restriction endonuclease activity that degrades the foreign DNA via a specific recognition sequence, and a modification methyltransferase activity that protects the same recognition sequence on host DNA through addition of a methyl group. CRISPR arrays are genomic DNA regions containing a succession of highly conserved repeated sequences (23-44 bp in length) separated by similarly sized "spacers" while Cas proteins are essential for interaction with the CRISPR array. During CRISPR defense, an endonuclease uses RNA molecules (crRNAs) transcribed from these spacers as targeting molecules to recognize and degrade homologous regions in foreign non-host DNA. RM and CRISPR-Cas systems typically serve as a cellular defense from invading bacteriophage, but concomitantly form an active barrier to the introduction of foreign DNA during genetic engineering. As described herein, Single Molecule Real Time (SMRT) sequencing of the *P. intermedia* genome was undertaken, which identified eleven methylated potential RM sites. To circumvent these RM systems, replicative plasmids having a reduced number of restriction sites are being constructed through a combination of mutagenesis and de novo synthesis (FIG. 1). These plasmids are expected to function and replicate in *P. intermedia*, permitting its genetic manipulation, potentially generating new technologies for the study of this emerging pathogen.

The invention provides a method of generating "host-mimicking DNA" or "syngenic DNA" for use as a genetic tool (e.g., construct, plasmid, expression vector). The method first identifies Restriction Modification (RM) and CRISPR system targets by PacBio™ Single Molecule Real-Time (SMRT) genomic DNA and epigenetic sequencing of a bacterial genome. In one embodiment, the invention provides polynucleotides comprising sequences that have been altered relative to wild type polynucleotides. The alterations confer resistance to restriction endonuclease degradation or CRISPR degradation by recoding the sequence.

Figure 2:
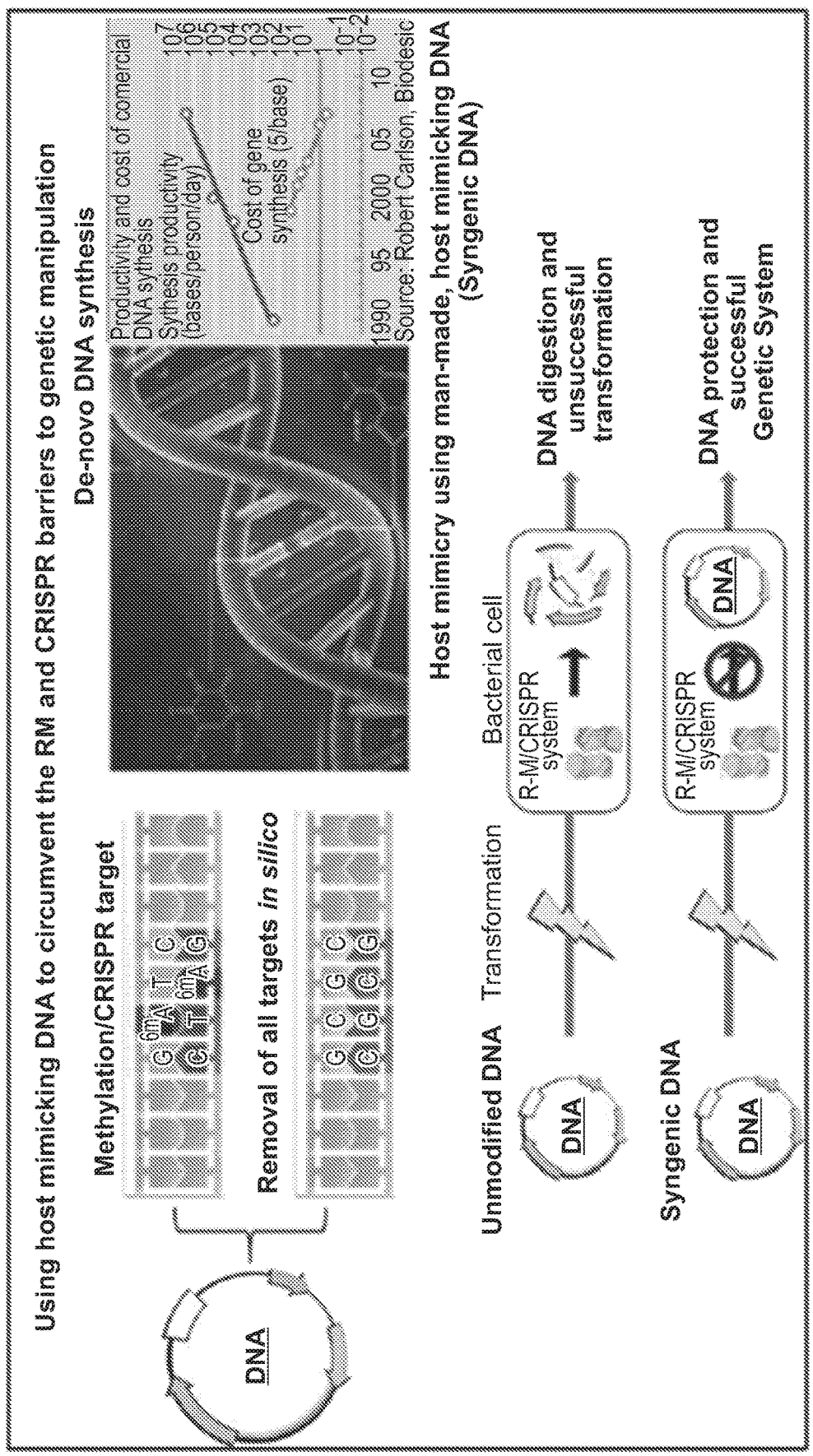
FIG. 2 provides a schematic showing an overview of the method to generate syngenic DNA.
Figure 3A:
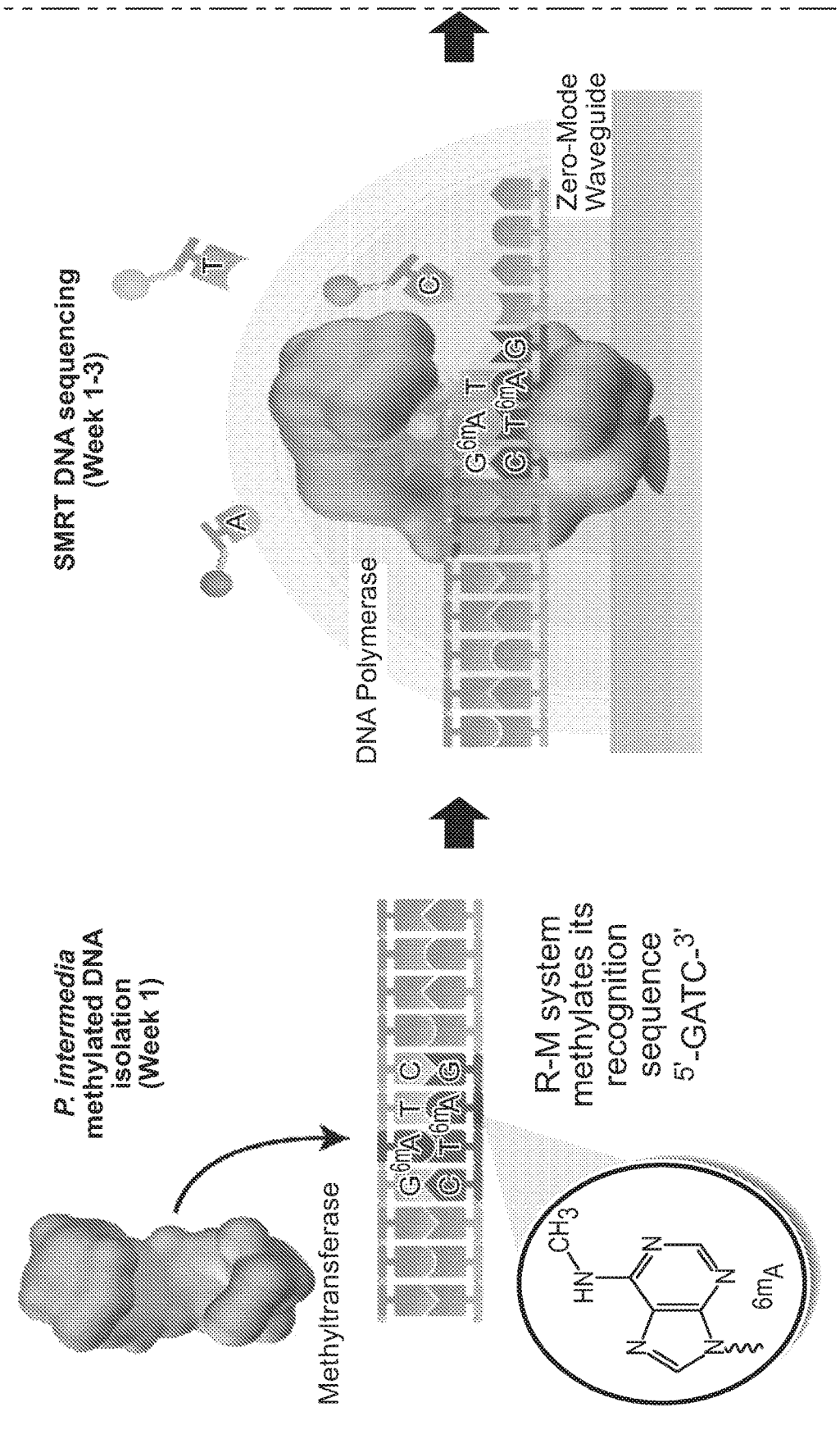
FIG. 3 (including FIG. 3A, FIG. 3B, FIG. 3C, and FIG. 3D) provides a schematic showing the process of defining the methylome of *P. intermedia* (top panel) and creating a host-mimicking strategy to create a *P. intermedia* genetic system (bottom panel).
FIG. 3B provides the unmodified gDNA sequences cgagctagtt catgt (SEQ ID NO:18) and aaagaccccg ggaccttac tataccttgg tattggcatc aggtgcggat (SEQ ID NO: 19).
Figure 3B:
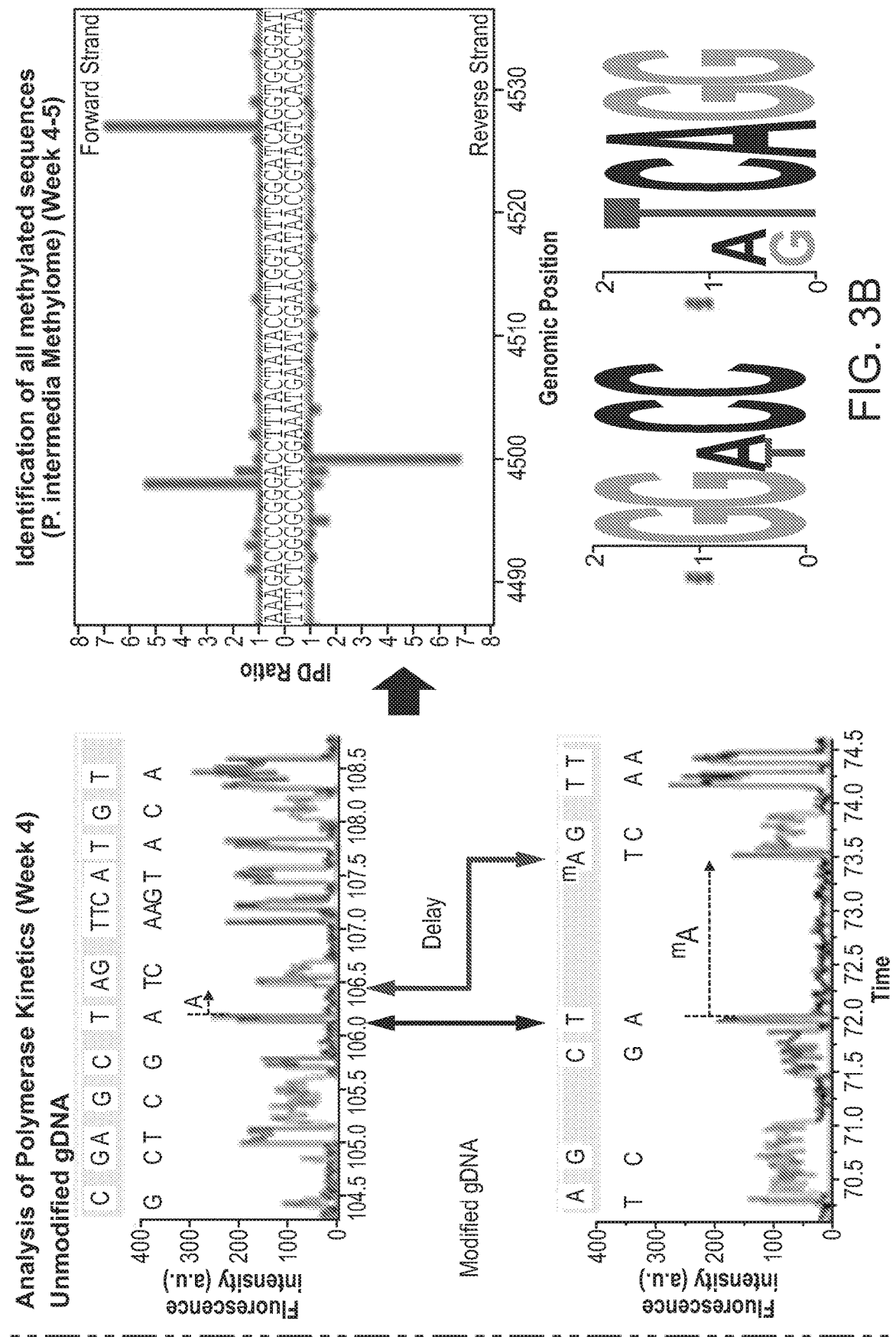
Figure 3C:
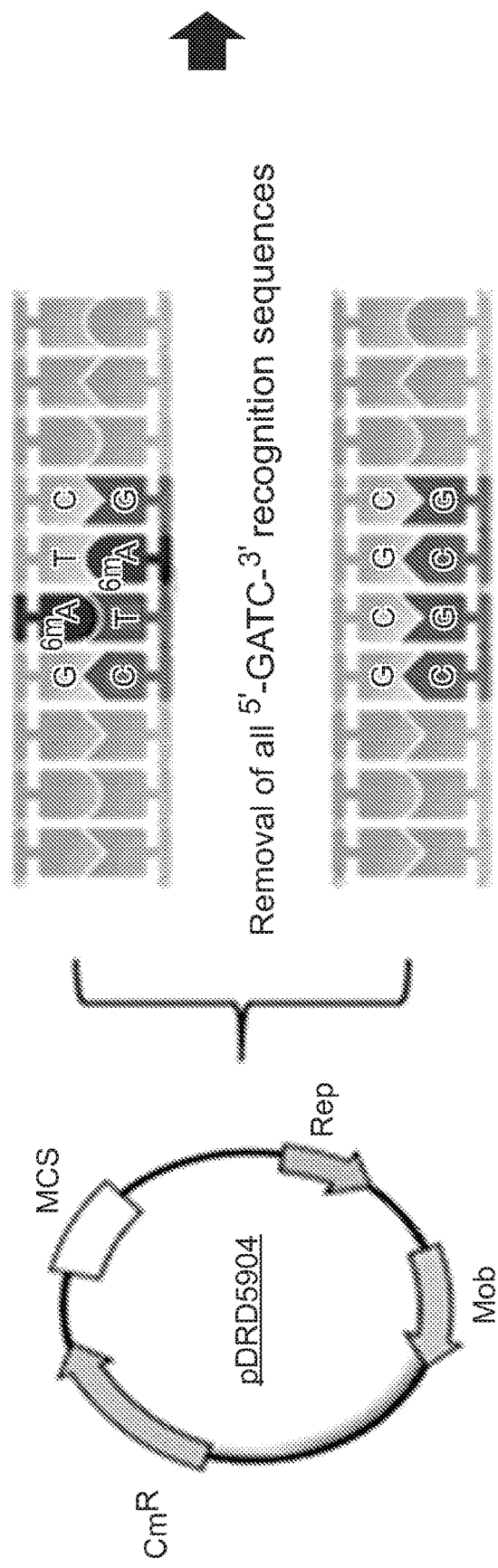
Figure 3D:
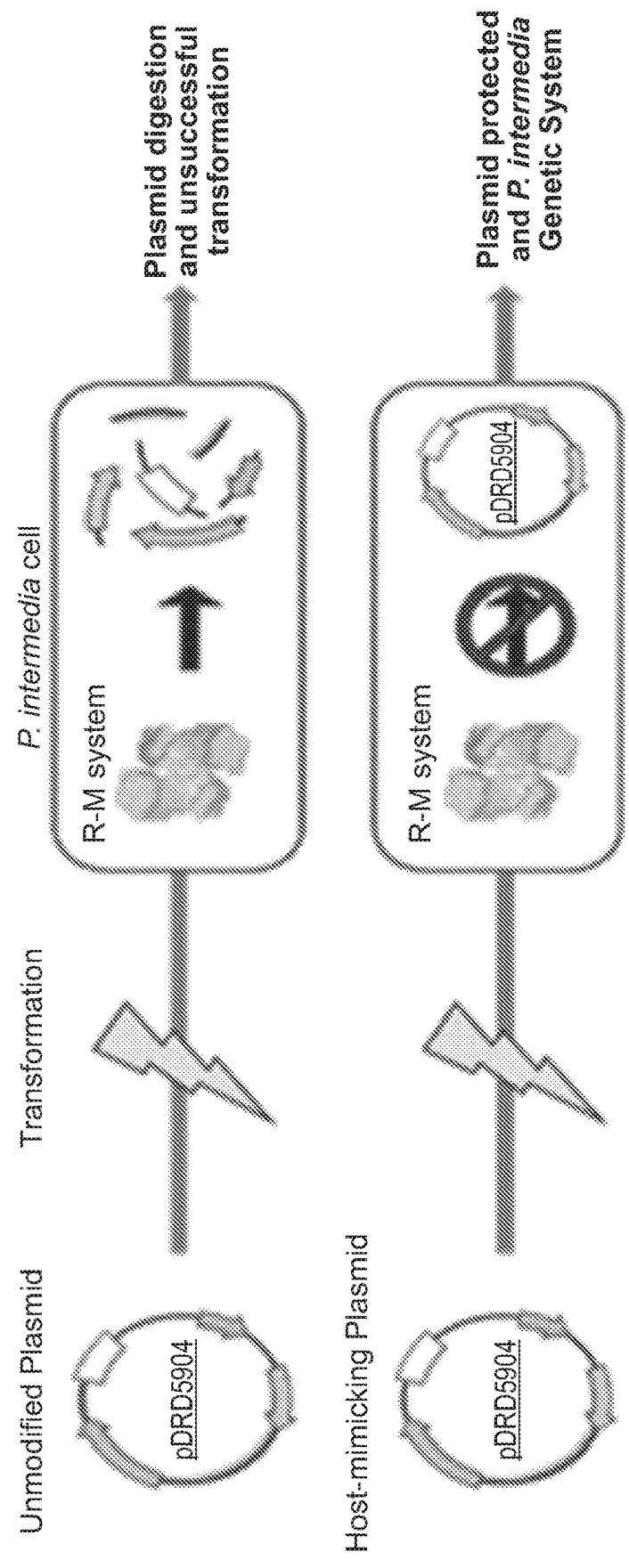

In coding regions, the polynucleotide sequence "targeted" by the restriction endonucleases or CRISPR can be altered using synonymous codon substitution. In non-coding regions, the polynucleotide sequence "targeted" by the restriction endonuclease or CRISPR can be altered by single nucleotide polymorphisms (SNPs). A polynucleotide sequence comprising altered sequences where many, if not all, RM and CRISPR targets have been recoded represents a useful syngenic DNA tool (syngenic genetic tool). A schematic showing an overview of the process to generate syngenic DNA is shown in FIG. 2.

Restriction-Modification (RM) Systems as Genetic Barriers

Restriction-Modification (RM) systems are the most well studied of bacterial defense mechanisms. They are present in over 90% of sequenced bacterial genomes (Roberts et al., Nucleic Acids Res, 2015. 43: pp. D298-9) and are often considered a primitive bacterial innate immune system (Vasu et al., Proceedings of the National Academy of Sciences, 2012. 109(20): p. E1287-E1293). These systems operate via two enzymatic activities, a restriction endonuclease and a modification methyltransferase. The restriction endonucleases recognize and cut specific DNA target sequences in invading DNA, whereas the methyltransferase activity protects the same target sequence within the host's genome by addition of a methyl ($CH_3$) group (Suzuki et al. Transformation. 2012: INTECH Open Access).

Individual RM systems differ with regard to their target sequences, active site architecture, and reaction mechanisms (Vasu et al). Typically, they can be categorized into four different types. Type I-III systems all function by recognizing and cutting a target sequence if it lacks a methyl group. On the contrary, Type IV systems do not use a methyltransferase enzyme. Instead, a methyl-dependent restriction endonuclease cuts a target sequence if it contains a methyl group. As RM systems recognize the methylation status of incoming DNA and degrade inappropriately methylated target sequences, RM systems are a major barrier to man-made genetic tools. To exacerbate this issue during genetic engineering, the DNA targets recognized by RM systems vary greatly in sequence and length, typically ranging from four to twelve base pairs (bp), with 400 different target sequences and over 4,000 RM systems associated enzymes identified to date (Roberts et al.). Furthermore, the number of RM systems present and the target sequences recognized are hyper-variable and highly species specific, often even strain specific (Vasu et al.). Whereas the presence of an RM system is relatively simple to predict based on genome annotation, it is inherently difficult to accurately predict the target sequence that each system recognizes from genome information alone.

Clustered Regularly Interspaced Short Palindromic Repeat (CRISPR) CAS Systems

In recent years, "CRISPR-Cas" technology has rapidly developed into a powerful and versatile molecular biology tool for genome editing, but in bacteria, CRISPRs form an effective bacteriophage defense mechanism. These systems are present in approximately 45% of sequenced bacterial genomes (Grissa et al., Nucleic Acids Res, 2007. 35 p. W52-7) and consist of two general components: a CRISPR array and CRISPR associated (CAS) proteins (Waddington et al., Curr Stem Cell Rep, 2016. 2: pp. 9-20). CRISPR arrays are genomic DNA regions containing a succession of highly conserved repeated sequences (23-44 bp in length) separated by similarly sized "spacers" while Cas proteins are essential for interaction with the this array. A single array can consist of hundreds of repeat-spacer units and each spacer corresponds to previous interactions with invading phage or exogenous DNA molecules (Makarova et al., Nat. Rev. Microbio., 2015. 13(11): pp. 722-36). During CRISPR defense, an endonuclease uses RNA molecules (crRNAs) transcribed from these spacers as targeting molecules to recognize and degrade homologous regions on invading DNA. In addition to the spacer target, a short 2-6 bp sequence called the protospacer adjacent motif (PAM) is also essential for CRISPR activity. The PAM sequence is a component of the invading DNA but is not included in the genomic CRISPR array, allowing the system to distinguish between self and non-self. While the majority of spacer sequences match with regions of bacteriophage genomes, many spacers match plasmids, other mobile genetic elements and chromosomal regions of other bacteria (Barrangou et al., Microbe, 2009. 4(5): p. 224), (Marraffini et al., Science, 2008. 322(5909): pp. 1843-5), (Stern et al., Trends Genet, 2010. 26(8): pp. 335-40). Thus, in addition to their role as an anti-phage immune system, CRISPR-Cas systems constitute a major barrier against the transfer of genes, accessory genetic elements and artificial transformation with man-made genetic tools (Marraffini et al.), (Sapranauskas et al., Nucleic Acids Res, 2011. 39(21): pp. 9275-82), (Semenova et al., Proceedings of the National Academy of Sciences, 2011. 108(25): pp. 10098-10103), (Jiang et al., PLoS Genet, 2013. 9(9): p. e1003844). In the context of genome engineering, access to the genome of the host bacteria provides all the targets recognized by CRISPR defense systems, which are encoded within the CRISPR array. Nevertheless, CRISPR array spacers are hypervariable, as they depend on the temporal interaction of the host with exogenous invading DNA throughout its taxonomic lineage.

In the context of genetic engineering, both defense systems concomitantly form an active barrier against man-made genetic tools, which are perceived as foreign, non-host DNA within new bacterial hosts. To effectively recode genetic tools to be recognized as self by each specific bacterial host, and expedited genetic engineering in new hosts, strain specific information for each bacterial microorganism of interest is required.

Bacteria useful in the methods of the invention include, without limitation, bacteria present in soil, human microbiome, marine bacteria, and other genetically intractable bacteria. In some embodiments, the bacterial cell can selected from the group consisting of, but not limited to, *Actinobacteria*, *Armatimonadetes*, *Aquificae*, *Bacteroidetes*, *Chlamydiae*, *Chloroflexi*, *Caldiserica*, *Chlorobi*, *Chrysiogenetes*, *Cyanobacteria*, *Deferribacteres*, *Deinococcus-Thermus*, *Dictyoglomi*, *Elusimicrobia*, *Euryarchaeota*, *Firmicutes*, *Fusobacteria*, *Fibrobacteres*, *Gemmatimonadetes*, *Lentisphaerae*, *Nitrospirae*, *Planctomycetes*, *Proteobacteria*, *Spirochaetes*, SRI, *Synergistetes*, *Tenericutes*, TM7, *Thermodesulfobacteria*, *Thermomicrobia*, *Thermotogae*, or *Verrucomicrobia*.

In some embodiments, both gram negative and gram positive bacteria may be used. Such gram positive bacteria include, but are not limited to, *Pasteurella* species, *Staphylococci* species, and *Streptococcus* species. Such gram negative bacteria include, but are not limited to, *Escherichia coli*, *Pseudomonas* species, and *Salmonella* species.

In some embodiments, the bacteria can include infectious bacteria. Examples of infectious bacteria include, but are not limited to, *Helicobacter pyloris*, *Borelia burgdorferi*, *Legionella pneumophilia*, *Mycobacteria* sps (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyo-* genes (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtherias, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

In other embodiments, the bacteria is selected from health promoting or probiotic bacteria. Such bacteria include, but are not limited to, *Lactobacillus* species, *Lactococcus* species, *Bifidobacterium* species, *Saccharomyces* species, *Enterococcus* species, *Streptococcus* species, *Pediococcus* species, *Leuconostoc* species, *Bacillus* species, and *Escherichia coli* species.

Method of Creating Genetic Tools Using Syngenic DNA

In one embodiment, the invention provides a method of generating "host-mimicking DNA" or "syngenic DNA" that evades bacterial defense mechanisms. The methods of the invention rely on a simple premise: if a man-made polynucleotide lacks many of the highly specific target recognition sequences (e.g., recognition sites) for the hosts' Restriction Modification (RM) and Clustered Regularly Interspaced Short Palindromic Repeat (CRISPR) systems, it is invisible to these systems and therefore will not be degraded. In one embodiment, about 5%, about 10%, about 15%, about 20%, about 25%. about 30%. about 35%, about 40%, about 45%, about 50%, about 55%, about 60%, about 65%, about 70%, about 75%, about 80%, about 85%, about 90%, about 95%, about 99%, or even 100% of specific target recognition sequences (e.g., recognition sites) for RM and CRISPR systems are altered. The approach takes advantage of a number of factors. First, the recent development of combinatory genome and epigenome sequencing technology. Second, advances in synthetic biology that allow for construction of modularized genetic tools consisting of interchangeable parts. Third, an inherent evolutionary weakness in both RM and CRISPR systems of high specificity for their target sequences, and finally, fourth, the continuously decreasing and relative low cost of DNA synthesis, which has dropped by five orders of magnitude in the past decade.

The method of generating syngenic DNA for use as genetic tools is accordingly broken into four steps: Identification, Assembly, Adaptation and Synthesis. After genome and epigenome sequencing in the first step, the remaining steps are performed in-silico using the syngenic DNA tool (syngenic genetic tool) Generator (SytoGen) pipeline. The syngenic DNA tool (syngenic genetic tool) Generator pipeline will permit the development of tailor made genetic tools for any bacterial strain with genomic and methylome data.

Step One—Identification:

The target recognition sequences (e.g., recognition sites) for both RM and CRISPR systems are highly variable and strain-specific. As such, circumvention of these defenses in each host first requires identification of their individual targets. While a bacterial genome provides access to the CRISPR targets, epigenetic information of methylated DNA sequences is required to determine the RM targets. The PacBio™ Single Molecule Real-Time (SMRT) sequencing is a state-of-the-art sequencing instrument that permits long-read DNA sequencing of complete bacterial genomes and accessory plasmids, from a single library in a single run, and additionally permits the sensitive detection of each methylation site, with single-base resolution, across an entire bacterial genome, e.g., the "methylome" as described by Sanchez-Romero et al. (Curr. Opin. Microbio., 2015. 25: pp. 9-16).

Methylome data provides a means to identify the active RM barriers in the host strain. The PacBio™ SMRT analysis software summarizes the number of methylated motifs, their exact sequence, the number present on the genome and the percentage that contain methylation. To differentiate between a complete RM system versus an incomplete RM system which contains an orphan methyltransferase without an endonuclease partner, this information is utilized as quantitative data. In active RM systems, incomplete methylation of every motif present on the genome would be toxic to the host, as un-methylated motifs are targeted for digestion (Takahashi et al., Journal of bacteriology, 2002. 184 (22): pp. 6100-6108), (Kobayashi et al., Trends Genet, 1998. 14(9): pp. 368-74). Therefore, active RM systems need to protect 100% of the motifs present. Accounting for a small margin of incomplete post-replicative methylation in actively dividing cells, motifs that are methylated greater than 95% are indicative of an active RM system. These sequence motifs are herein considered "RAI targets" which will need to be altered in heterogenous sequences.

Genomic sequence data provides a means to identify the CRISPR barriers in the host strain. Analysis of CRISPR targets requires the detection of CRISPR arrays and their entire complement of spacer sequences. The computational identification of CRISPR arrays from whole Genomic sequence data is possible using a number of rapid and accurate open access command-line executable programs and applications described by (Grissa et al.), (Biswas et al., BMC Genomics, 2016. 17: p. 356), (Alkhnbashi et al., Bioinformatics, 2014. 30(17): pp. 1489-1496), (Bland et al., BMC Bioinformatics, 2007. 8: p. 209), (Edgar et al., BMC Bioinformatics, 2007. 8: p. 18), (Rousseau et al., Bioinformatics, 2009. 25(24): pp. 3317-8). These programs automatically detect, predict and refine CRISPR arrays based on their characteristic repeat-spacer-repeat structure and provide a detailed report of all spacers within the host organisms CRISPR arrays. Once identified, these spacers are herein considered "CRISPR targets" which need to be removed from genetic tools.

Step Two—Assembly:

To assemble functional genetic tools, a modified synthetic biology approach was utilized. Synthetic biology focuses on the construction of biological parts that can be understood, designed, and tuned to meet specific criteria (Lee et al., J Biol Eng, 2011. 5: p. 12). The underlying principle is that genetic tools should be minimalistic, constructed of modularized parts and sequence optimized to allow for compatibility. As genetic parts are modular, they can be assembled into larger integrated systems to solve specific problems or carry out functions that are more complex. Standardized formats for genetic tool assembly have already been proposed to facilitate the simple implementation of synthetic circuits and the distribution of physical parts between different laboratories (Lee et al., J Biol Eng, 2011. 5: p. 12), (Silva-Rocha et al., Nucleic acids research, 2013. 41(D1): pp. D666-D675), (Shetty et al., Biol Eng, 2008. 2: p. 5), (Sarrion-Perdigones et al., PLoS One, 2011. 6(7): p. e21622), with the BioBrick standard being the most adopted (Shetty et al.). Recently, common tools for *E. coli* have been successfully altered to function in different bacterial phyla and the modular design of all-synthetic toolkits for genetic manipulation of bacterial species is now gaining traction. Nevertheless, the static design of re-usable modularized parts, which can be physically assembled or re-assembled for different bacteria, is not applicable to tackling genetically intractable species, which are inherently variable in their genetic barriers. Instead, the core principles of a synthetic biology approach, modularity and compatibility is adopted, but variation in genetic barriers is accounted for by removing the requirement for physical assembly.

The syngenic DNA tool (syngenic genetic tool) Generator pipeline facilitates in-silico design of tailor-made genetic tools, allowing for genetic tool templates to be annotated, modified, assembled, or reassembled from existing or user defined modular parts. The combination of parts can include plasmid chassis, detectable reporters, replication origins, antibiotic resistance cassettes, promoters, repressors, terminators and functional domains, for example, transposons or CRISPR-Cas9 operons. Additional parts, for example, compatible promoters or operators, can be obtained from the desired host genome (generated in Step One). Such genetic parts could be provided, for example and without limitation, in a plasmid backbone, a GFP gene, or antibiotic resistance gene, thus providing a genetic "tool-box" of molecular genetic parts. Compatible replication origins and accessory elements for a large variety of bacterial phyla are widely available from the 4418 complete DNA sequences of bacterial plasmids in the NCBI Plasmid Genomic sequence database (Shintani et al., Front. Microbio., 2015. 6: p. 242). After in silico assembly of the desired genetic tool, adaptation is required via recoding for the new host. Additionally, the DNA sequence of complete (non-modular) genetic tools, with demonstrable functionality within genetically tractable strains, can also be directly subjected to the adaptation step described below. This step permits functional tools from tractable bacterial strains to operate in related intractable strains.

Step Three—Adaptation:

During adaptation, the syngenic DNA tool (syngenic genetic tool) Generator pipeline screens assembled genetic tools for the presence of identified RM and CRISPR targets and recodes their sequences to disguise the tool as self in the desired host. Screening of pre-assembled and pre-circularized tools negates the possibility of inadvertently introducing new targets when merging terminal ends of modularized parts. Due to their relatively short length, it is expected that more RM targets than CRISPR targets are identified in any given DNA sequence. The program will adapt coding and non-coding regions in separate ways.

In coding regions, the sequence of the target can be removed using synonymous codon substitution. A single codon switch is generally sufficient to remove RM targets, while multiple switches may be needed for the longer CRISPR targets. However, in bacteria synonymous codons are not used with equal frequencies, with some codons favored over others by natural selection for translation efficiency and accuracy, known as codon bias (Ermolaeva et al., Curr Issues Mol Biol, 2001. 3(4): p. 91-7). To overcome the possibility of introducing rare or unfavorable codons during the synonymous switch, the preferential codon bias of the desired host is used. The codon bias is determined from annotation and analysis of the genomic sequence data generated in step one.

In non-coding regions, the sequence of target can be disrupted by single nucleotide polymorphisms (SNPs). However, some non-coding regions, such as promoters or sequences with secondary structures, may be non-permissive to substitution by SNPs. Alternatively, if an RM and/or CRISPR target is located within one of these regions, the non-coding region can be replaced with another modular part that lacks the target (re-assembly within the program) or multiple versions of this particular sequence with different SNPs can be generated. After synthesis, variable parts can be physically switched out of the genetic tool to create multiple versions for empirical testing of function. The modular design of these parts, with unique sites at each end for cloning, adhere to standard formats in which the 5' end of one part can be ligated to the 3' end of another part, such as the BioBrick format or an equivalent format, to expedite this process. Upon removal of many, if not all, RM and CRISPR targets within the recoded polynucleotide sequence represents a syngenic DNA tool (syngenic genetic tool) to be synthesized.

Step Four—Synthesis

Physical synthesis of syngenic DNA is no different from standard de-novo DNA synthesis. Therefore, the polynucleotide sequence data obtained from generating syngenic DNA tool (syngenic genetic tools) in-silico is open to be synthesized by any laboratory, in any country and by any commercial company offering DNA synthesis services. The exchange of polynucleotide data offers substantial advantages over the current requirement for obtaining physical plasmids and genetic tools, from individual research labs or investigators. Additionally, the hyper-variability of RM and CRISPR barriers between different bacterial strains suggests that each tool will likely require individual adaptation, to overcome these barriers in genetically intractable strains.

Many commercial companies currently provide synthetic DNA on *E. coli* plasmid backbones. Attaching synthesized DNA to plasmid backbones allows for simple and rapid production of large amounts of synthetic DNA in recombinant *E. coli*. In genetic engineering of tractable bacteria the presence of this backbone is not an issue, once transferred to the new bacterial host this portion of the genetic tool is nonfunctional and surplus to requirement. In one embodiment, a genetic tool synthesized from syngenic DNA can be incorporated into an *E. coli* plasmid backbone. However, the incorporation of a wild type (e.g., non-host-mimicking) *E. coli* plasmid backbones to syngenic DNA sequences could potentially result in degradation of this portion of the circular tool when transferred to intractable species. Alternatively, syngenic backbones can be generated with each new genetic tool synthesized from syngenic DNA.

Alternatively, Minicircles (MCs) can be used to generate syngenic DNA minicircle tools for genetic engineering. Minicircles (MCs) are minimalistic circular expression cassettes devoid of a bacterial plasmid backbone (Kay et al., Nat Biotechnol, 2010. 28(12): p. 1287-9). They are mainly used in gene therapy applications to drive stable expression of transgenes in eukaryote hosts (Dietz et al., Molecular Therapy, 2013. 21(8): p. 1526-1535), superior to levels afforded by conventional plasmids. MCs are produced by attaching a parental plasmid (PP) to a transgene cassette, cultivating it within an *E. coli* host to high cell density, and inducing its recombination. The recombination event generates an isolated transgene on a MC and a separate miniplasmid (MP) containing the backbone replication segment.

In one embodiment, the MP portion is automatically degraded (Dong et al., J Biotechnol, 2013. 166(3): p. 84-7), allowing the MC to be extracted by simple plasmid isolation from the *E. coli* strain. The method described herein has adopted and repurposed MC technology to carry complete syngenic tools and plasmids, instead of single transgenes, to facilitate the generation of syngenic DNA minicircle tools for genetic engineering. In this embodiment, a genetic tool synthesized from syngenic DNA (which can include complete with replication, selection and functional domains for operation in the new host) is attached to a carrier non-syngenic (wild type, non-host-mimicking) parental plasmid (PP) backbone for propagation in recombinant *E. coli*. After induction of recombination, the syngenic DNA minicircle tool is isolated and ready to be transformed to the intractable bacterial host. Additionally, in bacteria that contain putative Type IV RM systems, which target and degrade DNA motifs that contain a methylation, the syngenic DNA tool (syngenic genetic tools) are passaged through commercial and widely available methyl-deficient *E. coli* strains, which have been modified to produce un-methylated DNA (Palmer et al., Gene, 1994. 143(1): pp. 1-12). The widespread use of minicircle DNA technology in gene therapy has also led to development of multiple simplified MC production strategies (Gaspar et al., Hum Gene Ther Methods, 2014. 25(2): pp. 93-105), including in-vitro MC production (Dong et al.), and commercially available kits (SBI System Biosciences), (Kay et al.) and further developments in this field can be utilized to complement the method presented herein.

Genetic Tools

The invention provides a number of genetic tools that are resistant to degradation when introduced into a bacteria of interest. In various embodiments, the genetic tool is an expression vector, a plasmid, replication origin, antibiotic resistance cassette, promoter, repressor, terminator, protein coding domain, transposon, operon, linear DNA knockout cassette or a bacterial genome. The expression vectors can comprise any type of polynucleotides, including, but not limited to DNA, which can be single-stranded or double-stranded, synthesized or obtained in part from natural sources, and which can contain natural, non-natural or altered nucleotides. The expression vectors can comprise naturally-occurring, non-naturally-occurring internucleotide linkages, or both types of linkages. Preferably, the non-naturally occurring or altered nucleotides or internucleotide linkages does not hinder the transcription or replication of the expression vector.

Recombinant expression vectors of the invention can be any suitable expression vectors, and can be used to transform or transfect any suitable host. Suitable vectors include those designed for propagation and expansion or for expression or both, such as plasmids and viruses. The vector can be, for example, the puck series (Ferments Life Sciences, Glen Bernie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGTIO, λGTI 1, λZapII (Stratagene), λEMBL4, and λNM1 149, also can be used. Examples of animal expression vectors include pEUK-Cl, pMAM and pMAMneo (Clontech).

The expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from CoIE1, 2μ plasmid, SV40, bovine papilloma virus, and the like.

The expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the expression vectors include, for example, neomycin/G418 resistance genes, hygromycin resistance genes, histidinol resistance genes, tetracycline resistance genes, and ampicillin resistance genes.

The expression vector can include regulatory sequences, such as transcription and translation initiation and termination codons, which are specific to the type of host (e.g., bacterium) into which the vector is to be introduced, as appropriate.

The expression vector can include a native or nonnative promoter operably linked to the nucleotide sequence encoding the fusion polypeptide (including functional portions and functional variants thereof), or to the nucleotide sequence which is complementary to or which hybridizes to the nucleotide sequence encoding the fusion polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. Promoters of the present invention can be controlled in a constitutive or regulated manner. Such regulated promoters can be inducible or repressible such that expression of the polynucleotide can be enhanced or repressed. Exemplary promoters can include a non-viral promoters or a viral promoters, for example, the SV40 early promoter, an RSV promoter, the cytomegalovirus (CMV) promoter, the steroid inducible mouse mammary tumor virus (MMTV) promoter, Moloney murine leukemia virus (MMLV) promoter, a promoter found in the long-terminal repeat of the murine stem cell virus, or other suitable systems known in the art.

The expression vectors can be designed for either transient expression, for stable expression, or for both. Furthermore, the recombinant expression vectors can be made for constitutive expression or for inducible expression. Inducible expression systems can be responsive the administration of agents, for example antibiotics and can include systems such as tetracycline regulated expression systems or any inducible expression system known in the art.

Implementation in Hardware and/or Software

The methods described herein can be implemented on general-purpose or specially programmed hardware or software. For example, the methods can be implemented by a computer readable medium. Accordingly, the present invention also provides a software and/or a computer program product configured to perform the algorithms and/or methods according to any embodiment of the present invention. It is well-known to a skilled person in the art how to configure software which can perform the algorithms and/or methods provided in the present invention. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like). The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001).

The present invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.) Additionally, the present invention may have preferred embodiments that include methods for providing genetic information over networks such as the Internet as shown in U.S. Ser. Nos. 10/197,621, 10/063,559 (US Pub No 20020183936), Ser. Nos. 10/065,856, 10/065,868, 10/328,818, 10/328,872, 10/423,403, and 60/482,389.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Defining the Methylome of *P. intermedia*

Restriction Modification (RM) systems and the cognate recognition sequences utilized by bacteria are species-specific, which require empirical analysis for each species of interest (FIG. 1). In bacteria, post-replicative modification of DNA by methyltransferases results in three types of epigenetic markers: 5-methylcytosine (5mC), N6-methyladenine (6 mA) and N4-methylcytosine (4mC). The data indicates that *P. intermedia* gDNA is completely resistant to restriction endonucleases that recognize the commonly occurring 5'-GATC-3' sequence (Sau3AI, MboI, DpnI, and DpnII), demonstrating that *P. intermedia* ATCC25611 genomic DNA (gDNA) is methylated at both the adenine and the cytosine residues of this sequence ($G^{m\text{-}}AT^{m\text{-}}C$). As such, one of the RM barriers to exogenous DNA transformation may have been uncovered. However, it is unlikely that this is the only RM system present in *P. intermedia*. The restriction enzyme database, REBASE, identifies eight potential RM systems present in the *P. intermedia* genome with putative (n=2) or unknown (n=6) recognition sequences. Fortunately, an innovative technology, Single Molecule Real-Time (SMRT) sequencing, has recently become available which allows rapid and sensitive detection of each methylation site, with single-base resolution, across an entire bacterial genome (i.e. the bacterial methylome).

Currently, methylome analysis can only be accomplished using the PacBio™ RS-II sequencing platform. It is performed using a polymerase enzyme which adds fluorescently labeled bases to a DNA template while the RS-II platform records both the sequence of bases added and the kinetic information (milliseconds) between successive additions, forming a sequencing trace. DNA templates containing a methylation marker cause the polymerase to stall leading to a delay in the sequence trace (FIG. 3, top panel). This kinetic information is used to identify the exact sites in the target DNA that have been methylated and the type of marker present (5mC, 6 mA or 4mC) based on their characteristic trace. Determination of the *P. intermedia* methylome by SMRT sequencing can therefore be used to reveal the exact recognition sequences utilized by each of its RM systems. Purified DNA isolated from *P. intermedia* at mid-logarithmic growth will be sequenced using an RS-II instrument. Data reads will be processed and mapped to the *P. intermedia* genome and kinetic information measured will be analyzed using the PacBio™ SMRT-Portal platform to identify methylated positions. It is expected that SMRT sequencing will allow the identification of the *P. intermedia* methylome and specifically the identification of the cognate recognition sequences of its RM systems.

Example 2: The Use of a Host-Mimicking Strategy to Create a *P. intermedia* Genetic System There is currently no genetic system available for *P. intermedia* and there has been very limited success in the genetic transformation of *Prevotella* species in general. RM systems have already been highlighted as contributory factors for the poor transformation efficiencies of related species *Prevotella bryantii* and *Prevotella ruminicola* and it is hypothesized they are the root cause of the transformation-barrier in *P. intermedia*. Utilizing the genome wide data obtained by the experiments described in Example 1, which define specific methylated sequences present in *P. intermedia*, a host-mimicking strategy will be utilized (FIG. 3, bottom panel) with the pDRD5904 plasmid to circumvent these RM systems.

Methylations are removed via synonymous codon substitution using a splicing by overlap extension (SOEing) technique. If more than five recognition sequences are present a de-novo DNA synthesis coupled with codon substitution is utilized to generate an entirely synthetic pDRD5904 plasmid; lacking all *P. intermedia* RM system recognition sequences. This syngenic pDRD5904 plasmid is then transformed to competent *P. intermedia* by electroporation using techniques already developed in house. This is expected to be the first successful transformation of *P. intermedia* with exogenous DNA. Methylome analysis via SMRT sequencing and use of the syngenic host-mimicking strategy for exogenous plasmid DNA represents an entirely novel and innovative approach to developing a genetic system for *P. intermedia*.

Example 3—Development of a *P. intermedia* Genetic System Using a Host-Mimicking Strategy The approach for the development of a host-mimicking DNA system for *P. intermedia* presented herein is an innovative and original approach to a common problem. Without intending to be bound by theory, the resistance of *P. intermedia* to plasmid transformation is likely based on its restriction-modification and/or CRISPR systems. The gold standard for proof of gene function is to use targeted disruption to eliminate function. Unfortunately, this is not possible in *P. intermedia*, since no system is available for its genetic manipulation. This lack of genetic accessibility is a significant barrier to progress in *P. intermedia* research, and prevents us from generating loss of function mutants. The objective of this example is to develop a plasmid for transformation of *P. intermedia*.

Numerous attempts to transform *P. intermedia* utilizing functional plasmids from related bacterial species (*Bacteroides/Porphyromonas/Prevotella*) with varied origins of replication and antibiotic selection markers have been conducted, but none of these were able to confer antibiotic resistance. In addition, a small native plasmid of *P. intermedia* strain YHBi containing genes for replication and mobilization proteins was isolated and used to construct a *E. coli/Prevotella* shuttle vector designated pDRD5904. However, attempts have been unsuccessful in transforming this plasmid. The failure of this plasmid despite the presence of compatible replicative machinery led us to consider that restriction-modification systems were inhibiting transformation.

Restriction-modification (RM) systems allow bacterial cells to distinguish between their own DNA and foreign DNA. These systems typically operate through a restriction endonuclease activity that degrades the foreign DNA via a specific recognition sequence, and a modification methyltransferase activity that protects the same recognition sequence on host DNA through addition of a methyl group. RM systems typically serve as a cellular defense from invading bacteriophage but concomitantly form an active barrier to man-made exogenous DNA during genetic engineering. Since the cognate recognition sequences utilized by bacterial restriction modification (RM) systems are species-specific empirical analysis is required for each species of interest (Suzuki, 2012). The restriction enzyme database, REBASE, currently identifies eight potential RM systems present in the *P. intermedia* genome with putative (n=2) or unknown (n=6) recognition sequences (Roberts et al, 2015).

Figure 4A:
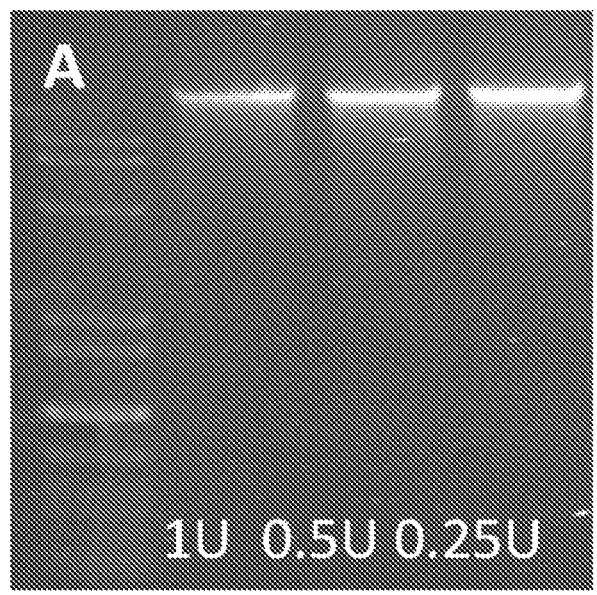
FIG. 4A is an image of an electrophoretic gel showing that *P. intermedia* DNA is resistant to digestion with the methylation-sensitive enzyme Sau3AI.
Figure 4B:
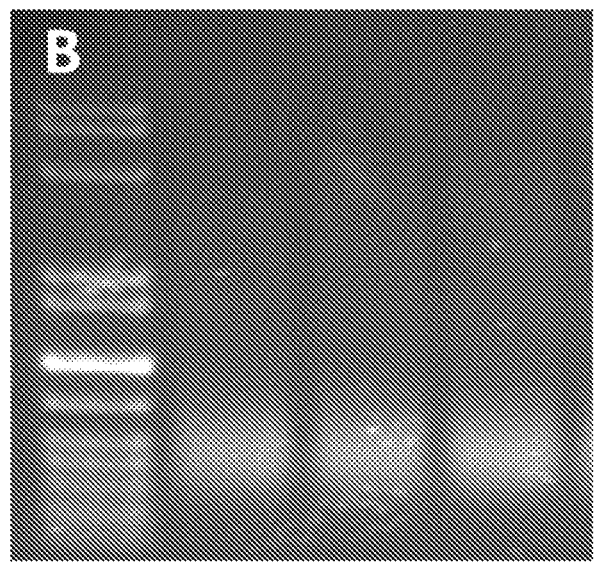
FIG. 4B is an image of an electrophoretic gel showing that F. *Nucleatum* DNA is completely digested by Sau3AI. As shown in each gel image, the left-most lane indicates molecular weight (MW) markers; U indicates units of enzyme added in each lane.

These experiments have demonstrated directly that *P. intermedia* DNA is resistant to digestion with Sau3AI, which is sensitive to methylation on the cytosine residue of the GATC sequence of DNA (i.e. will not digest/cut the sequence GAT$^m$C)) (FIG. 4A), while under identical conditions, *F. nucleatum* DNA is completely digested (FIG. 4B). It is hypothesized that these RM systems are the root cause of the transformation-barrier in *P. intermedia* and that circumvention of these RM systems are required for the development of a genetic system for this pathogen. Importantly, a novel sequencing technology, Single Molecule Real-Time (SMRT) sequencing, has recently become available which allows rapid and sensitive detection of each methylation site, with single-base resolution, across an entire bacterial genome (e.g., the bacterial methylome). SMRT sequencing identifies methylation sites based on kinetic analysis of nucleotide addition. The presence of a methyl group on the template molecule slows the polymerase and the real-time detection system identifies these lags in polymerization rate as sites of methylation. SMRT sequencing was used to define the complete methylomes of both *P. intermedia* ATCC25611 and the clinical isolate strain-17. This innovative approach has allowed us to characterize the exact recognition sequences utilized by each RM system of *P. intermedia* (Table 1), and identified eleven reoccurring motifs that are methylated across the *P. intermedia* ATCC25611 genome. Table 1 shows eleven methylated motifs, representing potential restriction sites, were identified in *P. intermedia* DNA using SMRT sequencing. The percent (%) genome indicates the percent of sites in the genome that are methylated. The number (#) in plasmid indicates the number of sites identified in plasmid pDRD5904. This analysis also provided deep sequencing (100× coverage) results, allowing improved annotation of this genome, which will aid LC/MS/MS analyses.

Using this knowledge of the RM recognition sequences used by *P. intermedia*, a host-mimicking strategy will be employed with the syngenic pDRD5904 plasmid to circumvent all RM systems. Since numerous novel methylation sites were identified by SMRT sequencing in *P. intermedia*, the approach described herein will involve construction/synthesis of a version of pDRD5904 lacking all *P. intermedia* RM recognitions sequences.

All RM targets, inferred from methylation data across the *P. intermedia* genome, will be removed via in-silico removal of individual targets using synonymous codon substitutions and single nucleotide polymorphisms, follows by de-novo DNA synthesis. The resultant plasmid will lack most or all *P. intermedia* RM system recognition sequences, while maintaining the protein coding and replication information. This synthetic pDRD5904 plasmid will then be transformed to competent *P. intermedia* by electroporation using techniques already developed in house. The initial transformation efficiencies may be low, and can be optimized using a variety of approaches known in the art.

TABLE 1

Eleven methylated motifs, representing potential restriction sites, were identified in *P. intermedia* DNA using SMRT sequencing.

| Motif | Methylation | % Genome | # in plasmid |
|---|---|---|---|
| GATC | m6A | 99 | 15 |
| GGATG | m6A | 99 | 9 |
| CATCC | m6A | 99 | 9 |
| GAGNNNNTAC | m6A | 98 | 3 |
| GTANNNNCTC | m6A | 98 | 3 |
| GCAGC | m6A | 81 | 26 |
| GCAGCNNNG | m4C | 32 | 4 |
| AGYNNNNNRTTC | m6A | 95 | 3 |
| GAAYNNNNNRCT | m6A | 78 | 3 |
| CAGNNNNNNTTG | m6A | 67 | 2 |
| CAANNNNNNCTG | m6A | 67 | 2 |

Example 4—Use a Host-Mimicking Strategy to Create a *P. intermedia* Genetic System The location of the recognition motifs corresponding to each *P. intermedia* RM system were identified in the pDRD5904 replicative vector. In addition, the ORFs of three antibiotic resistance cassettes (Erythromycin, Chloramphenicol, Cefoxitin) commonly used for transformation of *Bacteroides/Porphyromonas* species were also screened for the presence of these Restriction-Modification (RM) motifs.

Utilizing in-silico (DNAstar bioinformatic suite; Seqbuilder) analysis, each RM motif was sequentially removed from these DNA sequences using single nucleotide substitution or codon optimization when the motif occurred outside or inside of an open reading frame, respectively. This generated a series of DNA "parts" which lack all *P. intermedia* RM recognition motifs and can be used to construct linear DNA knockout cassettes and replicative vectors for *P. intermedia*. No CRISPR targets corresponding to the *P. intermedia* defense system were identified on the pDRD5904 plasmid or antibiotic resistance cassettes. The "parts" were synthesized by Genscript and will be tested.

Three synthetic constructs were generated; two syngenic antibiotic resistance genes under the control of the *P. intermedia* RpoD promoter and one complete plasmid, designated pPin-1, which contains the replicative machinery of pDRD5904 and a syngenic chloramphenicol resistance gene as a selection marker, also under the control of the *P. intermedia* RpoD promoter. This complete plasmid will be the first to be transformed to *P. intermedia*. To allow for optimization of transformation efficiency within *P. intermedia*, the remaining antibiotic resistance gene "parts" have been designed with unique terminal restriction sites to allow for simple switching out with pPin-1: resulting in two more *P. intermedia* plasmids (pPin-2 and pPin-3) with erythromycin and cefoxitin resistance selection markers.

Furthermore, the PacBio™ SMRTseq data for *Prevotella intermedia* has been uploaded to the Restriction Enzyme Database (REBASE).

Example 5—the Syngenic DNA Method Applied to Human Oral Microbiome

The human oral microbiome is an ideal community to initially demonstrate the transformative potential of the syngenic DNA method. The oral cavity was among the first of five major body regions included in the original Human Microbiome Project (HMP) and is one of the best characterized microbial habitats with respect to diversity, composition and structure. The oral microbiome also contains the largest core of commonly shared microbes among unrelated individuals, when compared to other habitats such as gut or skin. Furthermore, accumulating bodies of evidence link numerous members of the oral microbiome to human systemic diseases, including cardiovascular disease, preterm births, pulmonary disease as well as pancreatic and colorectal cancer.

The Human Oral Microbiome Database (HOMD), maintained and curated at the Forsyth Institute, indicates that over 700 prokaryote species are present in the oral cavity and the Forsyth internal culture collection has amassed representative strains of the 400 currently cultivable species. It has been estimated that approximately 90% of these cultivable oral bacterial species are not-yet genetically tractable. Accordingly, this culture collection provides an ideal proving ground for the syngenic DNA method and the technologies described herein will be used to characterize approximately 200 of these bacterial strains isolated from the human oral microbiome. A physical and logical expansion of Forsyth Institutes current HOMD platform is proposed: The world's first publically accessible Human Oral Microbiome Culture (HOMC) collection will be generated, in addition to expanding the current HOMD database to include curated data sufficient for genetic engineering of each model organism within the collection.

Figure 5:
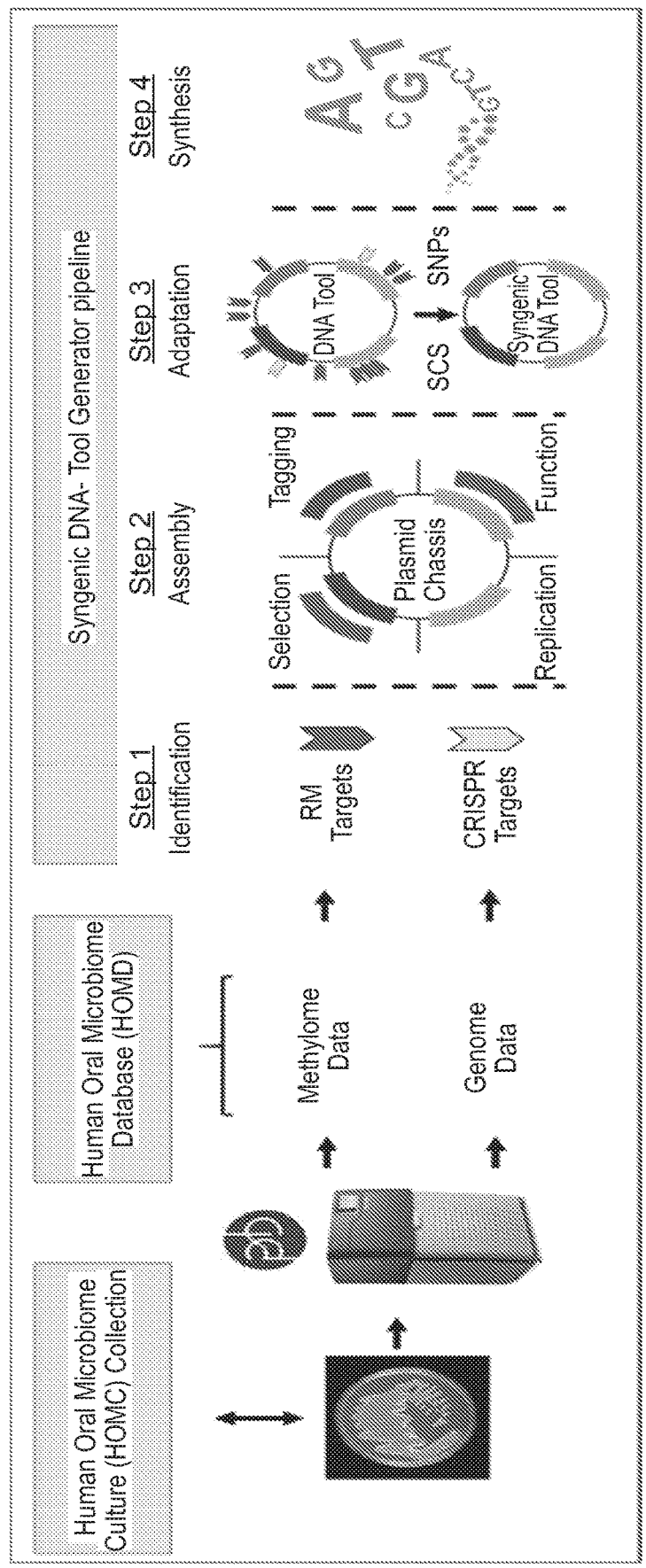
FIG. 5 provides a schematic showing the process for generating host-mimicking DNA (syngenic DNA) including Human Oral Microbiome Culture (HOMC) Collection creation and Human Oral Microbiome Database (HOMD) expansion, and showing the identification, assembly, adaptation and synthesis steps of the Syngenic DNA-Tool Generator pipeline.

The HOMD expansion will provide: 1) High-quality complete genome sequences (50× coverage as closed contigs) 2) Epigenomic data in the form of individual "methylomes", 3) detailed curation of the exact genetic barriers present, which can be directly applied to the syngenic DNA tool (syngenic genetic tool) Generator pipeline to generate tailored-made genetic tools and 4) parametrically optimized conditional requirements for electroporation based transformation. The combination of the HOMC collection, the expanded HOMD database, the syngenic DNA tool (syngenic genetic tool) Generator pipeline will therefore provide a currently unavailable resource to the field of oral and systemic microbiology, and effectively demonstrate the transformative potential of the syngenic DNA method. The establishment of a physical repository of approximately 200 genetically tractable oral bacterial strains, representing species across six different phyla (Firmicutes, Bacteroidetes, Proteobacteria, Actinobacteria, Spirochaetes, and Fusobacteria) will rapidly accelerate fundamental investigations into the role of these species in human health and disease. The overarching goal of this project will be to develop a broadly applicable methodology to overcome a genetically intractable phenotype in any bacteria. A schematic overview of this process is shown in FIG. 5.

Example 6: The Syngenic DNA Method Applied to *Treponema denticola*

Among periodontal anaerobic pathogens, the oral spirochetes, and especially *Treponema denticola*, have been associated with periodontal diseases such as early-onset periodontitis, necrotizing ulcerative gingivitis, and acute pericoronitis. Transformation of a *T. denticola* strain by allelic replacement mutagenesis and by shuttle plasmids was first reported over 20 years ago, but subsequent progress in this area continues to be hindered by extremely low transformation efficiency. Currently, *T. denticola* is somewhat tractable for simple gene knockouts; however, basic methods such as complementation analysis and expression of heterologous genes are problematic. The available shuttle plasmid systems have an extremely limited ability to replicate in the most widely studied *T. denticola* strain, likely due to the presence of restriction modification/CRISPR systems. Thus, while plasmid-based methodologies are straightforward in the study of many prokaryotes, such studies present major obstacles to the rigorous molecular genetic analysis of treponemes. Accordingly, a more efficient, reliable, low cost, and quick method for transforming *T. denticola* is required. One feature of the present invention is the application of the SyngenicDNA method to overcome the transformation barrier in two different *T. denticola* strains, ATCC 35405 and ATCC 33520.

In a first step, PacBio™ SMRT sequencing data and publicly available PacBio™ data within REBASE was used to identify the methylated motifs present in the desired transformation host, *T. denticola* strains ATCC 35405 and ATCC 33520. Sequence and methylome data was subsequently processed through the publicly available Restriction Enzyme Database (REBASE) to identify the Restriction-Modification system targets for both strains (FIG. 6). The genomes were also screened for the presence of Clustered regularly interspaced short palindromic repeats (CRISPRs) using a combination of CRISPRFinder, CRISPRdetect, and CRISPROne (omics.informatics.indiana.edu/CRISPROne) while protospacer targets were analyzed using the CRISPRTarget server. The CRISPR targets of *T. denticola* strains were identified and shown in (FIG. 7).

Figure 8A:
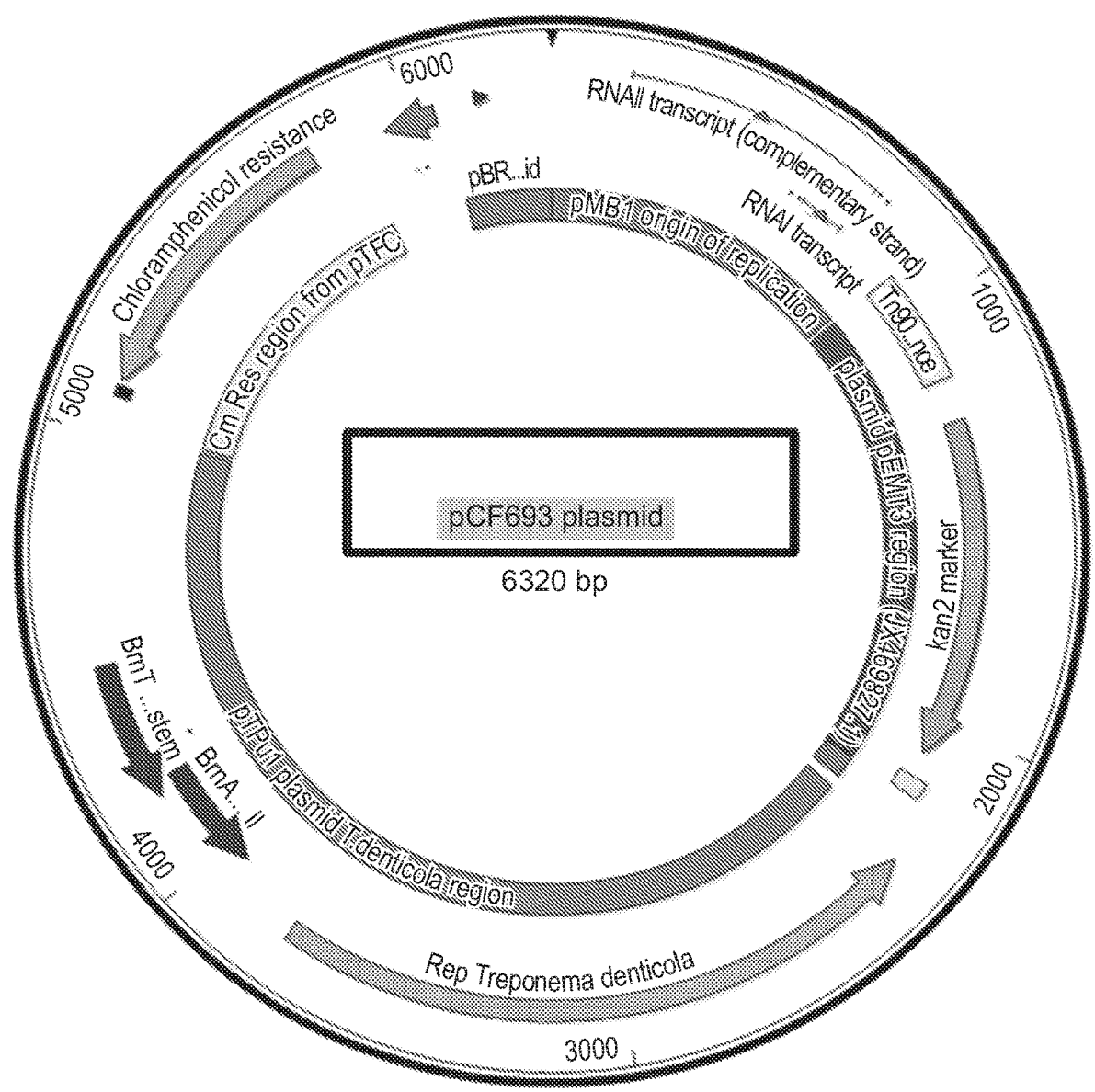
FIG. 8A an FIG. 8B provides two images pCF693 plasmid, the image on the left showing a functional *T. denticola* plasmid, pCF693, for application of the SyngenicDNA method (FIG. 8A). On the right is an image of the pCF693 plasmid which has target sites highlighted (FIG. 8B).

Next, a plasmid was selected with previous demonstrable functionality in *T. denticola*, pCF693 (FIG. 8A), for application of the syngenicDNA method and subsequent transformation of *T. denticola* strains. The DNA sequence (6320 bp) of the pCF693 plasmid was determined using commercial plasmid DNA sequencing. The plasmid map and annotation of the pCF693 plasmid was performed in-silico using a combination of publicly and commercially available tools (Plasmapper, Basic Local Alignment Search Tool (BLAST) analysis blast.ncbi.nlm.nih.gov/Blast.cgi, and the bioinformatic suite DNAstar Lasergene www.dnastar.com/t-allproducts.aspx). The plasmid pCF693 is an *E. coli-T. denticola* shuttle plasmid that contains elements to confer autonomous replication and chloramphenicol resistance in *S. aureus* (outer dark grey box).

Using the information in Step 1 and Step 2, the sequence of the pCF693 genetic tool was screened for the presence of the RM and CRISPR targets identified: 1) $G^{m6}$ ATC: a methyl-directed restriction system with 18 sites present in pCF693. These sites are not to be eliminated as passage through a methyl free *E. coli* strain (such as ER2796) would bypass this methyl barrier upon transformation. 2) $^{m4}C^{m6}$ TCTTC: an R-M system with 4 sites in the pCF693 plasmid requiring elimination (3× coding ORF, 1 non-coding region). 3) $GGNC^{m4}$ C: RM system with 2 sites in the pCF693 plasmid requiring elimination (2× non-coding regions). 4) Cm 6 AG TDCC: an RM system with 3 sites in the pCF693 plasmid requiring elimination (1× coding ORF, 2× non-coding regions). 5) $CN^{m6}$ AC TTC: an RM system with 3 sites in the pCF693 plasmid requiring elimination (2× coding ORFs, 1× non-coding region).

Figure 8B:
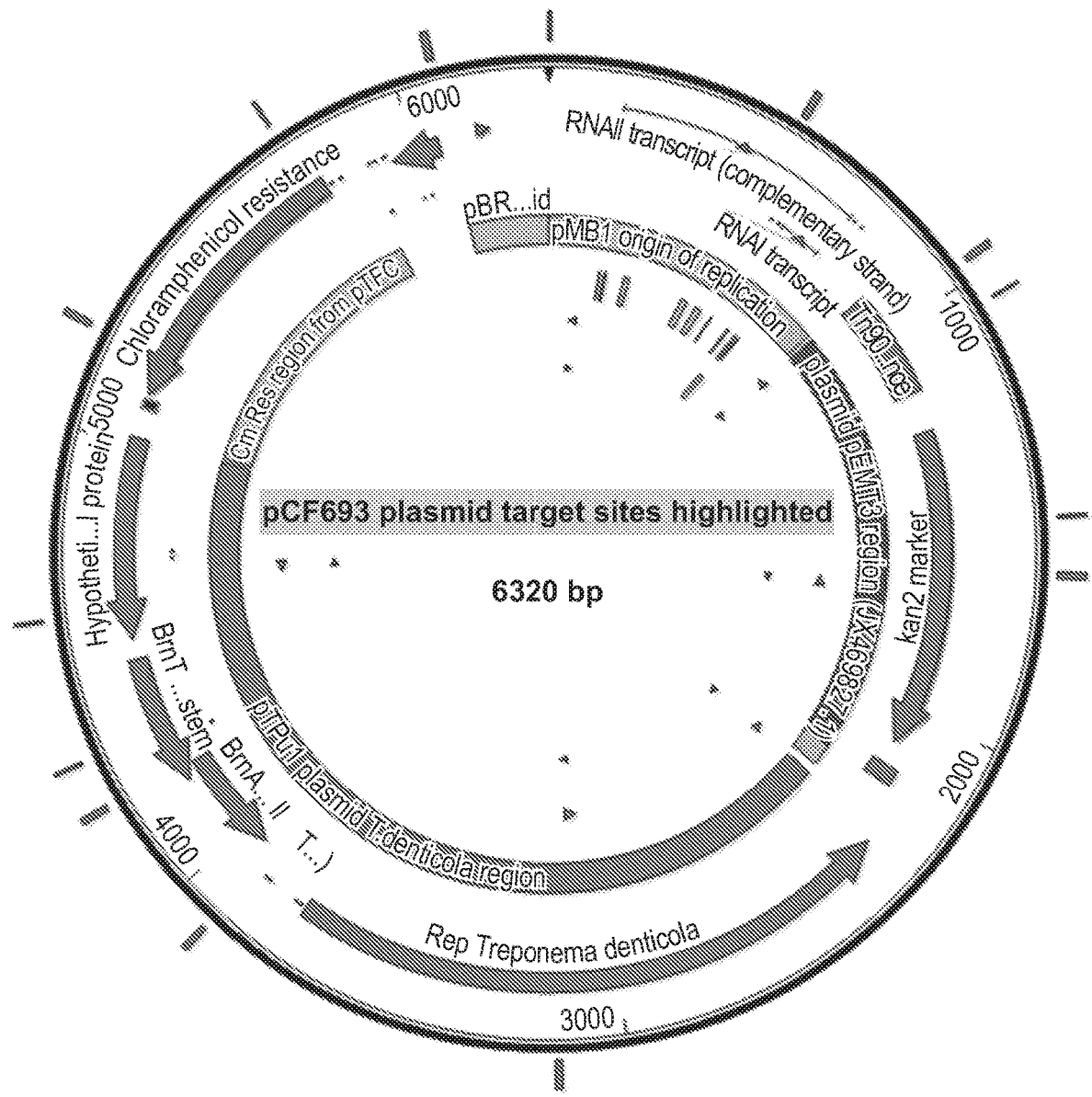
Figure 9:
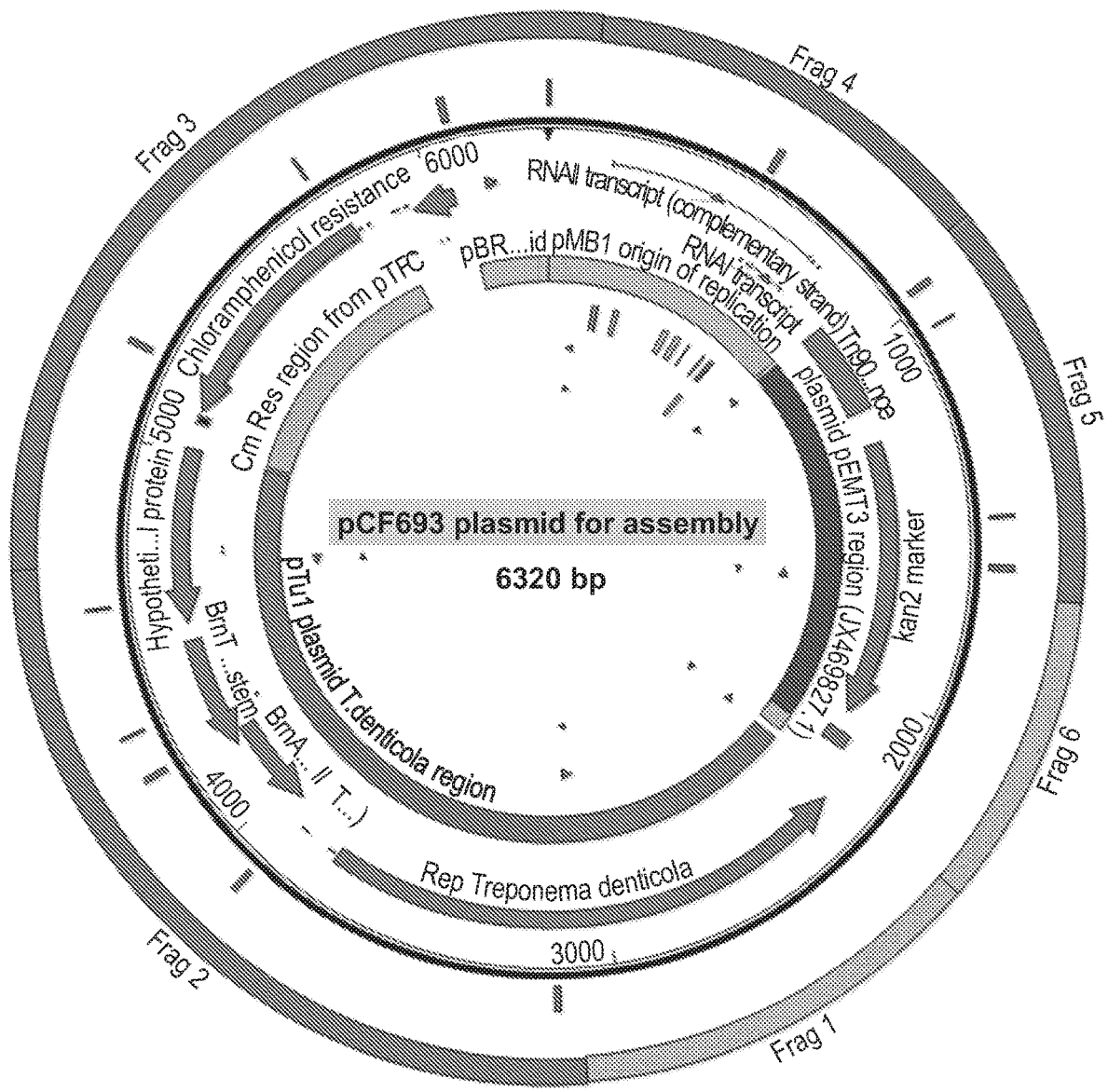
FIG. 9 provides an image of the assembly strategy of syngenic pCF693 plasmid for transformation to *T. denticola*.

In addition, the motifs $CTA^{m6}$ AT and $RA^{m6}$ ATTY were identified, however these are the result of an apparent Type-III and a Type-II Orphan methyltransferase system and as a result are not to be eliminated unless confirmed that a corresponding restriction domain was present. The sequence of this plasmid was also screened for CRISPR targets identified in Step 2, but no such targets were present. A summary of all targets across the sequence of this plasmid is shown in FIG. 8B.

Next, the RM target sequences were eliminated using either synonymous codon substitution (if target existed within an open reading frame) or single nucleotide polymorphism (if target existed outside of an open reading frame). The modified sequence of the entire pCF693 with synonymous changes and single nucleotide polymorphisms is detailed below.

DNA Sequence Alignment and Comparison of Original pCF693 Plasmid with Syngenic pCF693 Version after Elimination of *T. denticola* Genetic Barriers Target Motifs

```
pCF693original
cttccgcttcctcgctcactgactcgctgcgctcggtcgttcggctgcggcgagcggtat pCF693syngenic
cAAccgcttcctcgctcactgactcgctgcgctcggtcgttcggctgcggcgagcggtat
*:.:******************************************************** pCF693original
cagctcactcaaaggcggtaatacggttatccacagaatcaggggataacgcaggaaaga pCF693syngenic
cagctcactcaaaggcggtaatacggttatccacagaatcaggggataacgcaggaaaga
************************************************************ pCF693original
acatgtgagcaaaaggccagcaaaaggccaggaaccgtaaaaaggccgcgttgctggcgt pCF693syngenic
acatgtgagcaaaaggccagcaaaaggccaggaaccgtaaaaaggccgcgttgctggcgt
************************************************************ pCF693original
ttttccataggctacgcccccctgacgagcatcacaaaaatcgacgctcaagtcagaggt pCF693syngenic
ttttccataggctacgcccccctgacgagcatcacaaaaatcgacgctcaagtcagaggt
************************************************************ pCF693original
ggcgaaacccgacaggactataaagataccaggcgtttccccctggaagctccctcgtgc pCF693syngenic
ggcgaaacccgacaggactataaagataccaggcgtttccccctggaagctccctcgtgc
************************************************************ pCF693original
gctctcctgttccgaccctgccgcttaccggatacctgtccgcctttctcccttcgggaa pCF693syngenic
gctctcctgttccgaccctgccgcttaccggatacctgtccgcctttctcccttcgggaa
************************************************************ pCF693original
gcgtggcgctttctcatagctcacgctgtaggtatctcagttcggtgtaggtcgttcgct pCF693syngenic
gcgtggcgctttctcatagctcacgctgtaggtatctcagttcggtgtaggtcgttcgct
************************************************************
``` pCF693original
ccaagctgggctgtgtgcacgaaccccccgttcagcccgaccgctgcgccttatccggta pCF693syngenic
ccaagctgggctgtgtgcacgaaccccccgttcagcccgaccgctgcgccttatccggta
************************************************************ pCF693original
actatcgtcttgagtccaacccggtaagacacgacttatcgccactggcagcagccactg pCF693syngenic
actatcgtcttgagtccaacccggtaagacacgacttatcgccactggcagcagccactg
************************************************************ pCF693original
gtaacaggattagcagagcgaggtatgtaggcggtgctacagagttcttgaagtggtggc pCF693syngenic
gtaacaggattagcagagcgaggtatgtaggcggtgctacagagttcttgaagtggtggc
************************************************************ pCF693original
ctaactacggctacactagaagaacagtatttggtatctgcgctctgctgaagccagtta pCF693syngenic
ctaactacggctacactagaagaacagtatttggtatctgcgctctgctgaagccagtta
************************************************************ pCF693original
ccttcggaaaaagagttggtagctcttgatccggcaaacaaaccaccgctggtagcggtg pCF693syngenic
ccttcggaaaaagagttggtagctcttgatccggcaaacaaaccaccgctggtagcggtg
************************************************************ pCF693original
gtttttttgtttgcaagcagcagattacgcgcagaaaaaaaggatctcaagaagatcctt pCF693syngenic
gtttttttgtttgcaagcagcagattacgcgcagaaaaaaaggatctcaagaagatcctt
************************************************************ pCF693original
tgatcttttctacggggtctgacgctcagtggaacgaaaactcacgttaagggattttgg pCF693syngenic
tgatcttttctacggggtctgacgctcagtggaacgaaaactcacgttaagggattttgg
************************************************************ pCF693original
tcatgagattatcaaaaaggatcttcacctagatccttttcctcgagatccgcgcgttta pCF693syngenic
tcatgagattatcaaaaaggatcttcacctagatccttttcctcgagatccgcgcgttta
************************************************************ pCF693original
atgaccagcacagtcgtgatggcaaggtcagaatagcgctgaggtctgcctcgtgaagaa pCF693syngenic
atgaccagcacagtcgtgatggcaaggtcagaatagcgctgaggtctgcctcgtgaGgaa
*******************************************************.* pCF693original
ggtgttgctgactcataccaggcctgaatcgccccatcatccagccagaaagtgagggag pCF693syngenic
ggtgtAgTtAactcataccaggcctgaatcgccccatcatccagccagaaagtgagggag
     ***.
*.********************************************** pCF693original
ccacggttgatgagagctttgttgtaggtggaccagttggtgattttgaacttttgcttt pCF693syngenic
ccacggttgatgagagctttgttgtaggtgCaGcagttggtgattttgaacttttgcttt
                             *****************************  *
*************************

```
pCF693original
gccacggaacggtctgcgttgtcgggaagatgcgtgatctgatccttcaactcagcaaaa pCF693syngenic
gccacggaacggtctgcgttgtcgggaagatgcgtgatctgatccttcaactcagcaaaa
************************************************************ pCF693original
gttcgatttattcaacaaagccacgttgtgtctcaaaatctctgatgttacattgcacaa pCF693syngenic
gttcgatttattcaacaaagccacgttgtgtctcaaaatctctgatgttacattgcacaa
************************************************************ pCF693original
gataaaaatatatcatcatgaacaataaaactgtctgcttacataaacagtaatacaagg pCF693syngenic
gataaaaatatatcatcatgaacaataaaactgtctgcttacataaacagtaatacaagg
************************************************************ pCF693original
ggtgttatgagccatattcaacgggaaacgtcttgctcgaggccgcgattaaattccaac pCF693syngenic
ggtgttatgagccatattcaacgggaaacgtcttgctcgaggccgcgattaaattccaac
************************************************************ pCF693original
atggatgctgatttatatgggtataaatgggctcgcgataatgtcgggcaatcaggtgcg pCF693syngenic
atggatgctgatttatatgggtataaatgggctcgcgataatgtcgggcaatcaggtgcg
************************************************************ pCF693original
acaatctatcgattgtatgggaagcccgatgcgccagagttgtttctgaaacatggcaaa pCF693syngenic
acaatctatcgattgtatgggaagcccgatgcgccagagttgtttctgaaacatggcaaa
************************************************************ pCF693original
ggtagcgttgccaatgatgttacagatgagatggtcagactaaactggctgacggaattt pCF693syngenic
ggtagcgttgccaatgatgttacagatgagatggtcagactaaactggctgacggaattt
************************************************************ pCF693original
atgcctcttccgaccatcaagcatttttatccgtactcctgatgatgcatggttactcacc pCF693syngenic
atgcctctGccgaccatcaagcatttttatccgtactcctgatgatgcatggttactcacc
                ********
****************************************************** pCF693original
actgcgatccccggaaaaacagcattccaggtattagaagaatatcctgattcaggtgaa pCF693syngenic
actgcgatccccggaaaaacagcattccaggtattagaagaatatcctgattcaggtgaG
***********************************************************.

pCF693original
aatattgttgatgcgctggcagtgttcctgcgccggttgcattcgattcctgtttgtaat pCF693syngenic
aatattgttgatgcgctggcagtgttcctgcgccggttgcattcgattcctgtttgtaat
************************************************************ pCF693original
tgtccttttaacagcgatcgcgtatttcgtctcgctcaggcgcaatcacgaatgaataac pCF693syngenic
tgtccttttaacagcgatcgcgtatttcgtctcgctcaggcgcaatcacgaatgaataac
************************************************************
```

-continued pCF693original
ggtttggttgatgcgagtgattttgatgacgagcgtaatggctggcctgttgaacaagtc pCF693syngenic
ggtttggttgatgcgagtgattttgatgacgagcgtaatggctggcctgttgaacaagtc
************************************************************ pCF693original
tggaaagaaatgcataaacttttgccattctcaccggattcagtcgtcactcatggtgat pCF693syngenic
tggaaagaaatgcataaacttttgccattctcaccggattcagtcgtcactcatggtgat
************************************************************ pCF693original
ttctcacttgataaccttattttgacgaggggaaattaataggttgtattgatgttgga pCF693syngenic
ttctcacttgataaccttattttgacgaggggaaattaataggttgtattgatgttgga
************************************************************ pCF693original
cgagtcggaatcgcagaccgataccaggatcttgccatcctatggaactgcctcggtgag pCF693syngenic
cgagtcggaatcgcagaccgataccaggatcttgccatcctatggaactgcctcggtgag
************************************************************ pCF693original
ttttctccttcattacagaaacggcttttcaaaaatatggtattgataatcctgatatg pCF693syngenic
ttttctccttcattacagaaacggcttttcaaaaatatggtattgataatcctgatatg
************************************************************ pCF693original
aataaattqcagtttcatttgatgctcgatgagttttctaatcagaattggttaattgg pCF693syngenic
aataaattgcagtttcatttgatgctcgatgagttttctaatcagaattggttaattgg
************************************************************ pCF693original
ttgtaacactggcagagcattacgctgacttgacgggacggcggctttgttgaataaatc pCF693syngenic
ttgtaacactggcagagcattacgctgacttgacgggacggcggctttgttgaataaatc
************************************************************ pCF693original
gaacttttgctgagttgaaggatctcgaggtgcaccatatgcggtgtgaaataccgcaca pCF693syngenic
gaacttttgctgagttgaaggatctcgaggtgcaccatatgcggtgtgaaataccgcaca
************************************************************ pCF693original
gatgcgtaaggagaaaataccgcatcaggcgccattcgccattcaggctgcctcggtacc pCF693syngenic
gatgcgtaaggagaaaataccgcatcaggcgccattcgccattcaggctgcctcggtacc
************************************************************ pCF693original
cggggatccgcaggggactgacatatttaaagctgagatttatggttgcggagaaattgt pCF693syngenic
cggggatccgcaggggactgacatatttaaagctgagatttatggttgcggagaaattgt
************************************************************ pCF693original
atctccgggattgtgagttctcggcttttttttatttaaaaactgtttttatacttgaa pCF693syngenic
atctccgggattgtgagttctcggcttttttttatttaaaaactgtttttatacttgaa
************************************************************ pCF693original
aaaaacagctctgctcatgcctgtaagctcacaaaattctttcaccgttgattttgaatg

-continued pCF693syngenic
aaaaacagctctgctcatgcctgtaagctcacaaaattctttcaccgttgattttgaatg
************************************************************ pCF693original
acattctaaaaatgtaaaaacggcatctctatatgactttctgccattgccatcgcgcca pCF693syngenic
acattctaaaaatgtaaaaacggcatctctatatgactttctgccattgccatcgcgcca
************************************************************ pCF693original
attcgtatcatcatatttgtctttaatagcttggatggctctagctccctctaaatgttg pCF693syngenic
attctatcatcatatttgtctttaatagcttggatggctctagctccctctaaatgttg
************************************************************ pCF693original
tttttttttctcccgttacgcttatttgcttttatttcaataccggacaatttagaaat pCF693syngenic
tttttgttttctcccgttacgcttatttgcttttatttcaataccggacaatttagaaat
************************************************************ pCF693original
ctcatctctaggaaaagacctataacattcctgatacatttctaaagcactctcaatatc pCF693syngenic
ctcatctctaggaaaagacctataacattcctgatacatttctaaagcactctcaatatc
************************************************************ pCF693original
ataatctgtaaacggttcatcgggattttatcattcaagtaattctgaaaagaataggc pCF693syngenic
ataatctgtaaacggttcatcgggattttatcattcaagtaattctgaaaagaataggc
************************************************************ pCF693original
atcttttttcaactcatcaaaatcaataccgcatttaaccgcataaaccgtcaaacacat pCF693syngenic
atcttttttcaactcatcaaaatcaataccgcatttaaccgcataaaccgtcaaacacat
************************************************************ pCF693original
tataaaaaaataccttatgatgatatacaatgcctgtaacttgccttttccaccaatcata pCF693syngenic
tataaaaaaataccttatgatgatatacaatgcctgtaacttgccttttccaccaatcata
************************************************************ pCF693original
caaagcacgtttacaagtccattctttttttttcgcggccaagttctatacgctgatgata pCF693syngenic
caaagcacgtttacaagtccattctttttttttcgcggccaagttctatacgctgatgata
************************************************************ pCF693original
ccaatccggatatttcttttttgcttcctcaagtgttaattttgaatgataaaaagtatc pCF693syngenic
ccaatccggatatttcttttttgcttcctcaagtgttaattttgaatgataaaaagtatc
************************************************************ pCF693original
tgttattcgattttcaggagcaacaaacctggataagtaatcaagagtcacttttcgcc pCF693syngenic
tgttattcgattttcaggagcaacaaacctggataagtaatcaagagtcacttttcgcc
************************************************************ pCF693original
tgttttatgggcaagaatcgtatagccgcgttttgacccactaccaacaagcctaaatcc pCF693syngenic
tgttttatgggcaagaatcgtatagccgcgttttgacccactaccaacaagcctaaatcc
************************************************************

-continued pCF693original
ttgatttatgccttgaaactgccgttgttttagtctggatgtatcacgattccatagttt pCF693syngenic
ttgatttatgccttgaaactgccgCtgttttagtctggatgtatcacgattccatagttt
                                                 **********************
********************************** pCF693original
ttctgtaagagcgtattttaattttttgagttgtctttgaatatttggatagagagggat pCF693syngenic
ttctgtaagagcgtattttaattttttgagttgtctttgaatatttggatagagagggat
************************************************************ pCF693original
aggattttcaaataaataatataaatgtacaccgtttccggaattaacaacataagtagg pCF693syngenic
aggattttcaaataaataatataaatgtacaccgtttccggaattaacaacataagtagg
************************************************************ pCF693original
ggtaggcaagcgctgatagttaccaccagggaaaggtttatcatatgcataaaaatacca pCF693syngenic
ggtaggcaagcgctgatagttaccaccagggaaaggtttatcatatgcataaaaatacca
************************************************************ pCF693original
cgtaaaaagcagctccaactctttcgccccaacctcatctaaatcaaaaacaagagcaaa pCF693syngenic
cgtaaaaagcagctccaactctttcgccccaacctcatctaaatcaaaaacaagagcaaa
************************************************************ pCF693original
tagttccctagcatttgctaaagtcctattttcccaaaatatgaataggagacataaa pCF693syngenic
tagttccctagcatttgctaaagtcctattttcccaaaatatgaataggagacataaa
************************************************************ pCF693original
ggcacaatcattacgagtatgctcccaaatctccgaatggtcatcaaaaaccatacgcgt pCF693syngenic
ggcacaatcattacgagtatgctcccaaatctccgaatggtcatcaaaaaccatacgcgt
************************************************************ pCF693original
acgttttttttcttctgaagtcgtatacaccaaaaaaccattacctttattttttttgg pCF693syngenic
acgttttttttcttctgaagtcgtatacaccaaaaaaccattacctttattttttttgg
************************************************************ pCF693original
ataatcaactaagaaccccattctttcctcaaagctgccaaaaggaaaaacatctctata pCF693syngenic
ataatcaactaagaaccccattctttcctcaaagctgccaaaaggaaaaacatctctata
************************************************************ pCF693original
aaaatctggagcataaactattttaaaatcaaagtcaattttttgtttagcagtcttaag pCF693syngenic
aaaatctggagcataaactattttaaaatcaaagtcaattttttgtttagcagtcttaag
************************************************************ pCF693original
aaaccactcctctttttcaaaaaacaagtcactcatactaagcatattataccgtagggg pCF693syngenic
aaaccactcctctttttcaaaaaacaagtcactcatactaagcatattataccgtagggg
************************************************************ pCF693original
gcgtatattatcaatacattaaatagacttcatgcataaatcaaatgtcaaatcactggt

-continued

```
pCF693syngenic
gcgtatattatcaatacattaaatagacttcatgcataaataaaatgtcaaatcactggt
************************************************************ pCF693original
tatatttctaagcacttcaacatcataggggggcgtatattatcaatatataaatggaaaa pCF693syngenic
tatatttctaagcacttcaacatcataggggggcgtatattatcaatatataaatggaaaa
************************************************************ pCF693original
agcacagacatactttcctcgttatcacacaataatcaaactcttagatttggccgttct pCF693syngenic
agcaGagacatactttAAtcgttatcacacaataatcaaactcttagatttggccgttct
          ****
*********. .******************************************* pCF693original
tataagctttcatcaagaattcatttacttctgattgccagcgcttaccttttgatcgaa pCF693syngenic
tataagctttcatcaagaattcatttacttctgattgccagcgcttaccttttgatcgaa
************************************************************ pCF693original
aatgttctaacaagactttattaaaacgaatagagacctgttcttttacaggtttaaaat pCF693syngenic
aatgttctaacaagactttattaaaacgaatagagacctgttcttttacaggtttaaaat
************************************************************ pCF693original
atttctcatttccaaaataaaaaccgtccaagctatttatttccggtatttcagatgtat pCF693syngenic
atttctcatttccaaaataaaaaccgtccaagctatttatttccggtatttcagatgtat
************************************************************ pCF693original
ctattagctcatccggaatcgcatttctttcacattcagccattatttgcgagatattta pCF693syngenic
ctattagctcatccggaatcgcattttttcacattcagccattatttgcgagatattta
************************************************************ pCF693original
attttttcataatacatttcccttcccgtttcaacgcaggacgcgccgatataattctt pCF693syngenic
attttttcataatacatttcTctttcccgtttcaacgcaggacgcgccgatataattctt
                   *******************
**************************************** pCF693original
tttttgccattttcggcgtataaacaacaaaaacaaccaactgacttttgactcttcca pCF693syngenic
tttttqccattttcggcgtataaacaacaaaaacaaccaactgacttttgactctGcca
********************************************** * pCF693original
agaacttgatagcgttcttcttctagcgttgaatgagttacatcatacttttccagataa pCF693syngenic
agaacttgatagcgttcttcttctagcgttgaatgagttacatcatacttttccagataa
************************************************************ pCF693original
aatgggtcatcaaaaacttgttgagcttcctcgaaagttaaacctgcatgcttttttta pCF693syngenic
aatgggtcatcaaaaacttgttgagcttcctcgaaagttaaacctgcatgcttttttta
************************************************************ pCF693original
ttcaattgagcctttgataaatgccattctgtaacatcattattcatcgtaaaattgtat
```

-continued

```
pCF693syngenic
ttcaattgagcctttgataaatgccattctgtaacatcattattcatcgtaaaattgtat
************************************************************ pCF693original
cacaaaattgtattttttgtaaattacataattactatcacctttcgaaatctatagattt pCF693syngenic
cacaaaattgtattttttgtaaattacataattactatcacctttcgaaatctatagattt
************************************************************ pCF693original
ctcacgtgttttttgtattcattgtttcatgtttggctttatcggaccaacttttaaaatt pCF693syngenic
ctcacgtgttttttgtattcattgtttcatgtttggctttatcAgaccaacttttaaaatt
**************************************. **************** pCF693original
ctcattttgcaactttgttgcaagatttattaactgtttaggactagcactttcccattg pCF693syngenic
ctcattttgcaactttgttgcaagatttattaactgtttaggactagcactttcccattg
************************************************************ pCF693original
atttactttctccatctctctcttttaaatcgctctccaaggcctctaaacgcctctgtac pCF693syngenic
atttactttctccatctctctcttttaaatcgctctccaaggcctctaaacgcctctgtac
************************************************************ pCF693original
ggcgtttagattacttttttagtgttaaattatccctactcaattctaataccttttcttc pCF693syngenic
ggcgtttagattacttttttagtgttaaattatccctactcaattctaataccttttcttc
************************************************************ pCF693original
gtgtttttgaagcagtggtaaaattttagctttgtaacgtacagaatactgctcaaaact pCF693syngenic
gtgtttttgaagcagtggtaaaattttagctttgtaacgtacagaatactgctcaaaact
************************************************************ pCF693original
ttctaacatttttttttgcaggcggctctatagctttatccagctgttcaagcttggtata pCF693syngenic
ttctaacatttttttttgcaggcggctctatagctttatccagctgttcaagcttggtata
************************************************************ pCF693original
aaactgttttacggtctgatgtcgtgctttagagcctttttacacctcttttccaacccgaa pCF693syngenic
aaactgttttacggtctgatgtcgtgctttagagcctttttacacctcttttccaacccgaa
************************************************************ pCF693original
tttttttgccaacttgctcaaaaaaactatcctgcatggatccgtctctggagctgtaata pCF693syngenic
tttttttgccaacttgctcaaaaaaactatcctgcatggatccgtctctggagctgtaata
************************************************************ pCF693original
taaaaaccttcttcaactaacggggcaggttagtgacattagaaaaccgactgtaaaaag pCF693syngenic
taaaaaccttcttcaactaacggggcaggttagtgacattagaaaaccgactgtaaaaag
************************************************************ pCF693original
tacagtcggcattatctcatattataaaagccagtcattaggcctatctgacaattcctg pCF693syngenic
tacagtcggcattatctcatattataaaagccagtcattaggcctatctgacaattcctg
************************************************************
```

```
pCF693original
aatagagttcataaacaatcctgcatgataaccatcacaaacagaatgatgtacctgtaa pCF693syngenic
aatagagttcataaacaatcctgcatgataaccatcacaaacTgaatgatgtacTtgtaa
*****************************************:******.*** pCF693original
agatagcggtaaatatattgaattacctttattaatgaattttcctgctgtaataatggg pCF693syngenic
agatagcggtaaatatattgaattacctttattaatgaattttcctgctgtaataatggg
************************************************************ pCF693original
tagaaggtaattactattattattgatatttaagttaaacccagtaaatgaagtccatgg pCF693syngenic
tagaaggtaattactattattattgatatttaagttaaacccagtaaatgaagtccatgg
************************************************************ pCF693original
aataatagaaagagaaaaagcattttcaggtataggtgttttgggaaacaatttccccga pCF693syngenic
aataatagaaagagaaaaagcattttcaggtataggtgttttgggaaacaatttccccga
************************************************************ pCF693original
accattatatttctctacatcagaaaggtataaatcataaaactctttgaagtcattctt pCF693syngenic
accattatatttctctacatcagaaaggtataaatcataaaactctttgaagtcattctt
************************************************************ pCF693original
tacaggagtccaaataccagagaatgttttagatacaccatcaaaaattgtataaagtgg pCF693syngenic
tacaggagtccaaataccagagaatgttttagatacaccatcaaaaattgtataaagtgg
************************************************************ pCF693original
ctctaacttatcccaataacctaactctccgtcgctattgtaaccagttctaaaagctgt pCF693syngenic
ctctaacttatcccaataacctaactctccgtcgctattgtaaccagttctaaaagctgt
************************************************************ pCF693original
atttgagtttatcacccttgtcactaagaaaataaatgcagggtaaaatttatatccttc pCF693syngenic
atttgagtttatcacccttgtcactaagaaaataaatgcagggtaaaatttatatccttc
************************************************************ pCF693original
ttgttttatgtttcggtataaaacactaatatcaatttctgtggttatactaaaagtcgt pCF693syngenic
ttgttttatgtttcggtataaaacactaatatcaatttctgtggttatactaaaagtcgt
************************************************************ pCF693original
ttttggttcaaataatgattaaatatctcttttctcttccaattgtctaaatcaatttt pCF693syngenic
ttgttggttcaaataatgattaaatatctctttTCGcttccaattgtctaaatcaatttt
                                 ***********************
*********************** pCF693original
attaaagttcatttgatatgcctcctaaattttttatctaaagtgaatttaggaggcttac pCF693syngenic
attaaagttcatttgatatgcctcctaaattttttatctaaagtgaatttaggaggcttac
************************************************************ pCF693original
ttgtctgctttcttcattagaatcaatcctttttttaaaagtcaatgacggatccggggag
```

```
pCF693syngenic
ttgtctgctttcttcattagaatcaatccttttttaaaagtcaatgacggatccggggag
************************************************************ pCF693original
cggccgccagtgtgatggatatctgcagaattccagcacactggcggccgttactagtga pCF693syngenic
cggccgccagtgtgatggatatctgcagaattccagcacactggcggccgttactagtga
************************************************************ pCF693original
acctcctatacattgatcctatgttacttcaataaattttcggcttattttttaaggcggg pCF693syngenic
acctcctatacattgatcctatgttacttcaataaattttcggcttattttttaaggcggg
************************************************************ pCF693original
tttaggaaaaaagtctatacaagctttaaattttttaaaggacgccccaagtttattggta pCF693syngenic
tttaggaaaaaagtctatacaagctttaaattttttaaaggacgccccaagtttattggta
************************************************************ pCF693original
ccaagcttgatgcaggcatgcaagcttggcgtaatcatggtcatagctgtttcctgtgtg pCF693syngenic
ccaagcttgatgcaATcatgcaagcttggcgtaatcatggtcatagctgtttcctgtgtg
              **************
************************************************ pCF693original
aaattgttatccgctcacaattccacacaacatacgagccggaagcataaag

Current methods for transforming *S. aureus* are challenging, time consuming and require ad hoc construction of new Plasmid Artificial Modification (PAM) hosts for each new strain. The exact genetic loci for most Restriction Modification (RM) systems (and therefore methyltransferase enzymes) are not well defined and as such cannot be introduced in *E. coli* PAM hosts. Also, some methyltransferase enzymes are difficult to clone functionally in *E. coli* due to differences in promoter structure, GC content, codon usage, and toxicity. In addition, there is incomplete methylation of PAM plasmids by recombinant methyltransferase enzymes within *E. coli* PAM host. Multiple and layered methyl signatures become difficult to recapitulate within a single *E. coli* PAM host: Many bacteria have multiple RM systems which would require multiple methyltransferase genes to be cloned, and to function correctly, within a single *E. coli* host, which is impractical. Accordingly, a more efficient, reliable, low cost, and quick method for transforming *S. aureus* is required.

The SyngenicDNA method was used successfully to overcome the transformation barrier in *Staphylococcus aureus* JE2 USA300. In a first step, PacBio™ SMRT sequencing was used to identify the methylated motifs present in the desired transformation host, *Staphylococcus aureus* JE2 USA300 (FIG. 10). This sequence and methylome data was subsequently processed through the publicly available Restriction Enzyme Database (REBASE) (FIG. 11A and FIG. 11B). The genome was also screened for the presence of Clustered regularly interspaced short palindromic repeats (CRISPRs) using a combination of CRISPRFinder, CRISPRdetect, and CRISPROne (omics.informatics.indiana.edu/CRISPRone) while protospacer targets were analyzed using the CRISPRTarget server.

The SyngenicDNA method identified that the *S. aureus* JE2 genetic barriers targeted the DNA sequences -CCAYNNNNNNTGT-(SEQ ID NO: 11) and -AGGNNNNNGAT-(SEQ ID NO:12) (the modified base within each motif is shown in bold, while the modified base on the complementary strand is underlined. (N=any base, Y=C or T) Additionally, REBASE analysis revealed that *S. aureus* JE2 contains a Type IV Methyl-directed RM system, which recognizes and targets the methylated motif SCNGS (the modified base is shown in bold N=any base, S=G or C). No CRISPR systems were identified.

Figure 12:
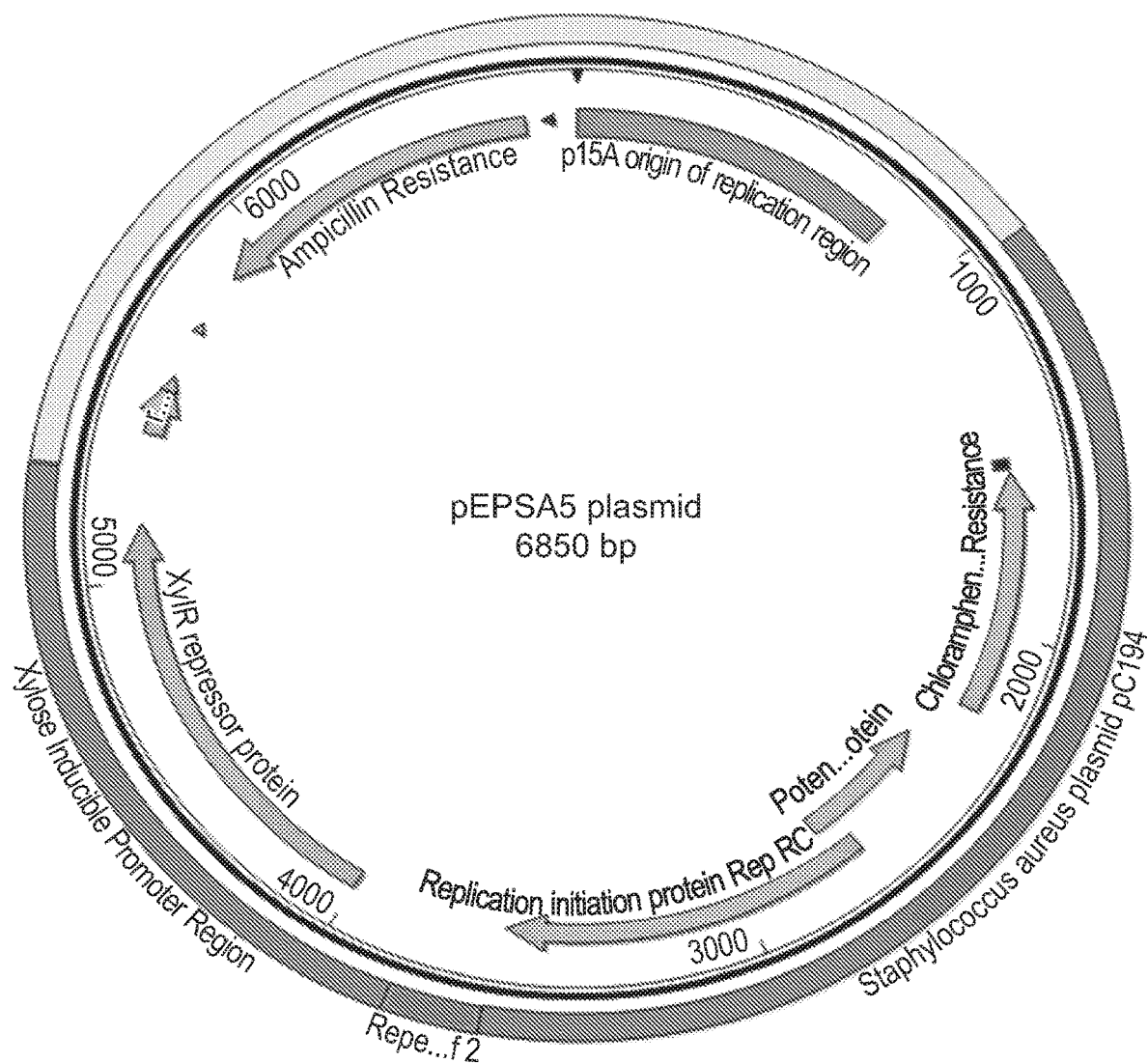
FIG. 12 provides an image of the pEPSA5 plasmid map.

Next, a plasmid was selected that with demonstrable functionality previously, called pEPSA5, for application to *S. aureus* JE2. The DNA sequence (6850 bp) of this plasmid was determined using commercial plasmid DNA sequencing. The plasmid map and annotation of the pEPSA5 plasmid was performed in-silico using a combination of publicly and commercially available tools (Plasmapper, Basic Local Alignment Search Tool (BLAST) analysis (blast.ncbi.nlm.nih.gov/Blast.cgi), and the bioinformatic suite DNAstar Lasergene (www.dnastar.com/t-allproducts.aspx). The plasmid pEPSA5 (FIG. 12) is an *S. aureus/E. coli* shuttle vector that contains elements to confer autonomous replication and chloramphenicol resistance in *S. aureus* (dark grey, outer box). Also included are elements of the multiple cloning site, rrnB T1T2 terminators and the ampicillin resistance gene of the plasmid pLEX5BA and the low copy number p15a origin for autonomous replication in *E. coli* (light grey, outer box). Upstream of the multiple cloning site and terminators is a Gram-positive optimized bacteriophage T5 PN25 promoter in context with the operator sequence for the *Staphylococcus xylosis* XylR repressor protein. Genes are indicated by arrows. The P15 origin or replication is also shown near the ampicillin resistance gene.

Figure 13:
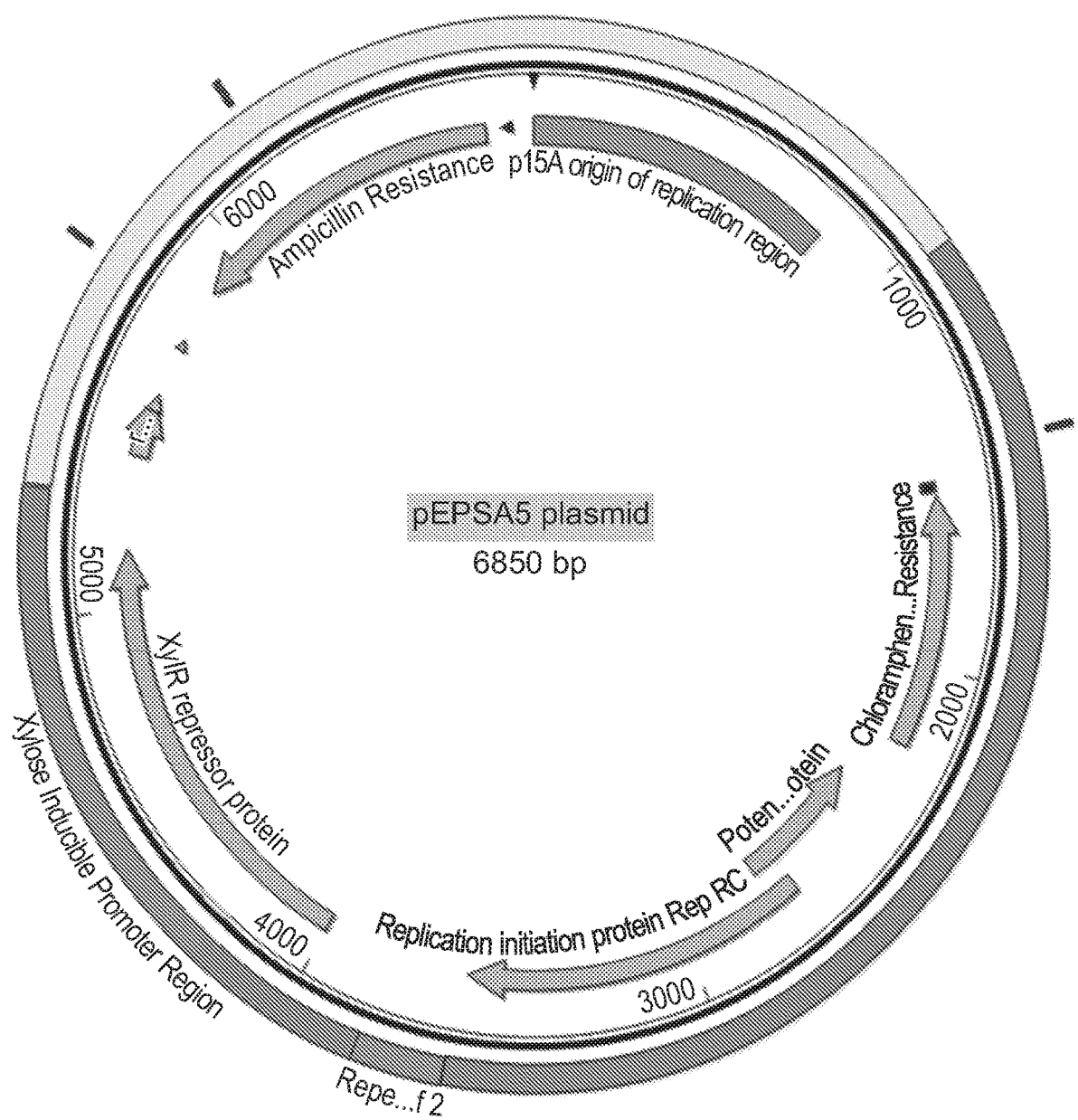
FIG. 13 provides an image of the pEPSA5 plasmid map with *S. aureus* JE2 genetic barriers target motifs highlighted in boxes.

Using the information in Step 1 and Step 2, the pEPSA5 polynucleotide sequence was screened for the presence of *S. aureus* JE2 genetic barriers target motifs (namely—CCANNNNNTGT-(SEQ ID NO: 11) and -AGGNNNNN-GAT-(SEQ ID NO:12)). It was determined that there were a total of three target motifs present in (1× CCANNNNNTGT (SEQ ID NO: 11) and 2× AGGNNNNNGAT (SEQ ID NO:12) sites. (FIG. 13: outer boxes, and bolded sequence below):

DNA Sequence of pEPSA5 Plasmid with *S. aureus* JE2 Genetic Barriers Target Motifs Highlighted (SEQ ID NO: 13)

ggcggccgcactggcttactatgttggcactgatgagggtgtcagtgaa gtgcttcatgtggcaggagaaaaaggctgcaccggtgcgtcagcagaa tatgtgatacaggatatattccgcttcctcgctcactgactcgctacgc tcggtcgttcgactgcggcgagcggaaatggcttacgaacgggggaga tttcctggaagatgccaggaagatacttaacagggaagtgagagggccg cggcaaagccgttttccataggctccgcccccctgacaagcatcacga aatctgacgctcaaatcagtggtggcgaaacccgacaggactataaaga taccaggcgtttccccctggcggctccctcgtgcgctctcctgttcctg cctttcggtttaccggtgtcattccgctgttatggccgcgtttgtctca ttccacgcctgacactcagttccgggtaggcagttcgctccaagctgga ctgtatgcacgaaccccccgttcagtccgaccgctgcgccttatccggt aactatcgtcttgagtccaacccggaaagacatgcaaaagcaccactgg cagcagccactggtaattgatttagaggagttagtcttgaagtcatgcg ccggttaaggctaaactgaaaggacaagttttggtgactgcgctcctcc aagccagttacctcggttcaaagagttggtagctcagagaaccttcgaa aaaccgccctgcaaggcggttttttcgttttcagagcaagagattacgc gcagaccaaaacgatctcaagaagatcatcttatgcggccgcttctttc ctgcgttatccctgattctgtggataaccgtattaccgcctttgagtg agctgataccgctcgccgcagccgaacgaccgagcgcagcgagtcagtg agcgaggaagcggaagagcgcctgatgcggtattttctccttacgcatc tgtgcggtatttcacaccgcataggaagatccctcgacctgcaggcatg caagcttctgtaggttttaggcataaaactatatgatttaccctaaa tctttaaaatgccccttaaaattcaaaataaaggcatttaaaatttaaa tatttcttgtgataaagtttgttaaaaaggagtggttttatgactgtta tgtggttatcgattataggtatgtggttttgtattggaatggcattttt tgctatcaaggttattaaaaataaaaattagaccacgcatttatgccga gaaaatttattgtgcgttgagaagaacccttaactaaacttgcagacga atgtcggcatagcgtgagctattaagccgaccattcgacaagttttggg attgttaagggttccgaggctcaacgtcaataaagcaattggaataaag aagcgaaaaggagaagtcggttcagaaaaagaaggatatggatctgga gctgtaatataaaaaccttcttcaactaacggggcaggttagtgacatt agaaaaccgactgtaaaaagtacagtcggcattatctcatattataaaa gccagtcattaggcctatctgacaattcctgaatagagttcataaacaa -continued

```
tcctgcatgataaccatcacaaacagaatgatgtacctgtaaagatagc ggtaaatatattgaattacctttattaatgaattttcctgctgtaataa tgggtagaaggtaattactattattattgatatttaagttaaacccagt aaatgaagtccatggaataatagaaagagaaaaagcattttcaggtata ggtgttttgggaaacaatttccccgaaccattatatttctctacatcag aaaggtataaatcataaaactctttgaagtcattctttacaggagtcca aataccagagaatgttttagatacaccatcaaaaattgtataaagtggc tctaacttatcccaataacctaactctccgtcgctattgtaaccagttc taaaagctgtatttgagtttatcacccttgtcactaagaaaataaatgc agggtaaaatttatatccttcttgttttatgtttcggtataaaacacta atatcaatttctgtggttatactaaaagtcgtttgttggttcaaataat gattaaatatctcttttctcttccaattgtctaaatcaattttattaaa gttcatttgatatgcctcctaaattttatctaaagtgaatttaggagg cttacttgtctgctttcttcattagaatcaatcctttttaaagtcaa tattactgtaacataaatatatattttaaaaatatcccactttatccaa ttttcgtttgttgaactaatgggtgctttagttgaagaataaaagacca cattaaaaaatgtggtctttgtgtttttttaaaggatttgagcgtagc gaaaaatcctttctttcttatcttgataataagggtaactattgccgg cgaggctagttacccttaagttattggtatgactggttttaagcgcaaa aaaagttgcttttcgtacctattaatgtatcgttttaaatgaatagta aaaaacatacatagaaaggggaaaaagcaacttttttttattgtcatagt ttgtgaaaactaagttgttttatgtgttataacatggaaaagtatact gagaaaaaacaaagaaatcaagtatttcagaaatttattaaacgtcata ttggagagaatcaaatggatttagttgaagattgcaatacatttctgtc ttttgtagctgataaaactttagaaaaacagaaattatataaagctaat tcttgtaaaaatcgattttgtcctgtctgtgcttggagaaaagctagaa aagatgcattgggtttatctttgatgatgcaatatattaagcagcaaga gaaaaaggagtttatcttttttaactttgactacacctaatgtaatgagt gatgaattagaaaatgaaataaaacgttataataattcttttagaaaac ttataaagagaaaaaagtaggtagtgttataaagggatatgttcgtaa gttagagattacatataataaaaaagagatgattataatcctcattttt catgtgttaattgcagtaaataaatcgtatttcacagataaaagatatt atattagccaacaagaatggttagatttatggcgtgatgtaacgggcat ttcagaaataacacaagttcaagttcaaaaaataagacaaaataataat aaagaattatatgaaatggctaagtattctggtaaagatagtgattatt taataaatcaaaaagtctttgatgcattttataaatcacttaaaggtaa acaggtattagtttattcaggattattttaaagaggctaaaaagaaatta aaaaatggggatttagattacttaaaagaaattgatccaaccgaatata tctatcaaatttttttatatttggaaacaaaaagagtatttagctagtga actttatgacttaacagaacaagaaaaaagagaaattaatcacaaaatg atagacgaaatcgaggaagaacaataacaaaatataagtgctaacagtc gtctgcaagtttagttaagggttcttctcaacgcacaataaattttctc ggcataaatgcgtggtctaattttttatttttaataaccttgatagcaaa aaatgccattccaatacaaaaccacatacctataatcgataaccacata acagtcataaaaccactccttttttaacaaactttatcacaagaaatatt ttggcattctacgactataacttaaatttatattttttactttataata tataattgattatagaataatgttgctcatatcgtttgccaacatctag tactcaaattacactatgttacacttggtaatattaaccgaacttcccc tgtccaaattagataagaggtaataataaatggaaaataattttatagt aaatgaaaatgagaagcgtgtattaaaacaaattttcaataacagcaat atttcacgaacacaaatatcgaagaatttagaacttaataaagctacta tttctaacattctgaacaacttaaaacacaagagtttagttaatgaagt aggagaaggtaatagtactaaaagtggtggacgaaagcctattttactc gaaattaaccaaaaatatggctactatatttctatggatttaacatatg attccgttgaattaatgtacaactactttgatgctactatattaaagca agattcctacgaattaaatgataaaaatgtaagcagtatattacaaatt ttaaaatcaatataaacgtctcagaaaaatatgatacgttatatgggt tacttggtatatctatatccatacacggtatcgttgacgatgagcaaaa cataatcaatcttccttttcataaaaatgagaaacgcacatttaccgat gaattaaagtcattcacaaatgttcctgtcgttatagaaaatgaagcaa atttatcagcgctatatgaaaaagtttatatattaattcaaacataaa taatttgattacttaagtattcacaagggtataggcgctggcatccta ataaataaaaaactttatcgtggctcaaatggagaggctggagagatag gtaagacattggttttggaatctataaataacaatgacaacaaatatta taaaatcgaagatatatgctcccaagacgctttaatacagaaaataaat aataggttgggcgtcacattgacgtttacagaactaatccaatattaca acgaaggaaattcaattgttgctcatgaaatttaaacaatttattaataa aatgacagttctgattcataatttgaatacacaatttaacccagacgct atttatattaactgtccttttaattaatgaattaccaaatattttaaatg aaattaaagagcaattctcctgttttttctcaaggcagtccagttcaatt acatttaactactaatgtaaaacaagctactttattgggtggcactta gcaataatgcaaaaaacattaaatataaataacattcaaatgaattatta aataattacagcagtctgagttataaaatagatatctcggaccgtcata aaaaatttatttgctttcaggaaaattttctgtataatagattcaagt tagtttgtttattaaattaaccaactaaaatgtagaattcgagctcggt acccggggatcctctagagtcgacctgcagccaagcttgggcttttcag cctgatacagattaaatcagaacgcagaagcggtctgataaaacagaat ttgcctggcggcagtagcgcggtggtcccacctgaccccatgccgaact cagaagtgaaacgccgtagcgccgatggtagtgtggggtctccccatgc gagagtagggaactgccaggcatcaaataaaacgaaaggctcagtcgaa agactgggcctttcgttttatctgttgtttgtcggtgaacgctctcctg
```

-continued

```
agtaggacaaatccgccgggagcggatttgaacgttgcgaagcaacggc ccggagggtggcgggcaggacgcccgccataaactgccaggcatcaaat taagcagaaggccatcctgacggatggccttttgcgtttctacaaact cttttgtttattttctaaatacattcaaatatgtatccgctcatcccc atcctatcgatgataagctgtcaaacatgagaattaaatcaatctaaag tatatatgagtaaacttggtctgacagttaccaatgcttaatcagtgag gcacctatctcagcgatctgtctatttcgttcatccatagttgcctgac tccccgtcgtgtagataactacgatacgggagggcttaccatctggccc cagtgctgcaatgataccgcgagacccacgctcaccggctccagattta tcagcaataaaccagccagccggaagggccgagcgcagaagtggtcctg caactttatccgcctccatccagtctattaattgttgcgggaagctag agtaagtagttcgccagttaatagtttgcgcaacgttgttgccattgct acaggcatcgtggtgtcacgctcgtcgtttggtatggcttcattcagct ccggttcccaacgatcaaggcgagttacatgatccccatgttgtgcaa aaaagcggttagctccttcggtcctccgatcgttgtcagaagtaagttg gccgcagtgttatcactcatggttatggcagcactgcataattctctta ctgtcatgccatccgtaagatgcttttctgtgactggtgagtactcaac caagtcattctgagaatagtgtatgcggcgaccgagttgctcttgcccg gcgtcaacacgggataataccgcgccacatagcagaactttaaaagtgc tcatcattggaaaacgctcttcggggcgaaaactctcaaggatcttacc gctgttgagatccagttcgatgtaaccactcgtgcacccaactgatct tcagcatcttttactttcaccagcgtttctgggtgagcaaaaacaggaa ggcaaaatgccgcaaaaaagggaataagggcgacacggaaatgttgaat actcatactcttccttttcaatattattgaagcatttatcagggttat tgtctcatgagcggatacatatttgaatgtatttagaaaaataaacaaa tagggttccgcgcacatttccccgaaaagtgccacct
```

Next, these target sequences were eliminated using either synonymous codon substitution (if target existed within an open reading frame) or single nucleotide polymorphism (if target existed outside of an open reading frame).

Site 1: CCANNNNNTGT (SEQ ID NO: 11)

In pEPSA5, only one of the three sites was present in an open reading frame, which existed within the ampicillin resistance cassette of the *E. coli* replicon. This site occurs at position 532-545 bp of the amp ORF. The target was eliminated from the modified DNA sequence (dark line, FIG. 14A) by synonymous changes adhering to the codon usage of *E. coli* (due to the target existing within the *E. coli* replicon), so that this did not alter the amino acid sequence of the protein.

Figure 15:
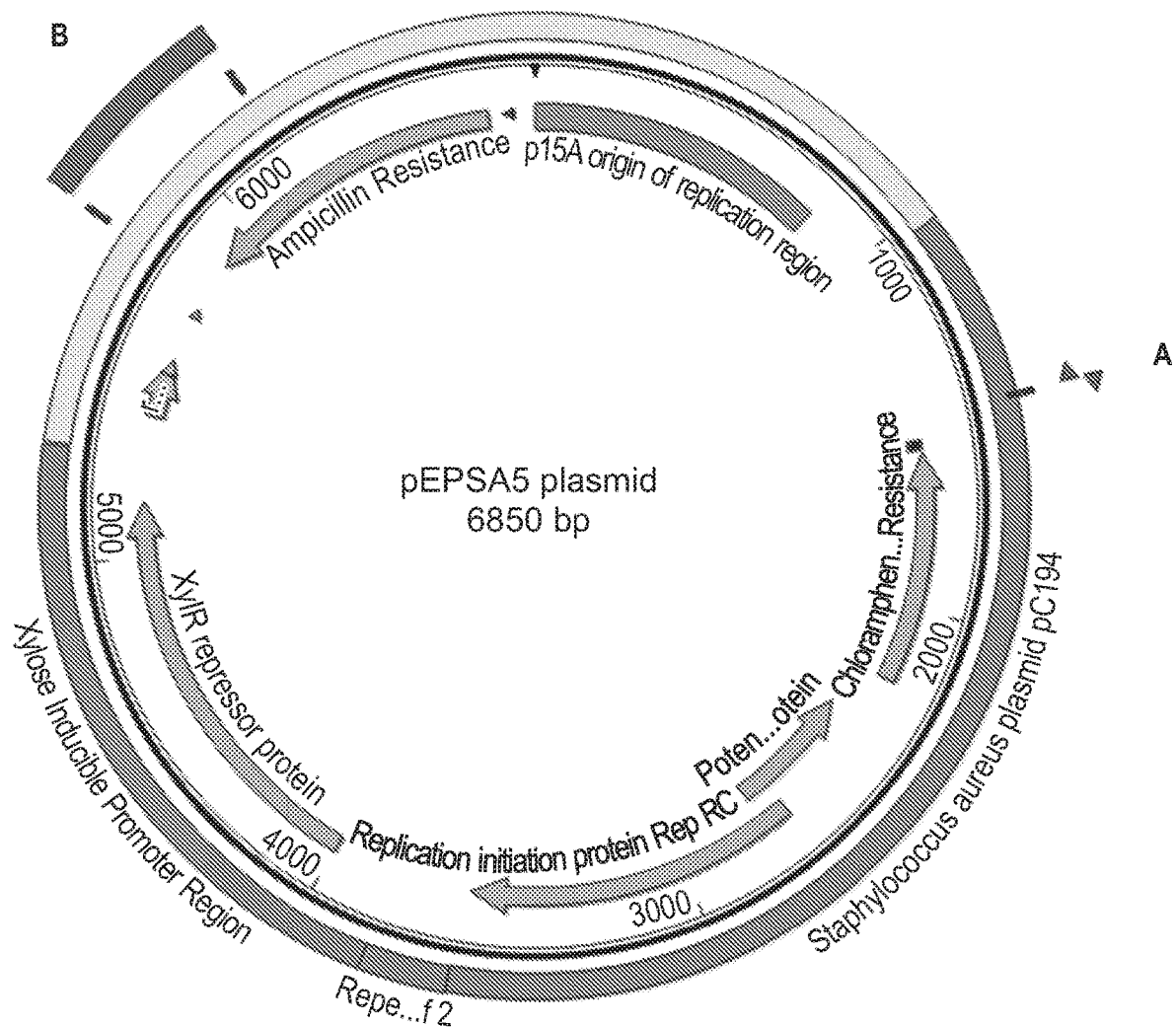
FIG. 15 provides an image of the pEPSA5 plasmid map with outer grey triangles (next to the letter A) indicating the location and direction of the specific primers used for site-specific mutagenesis of double-stranded plasmid DNA.

The introduced changes affect the 178th (ACC to ACT change/both code for Threonine) and 181st (CCT to CCA change/both code for Threonine) codons of the Ampicillin resistance gene. The change effectively eliminated the motif target without altering the amino acid sequence in-silico (FIG. 14A, FIG. 14B and FIG. 15).

Site 2 and 3: AGGNNNNNNGAT (SEQ ID NO: 12)

Both AGGNNNNNNGAT (SEQ ID NO:12) sites were present in the *E. coli* replicon portion of the plasmid but were not in ORFs. Therefore, single nucleotide polymorphisms were used to eliminate these targets in-silico. Site 2, with sequence 5'-aggatggggat-3' (SEQ ID NO: 14) was altered to 5'-aCgatgggCat-3' (SEQ ID NO: 15); Site 3, with sequence 5'-aggatatggat-3'(SEQ ID NO: 16) was altered to 5'-agCatatgCat-3' (SEQ ID NO: 17). The changes (indicated by uppercase letters) effectively eliminated the motif targets (bolded letters) from pEPSA5 in-silico. After creation of this modified polynucleotide sequence of pEPSA5 in-silico, the new host mimicking/syngenic plasmid, lacking all target motifs from *S. aureus* strain JE2 and now called pEPSA5-syngenic, was ready to be synthesized and constructed in-vitro.

There were relatively few changes which needed to be made in pEPSA5 to construct pEPSA5-syngenic. Therefore, the entire plasmid did not have to be synthesized de-novo. Instead, the changes were made to the original pEPSA5 DNA in-vitro. A splicing by overlap extension (SOEing) technique was used to remove one of three sites. A commercially available Site-Directed Mutagenesis Kit enabling rapid, site-specific mutagenesis of double-stranded plasmid DNA using specific DNA primers was used to introduce the change (FIG. 15, outer grey triangles, indicated by the letter A, showing the location and direction of these primers).

To change the remaining two sites, de-novo DNA synthesis of a 700 bp segment of DNA was used to replace a corresponding same sized fragment on pEPSA5. The de-novo synthetized piece of DNA was identical to corresponding fragment on pEPSA5 except for sites modified in Step 3 (FIG. 15B, outer grey box above target sites, indicated by the letter B). The assembly of this fragment to the plasmid was performed using the commercially available NEBuilder HiFi DNA Assembly Master Mix. This kit allowed for seamless assembly of multiple DNA fragments, regardless of fragment length or end compatibility, and was used to assemble the DNA fragments of pEPSA5-syngenic.

The assembled pEPSA5-syngenic was free from all Type I RM system targets identified within *Staphylococcus aureus* JE2 USA300. However, in Step 1, *Staphylococcus aureus* JE2 USA300 was identified as having a Type IV methyl directed restriction system which targets the cytosine residue on the motif SCNGS (the modified base is shown in bold N=any base, S=G or C) if it contains a methylation. As standard commercial *E. coli* cloning hosts contain a Dcm methyltransferase gene which adds a methyl group to the second cytosine in the sequence CCWGG (where W=A or T), it was determined that propagation of the pEPSA5-syngenic plasmid in standard *E. coli* cloning hosts would lead to reduction in transformation efficiency due to degradation of methylated SCNGS motifs.

Therefore, the pEPSA5-syngenic plasmid was propagated out in a commercially available methyl deficient *E. coli* cloning host (dam-/dcm- Competent *E. coli*). To transform *Staphylococcus aureus* JE2 USA300, the strain was first cultivated and made into competent cells. To provide insight into the effectiveness of the SyngenicDNA method, four different plasmids were used:

1) pEPSA5 propagated in *E. coli* that methylate's cytosine (Methyl+).
2) pEPSA5 propagated in *E. coli* that does not methylate cytosine (Methyl-)
3) pEPSA5-syngenic propagated in *E. coli* that methylates cytosines (Methyl+)
4) pEPSA5-syngenic propagated in *E. coli* that does not methylate cytosines (Methyl-)

Figure 16:
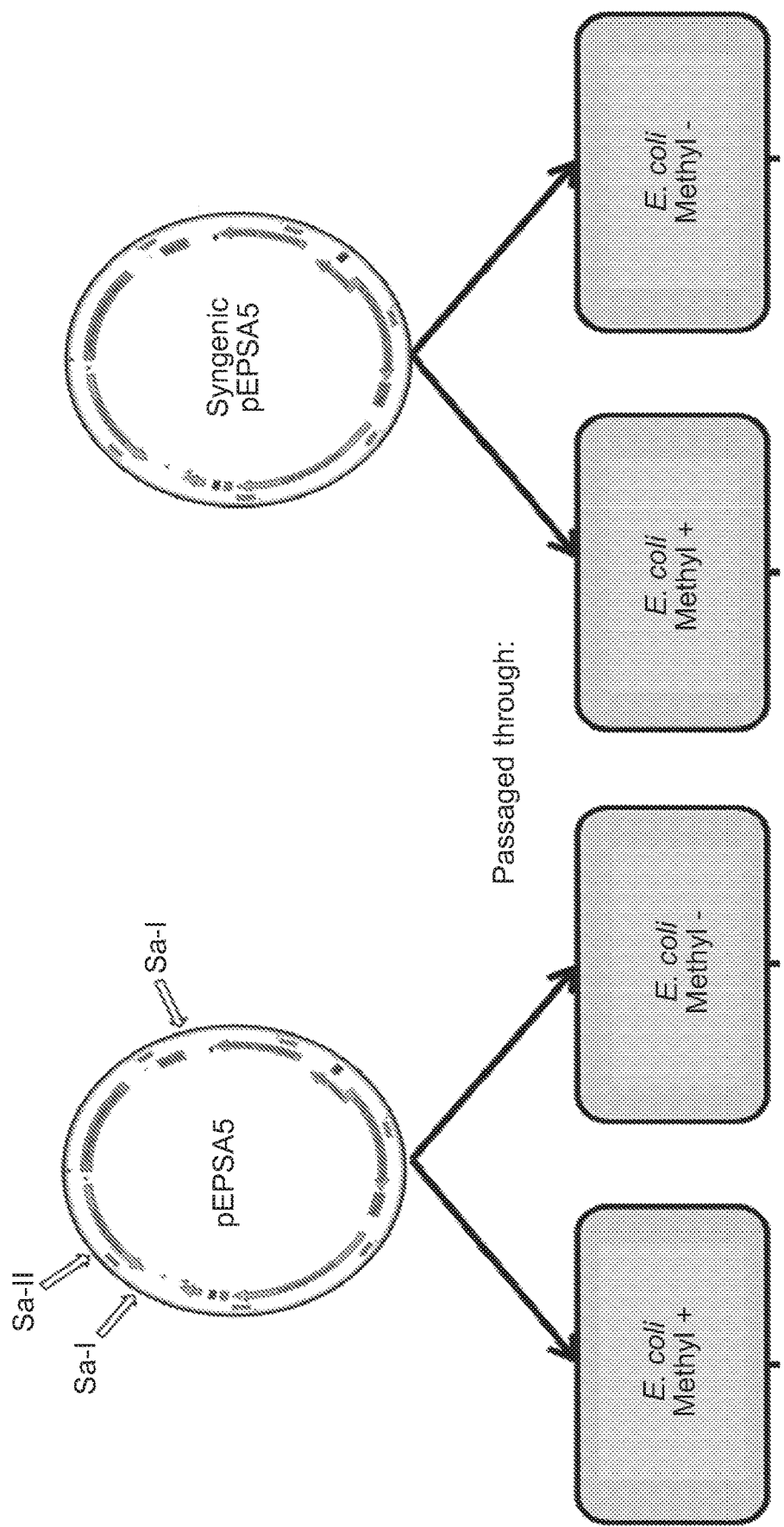
FIG. 16 shows an image of the SyngenicDNA method using the four different plasmids: (1) pEPSA5 propagated in *E. coli* that methylate's cytosine (Methyl+); (2) pEPSA5 propagated in *E. coli* that does not methylate cytosine (Methyl−); (3) pEPSA5-syngenic propagated in *E. coli* that methylates cytosines (Methyl+); and (4) pEPSA5-syngenic propagated in *E. coli* that does not methylate cytosines (Methyl−).
Figure 17:
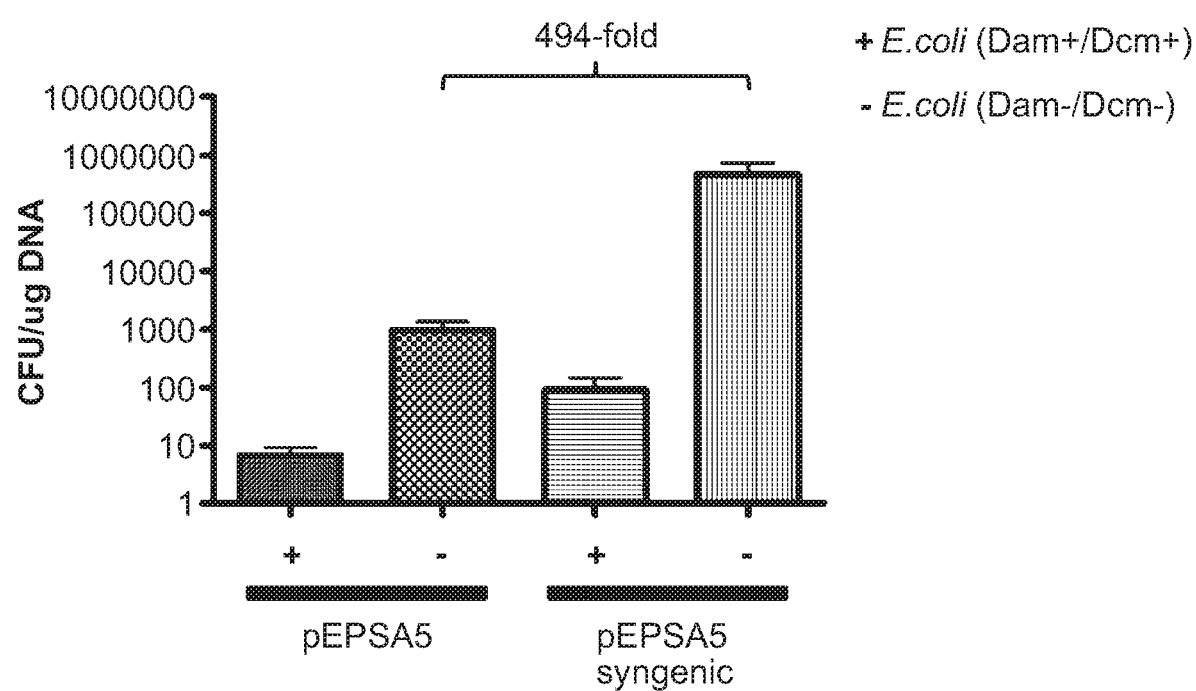
FIG. 17 is a bar graph showing the transformation efficiency of the syngenic DNA method applied to the pEPSA5 plasmid.

This strategy is detailed in FIG. 16. *Staphylococcus aureus* JE2 USA300 competent cells were transformed by electroporation and the transformation efficiency of each plasmid was compared with 1-microgram of DNA per reaction. We demonstrate a 494-fold increase in transformation efficiency when the syngenic DNA method is applied to the pEPSA5 plasmid (FIG. 17).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for obtaining a syngenic polynucleotide, the method comprising:
   (a) detecting, in silico, based on genomic sequences of a bacteria of interest and using epigenetic information of methylated DNA sequences of a polynucleotide sequence of the bacteria of interest, recognition sites for Restriction Modification (RM) systems and Clustered Regularly Interspaced Short Palindromic Repeat (CRISPR) systems in a heterologous polynucleotide sequence; and
   (b) modifying the heterologous polynucleotide sequence to alter a plurality of said recognition sites to no longer be recognition sites in the bacteria of interest, wherein the plurality of said recognition sites includes at least one RM system and at least one CRISPR system, and thereby obtaining by mutagenesis or de novo synthesis the syngenic polynucleotide having the recognition sites that are no longer recognitions sites in the bacteria of interest and that resists restriction endonuclease degradation and CRISPR degradation, when transformed into the bacteria of interest,
   wherein the bacteria of interest is selected from the group consisting of *Actinobacteria, Armatimonadetes, Aquificae, Bacteroidetes, Chlamydiae, Chloroflexi, Caldiserica, Chlorobi, Chrysiogenetes, Cyanobacteria, Deferribacteres, Deinococcus-Thermus, Dictyoglomi, Elusimicrobia Euryarchaeota, Firmicutes, Fusobacteria, Fibrobacteres, Gemmatimonadetes, Lentisphaerae, Nitrospirae, Planctomycetes, Proteobacteria, Spirochaetes*, SRI, *Synergistetes, Tenericutes*, TM7, *Thermodesulfobacteria, Thermomicrobia, Thermotojae*, and *Verrucomicrobia*.

2. The method of claim 1, wherein a coding region sequence of the heterologous polynucleotide sequence is modified by synonymous codon substitution.

3. The method of claim 1, wherein a noncoding region sequence of the heterologous polynucleotide sequence is modified by one or more single nucleotide polymorphisms.

4. The method of claim 1, wherein the syngenic polynucleotide is selected from the group consisting of a plasmid, replication origin, antibiotic resistance cassette, promoter, repressor, terminator, protein coding domain, transposon, operon, linear DNA knockout cassette and a bacterial genome.

5. The method of claim 1, wherein the syngenic polynucleotide is deoxyribonucleic acid (DNA) or ribonucleic acid (RNA).

6. The method of claim 1, wherein modifying the heterologous polynucleotide sequence is relative to a reference sequence.

7. The method of claim 1, wherein the genomic sequences of the bacteria of interest, epigenetic information of methylated DNA sequences of a polynucleotide sequence of the bacteria of interest, or both are identified by Single Molecule Real Time (SMRT) sequencing of the bacterial genome of the bacteria of interest.

8. The method of claim 1, wherein the syngenic polynucleotide is a replicative plasmid.

9. The method of claim 1, wherein the syngenic polynucleotide recapitulates the preferential codon bias of the bacteria of interest.

10. The method of claim 1, wherein methylations in the heterologous polynucleotide are modified via synonymous codon substitution using splicing by overlap extension (SOEing).

11. The method of claim 1, wherein methylations in the heterologous polynucleotide are modified via enzyme that methylates adenine residues.

12. The method of claim 1, wherein the bacteria of interest is a probiotic bacteria selected from the group consisting of any one or more of *Lactobacillus* species, *Lactococcus* species, *Bifidobacterium* species, *Entercoccus* species, *Streptococcus* species, *Pediococcus* species, *Leuconostoc* species, *Bacillus* species, and *Escherichia coli* species.

13. The method of claim 12, wherein the bacteria of interest is a probiotic bacteria selected from *Prevotella*.

14. The method of claim 13, wherein the bacteria of interest is *P. intermedia*.

15. The method of claim 1, further comprising detecting epigenetic information of methylated DNA sequences by detecting each methylation site in the polynucleotide sequence.

16. The method of claim 1, wherein modifying the heterologous polynucleotide sequence comprises altering all of said recognition sites to no longer be recognition sites in the bacteria of interest.

17. The method of claim 1, wherein the bacteria of interest is a gram positive bacteria selected from the group consisting of any one or more of *Pasteurella* species, *Staphylococci* species, and *Streptococcus* species.

18. The method of claim 1, wherein the bacteria of interest is a gram negative bacteria selected from the group consisting of any one or more of *Escherichia coli, Pseudomonas* species, and *Salmonella* species.

19. The method of claim 1, wherein the bacteria of interest is any one or more infectious bacteria selected from the group consisting or any one or more of *Borelia burgdorferi, Legionella pneumophilia, Mycobacteria* species, *Staphylococcus aureus, Neisseria gonorrheae, Nesseria meningitidis, Listeria monocytogenes, Streptococcus pyogenes, Streptococcus agalactiae, Streptococcus* viridians group, *Streptococcus faecalis, Streptococcus bovis, Streptococcus* anaerobic species, *Streptococcus pneumoniae, Enterococcus* species, *Haemophilus influenzae, Bacillus anthracis Corynebacerium diphtheriae*, other *Corynebacterium* species, *Enterobacter aerogenes, Klebsiella pneumoniae, Pasteurella multocida, Bacteroides* species, *Fusobacterium nucleatum, Streptobacillus moniliformis, Treponema pallidium, Treponema pertenue, Leptospira, Rickettsia*, and *Actinomyces israelli*.

* * * * *

SEQUENCE LISTING

```
<160> NUMBER OF SEQ ID NOS: 138

<210> SEQ ID NO 1
<211> LENGTH: 10
<212> TYPE: DNA
<213> ORGANISM: Prevotella intermedia
<220> FEATURE:
<221> NAME/KEY: modified_base
<222> LOCATION: (4)..(7)
<223> OTHER INFORMATION: a, c, t, g, unknown or other

<400> SEQUENCE: 1 gagnnnntac                                                            10

<210> SEQ ID NO 2
<211> LENGTH: 10
<212> TYPE: DNA
<213> ORGANISM: Prevotella intermedia
<220> FEATURE:
<221> NAME/KEY: modified_base
<222> LOCATION: (4)..(7)
<223> OTHER INFORMATION: a, c, t, g, unknown or other

<400> SEQUENCE: 2 gtannnnctc                                                            10

<210> SEQ ID NO 3
<211> LENGTH: 12
<212> TYPE: DNA
<213> ORGANISM: Prevotella intermedia
<220> FEATURE:
<221> NAME/KEY: modified_base
<222> LOCATION: (4)..(8)
<223> OTHER INFORMATION: a, c, t, g, unknown or other

<400> SEQUENCE: 3 agynnnnrt tc                                                          12

<210> SEQ ID NO 4
<211> LENGTH: 12
<212> TYPE: DNA
<213> ORGANISM: Prevotella intermedia
<220> FEATURE:
<221> NAME/KEY: modified_base
<222> LOCATION: (5)..(9)
<223> OTHER INFORMATION: a, c, t, g, unknown or other

<400> SEQUENCE: 4 gaaynnnnr ct                                                          12

<210> SEQ ID NO 5
<211> LENGTH: 12
<212> TYPE: DNA
<213> ORGANISM: Prevotella intermedia
```

-continued

```
<220> FEATURE:
<221> NAME/KEY: modified_base
<222> LOCATION: (4)..(9)
<223> OTHER INFORMATION: a, c, t, g, unknown or other

<400> SEQUENCE: 5
cagnnnnnnt tg                                                         12

<210> SEQ ID NO 6
<211> LENGTH: 12
<212> TYPE: DNA
<213> ORGANISM: Prevotella intermedia
<220> FEATURE:
<221> NAME/KEY: modified_base
<222> LOCATION: (4)..(9)
<223> OTHER INFORMATION: a, c, t, g, unknown or other

<400> SEQUENCE: 6
caannnnnnc tg                                                         12

<210> SEQ ID NO 7
<211> LENGTH: 14
<212> TYPE: DNA
<213> ORGANISM: Treponema denticola
<220> FEATURE:
<221> NAME/KEY: modified_base
<222> LOCATION: (4)..(10)
<223> OTHER INFORMATION: a, c, t, g, unknown or other

<400> SEQUENCE: 7
cagnnnnnnn tdcc                                                       14

<210> SEQ ID NO 8
<211> LENGTH: 13
<212> TYPE: DNA
<213> ORGANISM: Treponema denticola
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(10)
<223> OTHER INFORMATION: a, c, t, g, unknown or other

<400> SEQUENCE: 8
cnacnnnnnn ttc                                                        13

<210> SEQ ID NO 9
<211> LENGTH: 6320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
cttccgcttc tcgctcact gactcgctgc gctcggtcgt tcggctgcgg cgagcggtat       60
cagctcactc aaaggcggta atacggttat ccacagaatc aggggataac gcaggaaaga    120
acatgtgagc aaaaggccag caaaaggcca ggaaccgtaa aaaggccgcg ttgctggcgt    180
ttttccatag gctacgcccc cctgacgagc atcacaaaaa tcgacgctca agtcagaggt    240
ggcgaaaccc gacaggacta taaagatacc aggcgtttcc ccctggaagc tccctcgtgc    300
gctctcctgt tccgaccctg ccgcttaccg gatacctgtc cgcctttctc ccttcgggaa    360
gcgtggcgct ttctcatagc tcacgctgta ggtatctcag ttcggtgtag gtcgttcgct    420
```

```
ccaagctggg ctgtgtgcac gaaccccccg ttcagcccga ccgctgcgcc ttatccggta      480
actatcgtct tgagtccaac ccggtaagac acgacttatc gccactggca gcagccactg      540
gtaacaggat tagcagagcg aggtatgtag gcggtgctac agagttcttg aagtggtggc      600
ctaactacgg ctacactaga agaacagtat ttggtatctg cgctctgctg aagccagtta      660
ccttcggaaa aagagttggt agctcttgat ccggcaaaca aaccaccgct ggtagcggtg      720 gttttttgt ttgcaagcag cagattacgc gcagaaaaaa aggatctcaa gaagatcctt      780
tgatcttttc tacggggtct gacgctcagt ggaacgaaaa ctcacgttaa gggattttgg      840
tcatgagatt atcaaaaagg atcttcacct agatccttt cctcgagatc cgcgcgttta      900
atgaccagca cagtcgtgat ggcaaggtca gaatagcgct gaggtctgcc tcgtgaagaa      960
ggtgttgctg actcatacca ggcctgaatc gccccatcat ccagccagaa agtgagggag     1020
ccacggttga tgagagcttt gttgtaggtg gaccagttgg tgattttgaa cttttgcttt     1080
gccacggaac ggtctgcgtt gtcgggaaga tgcgtgatct gatccttcaa ctcagcaaaa     1140
gttcgattta ttcaacaaag ccacgttgtg tctcaaaatc tctgatgtta cattgcacaa     1200
gataaaaata tatcatcatg aacaataaaa ctgtctgctt acataaacag taatacaagg     1260
ggtgttatga gccatattca acgggaaacg tcttgctcga ggccgcgatt aaattccaac     1320
atggatgctg atttatatgg gtataaatgg gctcgcgata atgtcgggca atcaggtgcg     1380
acaatctatc gattgtatgg gaagcccgat gcgccagagt tgtttctgaa acatggcaaa     1440
ggtagcgttg ccaatgatgt tacagatgag atggtcagac taaactggct gacggaattt     1500
atgcctcttc cgaccatcaa gcattttatc cgtactcctg atgatgcatg gttactcacc     1560
actgcgatcc ccggaaaaac agcattccag gtattagaag aatatcctga ttcaggtgaa     1620
aatattgttg atgcgctggc agtgttcctg cgccggttgc attcgattcc tgtttgtaat     1680
tgtcctttta acagcgatcg cgtatttcgt ctcgctcagg cgcaatcacg aatgaataac     1740
ggtttggttg atgcgagtga ttttgatgac gagcgtaatg gctggcctgt tgaacaagtc     1800
tggaaagaaa tgcataaact tttgccattc tcaccggatt cagtcgtcac tcatggtgat     1860
ttctcacttg ataaccttat ttttgacgag gggaaattaa taggttgtat tgatgttgga     1920
cgagtcggaa tcgcagaccg ataccaggat cttgccatcc tatggaactg cctcggtgag     1980
ttttctcctt cattacagaa acggcttttt caaaaatatg gtattgataa tcctgatatg     2040
aataaattgc agtttcattt gatgctcgat gagtttttct aatcagaatt ggttaattgg     2100
ttgtaacact ggcagagcat tacgctgact tgacgggacg cggctttgt tgaataaatc      2160 gaacttttgc tgagttgaag gatctcgagg tgcaccatat gcggtgtgaa ataccgcaca     2220
gatgcgtaag agaaaatac cgcatcaggc gccattcgcc attcaggctg cctcggtacc      2280
cggggatccg caggggactg acatatttaa agctgagatt tatggttgcg gagaaattgt     2340
atctccggga ttgtgagttc tcggcttttt tttatttaaa aactgttttt tatacttgaa     2400
aaaaacagct ctgctcatgc ctgtaagctc acaaaattct ttcaccgttg attttgaatg     2460
acattctaaa aatgtaaaaa cggcatctct atatgacttt ctgccattgc catcgcgcca     2520
attcgtatca tcatatttgt ctttaatagc ttggatggct ctagctccct ctaaatgttg     2580
tttttgtttt ctcccgttac gcttatttgc tttatttca ataccggaca atttagaaat      2640
ctcatctcta ggaaaagacc tataacattc ctgatacatt tctaaagcac tctcaatatc     2700
ataatctgta aacggttcat cgggattttt atcattcaag taattctgaa agagaataggc    2760
```

```
atcttttttc aactcatcaa aatcaatacc gcatttaacc gcataaaccg tcaaacacat    2820
tataaaaaaa tacctatgat gatatacaat gcctgtaact tgccttttcc accaatcata    2880
caaagcacgt ttacaagtcc attctttttt ttcgcggcca agttctatac gctgatgata    2940
ccaatccgga tatttctttt ttgcttcctc aagtgttaat tttgaatgat aaaaagtatc    3000
tgttattcga ttttcaggag caacaaacct ggataagtaa tcaagagtca cttttttcgcc    3060 tgttttatgg gcaagaatcg tatagccgcg ttttgaccca ctaccaacaa gcctaaatcc    3120
ttgatttatg ccttgaaact gccgttgttt tagtctggat gtatcacgat tccatagttt    3180
ttctgtaaga gcgtatttta atttttttgag ttgtctttga atatttggat agagagggat    3240
aggattttca aataaataat ataaatgtac accgttccg gaattaacaa cataagtagg    3300
ggtaggcaag cgctgatagt taccaccagg gaaaggttta tcatatgcat aaaaatacca    3360
cgtaaaaagc agctccaact cttttcgcccc aacctcatct aaatcaaaaa caagagcaaa    3420
tagttcccta gcatttgcta aagtcctatt tttcccaaaa tatgaaatag gagacataaa    3480
ggcacaatca ttacgagtat gctcccaaat ctccgaatgg tcatcaaaaa ccatacgcgt    3540
acgttttttt tcttctgaag tcgtatacac caaaaaacca ttacctttat ttgttttttgg    3600 ataatcaact aagaaccca ttcttttcctc aaagctgcca aaaggaaaaa catctctata    3660
aaaatctgga gcataaacta ttttaaaatc aaagtcaaat ttttgtttag cagtcttaag    3720
aaaccactcc tctttttcaa aaacaagtc actcatacta agcatattat accgtagggg    3780
gcgtatatta tcaatacatt aaatagactt catgcataaa taaaatgtca aatcactggt    3840
tatatttcta agcacttcaa catcataggg ggcgtatatt atcaatatat aaatggaaaa    3900
agcacagaca tactttcctc gttatcacac aataatcaaa ctcttagatt tggccgttct    3960
tataagcttt catcaagaat tcatttactt ctgattgcca gcgcttacct tttgatcgaa    4020
aatgttctaa caagacttta ttaaaacgaa tagagacctg ttcttttaca ggtttaaaat    4080
atttctcatt tccaaaataa aaaccgtcca agctatttat ttccggtatt tcagatgtat    4140
ctattagctc atccggaatc gcatttcttt cacattcagc cattatttgc gagatattta    4200 atttttttcat aatacatttc ccttttcccgt ttcaacgcag gacgcgccga tataattctt    4260 ttttttgccat ttttcggcgt ataaacaaca aaaacaacca actgactttt gactcttcca    4320
agaacttgat agcgttcttc ttctagcgtt gaatgagtta catcatactt ttccagataa    4380
aatgggtcat caaaaacttg ttgagcttcc tcgaaagtta aacctgcatg cttttttttta    4440 ttcaattgag cctttgataa atgccattct gtaacatcat tattcatcgt aaaattgtat    4500
cacaaaattg tattttgta aattacataa ttactatcac cttttcgaaat ctatagattt    4560 ctcacgtgtt tttgtattca ttgtttcatg tttggcttta tcggaccaac ttttaaaatt    4620 ctcatttttgc aactttgttg caagatttat taactgttta ggactagcac tttcccattg    4680
atttactttc tccatctctc tctttaaatc gctctccaag gcctctaaac gcctctgtac    4740 ggcgttaga ttacttttta gtgttaaatt atccctactc aattctaata ccttttcttc    4800 gtgttttga agcagtggta aaattttagc tttgtaacgt acagaatact gctcaaaact    4860
ttctaacatt ttttttgcag gcggctctat agcttatcc agctgttcaa gcttggtata    4920
aaactgtttt acggtctgat gtcgtgcttt agagcctttt acacctcttt ccaacccgaa    4980
ttttttgcca acttgctcaa aaaaactatc ctgcatggat ccgtctctgg agctgtaata    5040
taaaaacctt cttcaactaa cggggcaggt tagtgacatt agaaaaccga ctgtaaaaag    5100
tacagtcggc attatctcat attataaaag ccagtcatta ggcctatctg acaattcctg    5160
```

-continued

| | |
|---|---|
| aatagagttc ataaacaatc ctgcatgata accatcacaa acagaatgat gtacctgtaa | 5220 |
| agatagcggt aaatatattg aattaccttt attaatgaat tttcctgctg taataatggg | 5280 |
| tagaaggtaa ttactattat tattgatatt taagttaaac ccagtaaatg aagtccatgg | 5340 |
| aataatagaa agagaaaaag cattttcagg tataggtgtt ttgggaaaca atttccccga | 5400 |
| accattatat ttctctacat cagaaaggta taaatcataa aactctttga agtcattctt | 5460 |
| tacaggagtc caaataccag agaatgtttt agatacacca tcaaaaattg tataaagtgg | 5520 |
| ctctaactta tcccaataac ctaactctcc gtcgctattg taaccagttc taaaagctgt | 5580 |
| atttgagttt atcacccttg tcactaagaa aataaatgca gggtaaaatt tatatccttc | 5640 |
| ttgttttatg tttcggtata aaacactaat atcaatttct gtggttatac taaaagtcgt | 5700 |
| ttgttggttc aaataatgat taaatatctc ttttctcttc caattgtcta aatcaatttt | 5760 |
| attaaagttc atttgatatg cctcctaaat ttttatctaa agtgaattta ggaggcttac | 5820 |
| ttgtctgctt tcttcattag aatcaatcct tttttaaaag tcaatgacgg atccggggag | 5880 |
| cggccgccag tgtgatggat atctgcagaa ttccagcaca ctggcggccg ttactagtga | 5940 |
| acctcctata cattgatcct atgttacttc aataaatttt cggcttattt ttaaggcggg | 6000 |
| tttaggaaaa aagtctatac aagctttaaa tttttaaagg acgccccaag tttattggta | 6060 |
| ccaagcttga tgcaggcatg caagcttggc gtaatcatgg tcatagctgt ttcctgtgtg | 6120 |
| aaattgttat ccgctcacaa ttccacacaa catacgagcc ggaagcataa agtgtaaagc | 6180 |
| ctggggtgcc taatgagtga gctaactcac attaattgcg ttgcgctcac tgcccgcttt | 6240 |
| ccagtcggga aacctgtcgt gccagctgca ttaatgaatc ggccaacgcg cggggagagg | 6300 |
| cggtttgcgt attgggcgct | 6320 |

<210> SEQ ID NO 10
<211> LENGTH: 6320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| caaccgcttc ctcgctcact gactcgctgc gctcggtcgt tcggctgcgg cgagcggtat | 60 |
| cagctcactc aaaggcggta atacggttat ccacagaatc aggggataac gcaggaaaga | 120 |
| acatgtgagc aaaaggccag caaaaggcca ggaaccgtaa aaaggccgcg ttgctggcgt | 180 |
| ttttccatag gctacgcccc cctgacgagc atcacaaaaa tcgacgctca agtcagaggt | 240 |
| ggcgaaaccc gacaggacta taaagatacc aggcgtttcc ccctggaagc tccctcgtgc | 300 |
| gctctcctgt tccgaccctg ccgcttaccg gatacctgtc cgcctttctc ccttcgggaa | 360 |
| gcgtggcgct ttctcatagc tcacgctgta ggtatctcag ttcggtgtag tcgttcgct | 420 |
| ccaagctggg ctgtgtgcac gaaccccccg ttcagcccga ccgctgcgcc ttatccggta | 480 |
| actatcgtct tgagtccaac ccggtaagac acgacttatc gccactggca gcagccactg | 540 |
| gtaacaggat tagcagagcg aggtatgtag gcggtgctac agagttcttg aagtggtggc | 600 |
| ctaactacgg ctacactaga agaacagtat ttggtatctg cgctctgctg aagccagtta | 660 |
| ccttcggaaa aagagttggt agctcttgat ccggcaaaca aaccaccgct ggtagcggtg | 720 |
| gttttttgt ttgcaagcag cagattacgc gcagaaaaaa aggatctcaa gaagatcctt | 780 |
| tgatcttttc tacggggtct gacgctcagt ggaacgaaaa ctcacgttaa gggattttgg | 840 |

```
tcatgagatt atcaaaaagg atcttcacct agatccttt cctcgagatc cgcgcgttta    900
atgaccagca cagtcgtgat ggcaaggtca gaatagcgct gaggtctgcc tcgtgaggaa    960
ggtgtagtta actcatacca ggcctgaatc gccccatcat ccagccagaa agtgagggag   1020
ccacggttga tgagagcttt gttgtaggtg cagcagttgg tgattttgaa cttttgcttt   1080
gccacggaac ggtctgcgtt gtcgggaaga tgcgtgatct gatccttcaa ctcagcaaaa   1140
gttcgattta ttcaacaaag ccacgttgtg tctcaaaatc tctgatgtta cattgcacaa   1200
gataaaaata tatcatcatg aacaataaaa ctgtctgctt acataaacag taatacaagg   1260
ggtgttatga gccatattca acgggaaacg tcttgctcga ggccgcgatt aaattccaac   1320
atggatgctg atttatatgg gtataaatgg gctcgcgata atgtcgggca atcaggtgcg   1380
acaatctatc gattgtatgg gaagcccgat gcgccagagt tgtttctgaa acatggcaaa   1440
ggtagcgttg ccaatgatgt tacagatgag atggtcagac taaactggct gacggaattt   1500
atgcctctgc cgaccatcaa gcattttatc cgtactcctg atgatgcatg gttactcacc   1560
actgcgatcc ccggaaaaac agcattccag gtattagaag aatatcctga ttcaggtgag   1620
aatattgttg atgcgctggc agtgttcctg cgccggttgc attcgattcc tgtttgtaat   1680
tgtcctttta acagcgatcg cgtatttcgt ctcgctcagg cgcaatcacg aatgaataac   1740
ggtttggttg atgcgagtga ttttgatgac gagcgtaatg gctggcctgt tgaacaagtc   1800
tggaaagaaa tgcataaact tttgccattc tcaccggatt cagtcgtcac tcatggtgat   1860
ttctcacttg ataaccttat ttttgacgag gggaaattaa taggttgtat tgatgttgga   1920
cgagtcggaa tcgcagaccg ataccaggat cttgccatcc tatggaactg cctcggtgag   1980
ttttctcctt cattacagaa acggcttttt caaaaatatg gtattgataa tcctgatatg   2040
aataaattgc agtttcattt gatgctcgat gagttttttct aatcagaatt ggttaattgg   2100
ttgtaacact ggcagagcat tacgctgact tgacgggacg gcggctttgt tgaataaatc   2160
gaacttttgc tgagttgaag gatctcgagg tgcaccatat gcggtgtgaa ataccgcaca   2220
gatgcgtaag gagaaaatac cgcatcaggc gccattcgcc attcaggctg cctcggtacc   2280
cggggatccg caggggactg acatatttaa agctgagatt tatggttgcg gagaaaattgt   2340
atctccggga ttgtgagttc tcggctttt tttatttaaa aactgttttt tatacttgaa   2400
aaaaacagct ctgctcatgc ctgtaagctc acaaaattct ttcaccgttg attttgaatg   2460
acattctaaa aatgtaaaaa cggcatctct atatgacttt ctgccattgc catcgcgcca   2520
attcgtatca tcatatttgt ctttaatagc ttggatggct ctagctccct ctaaatgttg   2580
tttttgtttt ctcccgttac gcttatttgc ttttatttca ataccggaca atttagaaat   2640
ctcatctcta ggaaaagacc tataacattc ctgatacatt tctaaagcac tctcaatatc   2700
ataatctgta aacggttcat cgggattttt atcattcaag taattctgaa agaataggc    2760
atcttttttc aactcatcaa aatcaatacc gcatttaacc gcataaaccg tcaaacacat   2820
tataaaaaaa tacctatgat gatatacaat gcctgtaact tgccttttcc accaatcata   2880
caaagcacgt ttacaagtcc attcttttt ttcgcggcca agttctatac gctgatgata   2940
ccaatccgga tatttctttt ttgcttcctc aagtgttaat tttgaatgat aaaaagtatc   3000
tgttattcga ttttcaggag caacaaacct ggataagtaa tcaagagtca ctttttcgcc   3060
tgttttatgg gcaagaatcg tatagccgcg tttttgaccca ctaccaacaa gcctaaatcc   3120
ttgatttatg ccttgaaact gccgctgttt tagtctggat gtatcacgat tccatagttt   3180
```

```
ttctgtaaga gcgtatttta attttttgag ttgtctttga atatttggat agagagggat    3240
aggattttca aataaataat ataaatgtac accgtttccg gaattaacaa cataagtagg    3300
ggtaggcaag cgctgatagt taccaccagg gaaaggttta tcatatgcat aaaaatacca    3360
cgtaaaaagc agctccaact ctttcgcccc aacctcatct aaatcaaaaa caagagcaaa    3420
tagttcccta gcatttgcta aagtcctatt tttcccaaaa tatgaaatag gagacataaa    3480
ggcacaatca ttacgagtat gctcccaaat ctccgaatgg tcatcaaaaa ccatacgcgt    3540
acgttttttt tcttctgaag tcgtatacac caaaaaacca ttacctttat ttgtttttgg    3600
ataatcaact aagaaccccca ttcttttcctc aaagctgcca aaaggaaaaa catctctata    3660
aaaatctgga gcataaacta ttttaaaatc aaagtcaaat ttttgtttag cagtcttaag    3720
aaaccactcc tcttttttcaa aaacaagtc actcatacta agcatattat accgtagggg    3780
gcgtatatta tcaatacatt aaatagactt catgcataaa taaaatgtca aatcactggt    3840
tatatttcta agcacttcaa catcataggg ggcgtatatt atcaatatat aaatggaaaa    3900
agcagagaca tactttaatc gttatcacac aataatcaaa ctcttagatt tggccgttct    3960
tataagcttt catcaagaat tcatttactt ctgattgcca gcgcttacct tttgatcgaa    4020
aatgttctaa caagactta ttaaaacgaa tagagacctg ttcttttaca ggtttaaaat    4080
atttctcatt tccaaaataa aaaccgtcca agctatttat ttccggtatt tcagatgtat    4140
ctattagctc atccggaatc gcatttcttt cacattcagc cattatttgc gagatattta    4200
attttttcat aatacatttc tcttttcccgt ttcaacgcag gacgcgccga tataattctt    4260
tttttgccat ttttcggcgt ataaacaaca aaaacaacca actgactttt gactctgcca    4320
agaacttgat agcgttcttc ttctagcgtt gaatgagtta catcatactt ttccagataa    4380
aatgggtcat caaaaacttg ttgagcttcc tcgaaagtta aacctgcatg ctttttttta    4440
ttcaattgag cctttgataa atgccattct gtaacatcat tattcatcgt aaaattgtat    4500
cacaaaattg tatttttgta aattacataa ttactatcac ctttcgaaat ctatagattt    4560
ctcacgtgtt tttgtattca ttgtttcatg tttggcttta tcagaccaac ttttaaaatt    4620
ctcattttgc aactttgttg caagatttat taactgttta ggactagcac tttcccattg    4680
atttactttc tccatctctc tctttaaatc gctctccaag gcctctaaac gcctctgtac    4740
ggcgtttaga ttacttttta gtgttaaatt atccctactc aattctaata ccttttcttc    4800
gtgttttga agcagtggta aaattttagc tttgtaacgt acagaatact gctcaaaact    4860
ttctaacatt ttttttgcag gcggctctat agctttatcc agctgttcaa gcttggtata    4920
aaactgtttt acggtctgat gtcgtgcttt agagcctttt acacctcttt ccaacccgaa    4980
tttttttgcca acttgctcaa aaaaactatc ctgcatggat ccgtctctgg agctgtaata    5040
taaaaaccctt cttcaactaa cggggcaggt tagtgacatt agaaaaccga ctgtaaaaag    5100
tacagtcggc attatctcat attataaaag ccagtcatta ggcctatctg acaattcctg    5160
aatagagttc ataaacaatc ctgcatgata accatcacaa actgaatgat gtacttgtaa    5220
agatagcggt aaatatattg aattaccttt attaatgaat tttcctgctg taataatggg    5280
tagaaggtaa ttactattat tattgatatt taagttaaac ccagtaaatg aagtccatgg    5340
aataatagaa agagaaaaag cattttcagg tataggtgtt ttgggaaaca atttccccga    5400
accattatat ttctctacat cagaaaggta taaatcataa aactctttga agtcattctt    5460
tacaggagtc caaataccag agaatgtttt agatacacca tcaaaattg tataaagtgg    5520
ctctaactta tcccaataac ctaactctcc gtcgctattg taaccagttc taaaagctgt    5580
```

```
atttgagttt atcacccttg tcactaagaa aataaatgca gggtaaaatt tatatccttc   5640
ttgttttatg tttcggtata aaacactaat atcaatttct gtggttatac taaaagtcgt   5700
ttgttggttc aaataatgat taaatatctc ttttcgcttc caattgtcta aatcaatttt   5760
attaaagttc atttgatatg cctcctaaat ttttatctaa agtgaattta ggaggcttac   5820
ttgtctgctt tcttcattag aatcaatcct tttttaaaag tcaatgacgg atccggggag   5880
cggccgccag tgtgatggat atctgcagaa ttccagcaca ctggcggccg ttactagtga   5940
acctcctata cattgatcct atgttacttc aataaatttt cggcttattt ttaaggcggg   6000
tttaggaaaa aagtctatac aagctttaaa tttttaaagg acgccccaag tttattggta   6060
ccaagcttga tgcaatcatg caagcttggc gtaatcatgg tcatagctgt ttcctgtgtg   6120
aaattgttat ccgctcacaa ttccacacaa catacgagcc ggaagcataa agtgtaaagc   6180
ctggggtgcc taatgagtga gctaactcac attaattgcg ttgcgctcac tgcccgcttt   6240
ccagtcggga aacctgtcgt gccagctgca ttaatgaatc ggccaacgcg cggggagagg   6300
cggtttgcgt attgggcgct                                              6320
```

<210> SEQ ID NO 11  
<211> LENGTH: 13  
<212> TYPE: DNA  
<213> ORGANISM: Staphylococcus aureus  
<220> FEATURE:  
<221> NAME/KEY: modified_base  
<222> LOCATION: (5)..(10)  
<223> OTHER INFORMATION: a, c, t, g, unknown or other

<400> SEQUENCE: 11

```
ccaynnnnnn tgt                                                       13
```

<210> SEQ ID NO 12  
<211> LENGTH: 11  
<212> TYPE: DNA  
<213> ORGANISM: Staphylococcus aureus  
<220> FEATURE:  
<221> NAME/KEY: modified_base  
<222> LOCATION: (4)..(8)  
<223> OTHER INFORMATION: a, c, t, g, unknown or other

<400> SEQUENCE: 12

```
aggnnnnnga t                                                         11
```

<210> SEQ ID NO 13  
<211> LENGTH: 6850  
<212> TYPE: DNA  
<213> ORGANISM: Artificial Sequence  
<220> FEATURE:  
<223> OTHER INFORMATION: Description of Artificial Sequence: Synthetic
      polynucleotide

<400> SEQUENCE: 13

```
ggcggccgca ctggcttact atgttggcac tgatgagggt gtcagtgaag tgcttcatgt     60
ggcaggagaa aaaaggctgc accggtgcgt cagcagaata tgtgatacag gatatattcc    120
gcttcctcgc tcactgactc gctacgctcg gtcgttcgac tgcggcgagc ggaaatgcgt    180
tacgaacggg gcggagattt cctggaagat gccaggaaga tacttaacag ggaagtgaga    240
gggccgcggc aaagccgttt ttccataggc tccgcccccc tgacaagcat cacgaaatct    300
gacgctcaaa tcagtggtgg cgaaacccga caggactata agataccagg cgtttccccc    360
ctggcggctc cctcgtgcgc tctcctgttc ctgcctttcg gtttaccggt gtcattccgc    420
```

```
tgttatggcc gcgtttgtct cattccacgc ctgacactca gttccgggta ggcagttcgc    480
tccaagctgg actgtatgca cgaaccccccc gttcagtccg accgctgcgc cttatccggt   540
aactatcgtc ttgagtccaa cccggaaaga catgcaaaag caccactggc agcagccact    600
ggtaattgat ttagaggagt tagtcttgaa gtcatgcgcc ggttaaggct aaactgaaag    660
gacaagtttt ggtgactgcg ctcctccaag ccagttacct cggttcaaag agttggtagc    720
tcagagaacc ttcgaaaaac cgccctgcaa ggcggttttt tcgttttcag agcaagagat    780
tacgcgcaga ccaaaacgat ctcaagaaga tcatcttatg cggccgcttc tttcctgcgt    840
tatcccctga ttctgtggat aaccgtatta ccgcctttga gtgagctgat accgctcgcc    900
gcagccgaac gaccgagcgc agcgagtcag tgagcgagga agcggaagag cgcctgatgc    960
ggtattttct ccttacgcat ctgtgcggta tttcacaccg cataggaaga tccctcgacc   1020
tgcaggcatg caagcttctg taggttttta ggcataaaac tatatgattt accccctaaat  1080 cttttaaaatg ccccttaaaa ttcaaaataa aggcatttaa aatttaaata tttcttgtga   1140
taaagtttgt taaaaggag tggttttatg actgttatgt ggttatcgat tataggtatg    1200
tggttttgta ttggaatggc attttttgct atcaaggtta ttaaaaataa aaattagacc    1260
acgcatttat gccgagaaaa tttattgtgc gttgagaaga acccttaact aaacttgcag    1320
acgaatgtcg gcatagcgtg agctattaag ccgaccattc gacaagtttt gggattgtta    1380
agggttccga ggctcaacgt caataaagca attggaataa agaagcgaaa aggagaagt    1440 cggttcagaa aaagaaggat atggatctgg agctgtaata taaaaaccctt cttcaactaa   1500 cggggcaggt tagtgacatt agaaaaccga ctgtaaaaag tacagtcggc attatctcat    1560
attataaaag ccagtcatta ggcctatctg acaattcctg aatagagttc ataaacaatc    1620
ctgcatgata accatcacaa acagaatgat gtacctgtaa agatagcggt aaatatattg    1680
aattaccttt attaatgaat tttcctgctg taataatggg tagaaggtaa ttactattat    1740
tattgatatt taagttaaac ccagtaaatg aagtccatgg aataatagaa agagaaaaag    1800
cattttcagg tataggtgtt ttgggaaaca atttccccga accattatat ttctctacat    1860
cagaaaggta taaatcataa aactctttga agtcattctt tacaggagtc caaataccag    1920
agaatgtttt agatacacca tcaaaaattg tataaagtgg ctctaactta tcccaataac    1980
ctaactctcc gtcgctattg taaccagttc taaaagctgt atttgagttt atcacccttg    2040
tcactaagaa aataaatgca gggtaaaatt tatatccttc ttgttttatg tttcggtata    2100
aaacactaat atcaatttct gtggttatac taaaagtcgt tgttggttc aaataatgat     2160 taaatatctc ttttctcttc caattgtcta aatcaatttt attaaagttc atttgatatg    2220
cctcctaaat ttttatctaa agtgaattta ggaggcttac ttgtctgctt tcttcattag    2280
aatcaatcct ttttttaaaag tcaatattac tgtaacataa atatatattt taaaaatatc   2340
ccactttatc caattttcgt tgttgaact aatgggtgct ttagttgaag aataaaagac     2400
cacattaaaa aatgtggtct tttgtgtttt tttaaaggat ttgagcgtag cgaaaaatcc    2460
ttttctttct tatcttgata ataagggtaa ctattgccgg cgaggctagt tacccttaag   2520
ttattggtat gactggtttt aagcgcaaaa aaagttgctt tttcgtacct attaatgtat    2580
cgttttaaat gaatagtaaa aaacatacat agaaagggga aaaagcaact ttttttattg    2640
tcatagtttg tgaaaactaa gttgtttta tgtgttataa catggaaaag tatactgaga     2700
aaaaacaaag aaatcaagta tttcagaaat ttattaaacg tcatattgga gagaatcaaa    2760
```

```
tggatttagt tgaagattgc aatacatttc tgtcttttgt agctgataaa actttagaaa    2820
aacagaaatt atataaagct aattcttgta aaaatcgatt ttgtcctgtc tgtgcttgga    2880
gaaaagctag aaaagatgca ttgggtttat ctttgatgat gcaatatatt aagcagcaag    2940
agaaaaagga gtttatcttt ttaactttga ctacacctaa tgtaatgagt gatgaattag    3000
aaaatgaaat aaaacgttat aataattctt ttagaaaact tataaagaga aaaaagtag     3060 gtagtgttat aagggatat gttcgtaagt tagagattac atataataaa aaagagatg     3120 attataatcc tcattttcat gtgttaattg cagtaaataa atcgtatttc acagataaaa    3180
gatattatat tagccaacaa gaatggttag atttatggcg tgatgtaacg ggcatttcag    3240
aaataacaca agttcaagtt caaaaaataa gacaaaataa taataaagaa ttatatgaaa    3300
tggctaagta ttctggtaaa gatagtgatt atttaataaa tcaaaaagtc tttgatgcat    3360
tttataaatc acttaaaggt aaacaggtat tagtttattc aggattattt aaagaggcta    3420
aaaagaaatt aaaaaatggg gatttagatt acttaaaaga aattgatcca accgaatata    3480
tctatcaaat ttttatatt tggaaacaaa aagagtattt agctagtgaa ctttatgact    3540
taacagaaca agaaaaaaga gaattaatc acaaaatgat agacgaaatc gaggaagaac    3600
aataacaaaa tataagtgct aacagtcgtc tgcaagttta gttaagggtt cttctcaacg    3660
cacaataaat tttctcggca taaatgcgtg gtctaatttt tattttaat aaccttgata    3720 gcaaaaaatg ccattccaat acaaaaccac atacctataa tcgataacca cataacagtc    3780 ataaaccac tcctttttaa caaactttat cacaagaaat attttggcat tctacgacta    3840
taacttaaat ttatatttt tactttataa tatataattg attatagaat aatgttgctc    3900
atatcgtttg ccaacatcta gtactcaaat tacactatgt tacacttggt aatattaacc    3960
gaacttcccc tgtccaaatt agataagagg taataataaa tggaaaataa ttttatagta    4020
aatgaaaatg agaagcgtgt attaaaacaa attttcaata acagcaatat ttcacgaaca    4080
caaatatcga agaatttaga acttaataaa gctactattt ctaacattct gaacaactta    4140
aaacacaaga gtttagttaa tgaagtagga gaaggtaata gtactaaaag tggtggacga    4200
aagcctattt tactcgaaat taaccaaaaa tatggctact atatttctat ggatttaaca    4260
tatgattccg ttgaattaat gtacaactac tttgatgcta ctatattaaa gcaagattcc    4320
tacgaattaa atgataaaaa tgtaagcagt atattacaaa ttttaaaatc taatatacac    4380
gtctcagaaa aatatgatac gttatatggg ttacttggta tatctatatc catacacggt    4440
atcgttgacg atgagcaaaa cataatcaat cttccttttc ataaaaatga gaaacgcaca    4500
tttaccgatg aattaaagtc attcacaaat gttcctgtcg ttatagaaaa tgaagcaaat    4560
ttatcagcgc tatatgaaaa aagtttatat attaattcaa acataaataa tttgattact    4620
ttaagtattc acaagggtat aggcgctggc atcctaataa ataaaaaact ttatcgtggc    4680
tcaaatggag aggctggaga gataggtaag acattggttt tggaatctat aaataacaat    4740
gacaacaaat attataaaat cgaagatata tgctcccaag acgctttaat acagaaaata    4800
aataataggt tgggcgtcac attgacgttt acagaactaa tccaatatta caacgaagga    4860
aattcaattg ttgctcatga aattaaacaa tttattaata aaatgacagt tctgattcat    4920
aatttgaata cacaatttaa cccagacgct atttatatta actgtccttt aattaatgaa    4980
ttaccaaata ttttaaatga aattaaagag caattctcct gttttctca aggcagtcca    5040 gttcaattac atttaactac taatgtaaaa caagctactt tattgggtgg cactttagca    5100
ataatgcaaa aaacattaaa tataaataac attcaaatga atattaaata attacagcag    5160
```

-continued

```
tctgagttat aaaatagata tctcggaccg tcataaaaaa tttatttgct ttcaggaaaa    5220 ttttctgta  taatagattc aagttagttt gtttattaaa ttaaccaact aaaatgtaga    5280
attcgagctc ggtacccggg gatcctctag agtcgacctg cagccaagct tgggcttttc    5340
agcctgatac agattaaatc agaacgcaga agcggtctga taaaacagaa tttgcctggc    5400
ggcagtagcg cggtggtccc acctgacccc atgccgaact cagaagtgaa acgccgtagc    5460
gccgatggta gtgtggggtc tccccatgcg agagtaggga actgccaggc atcaaataaa    5520
acgaaaggct cagtcgaaag actgggcctt tcgttttatc tgttgtttgt cggtgaacgc    5580
tctcctgagt aggacaaatc cgccgggagc ggatttgaac gttgcgaagc aacggcccgg    5640
agggtggcgg gcaggacgcc cgccataaac tgccaggcat caaattaagc agaaggccat    5700
cctgacggat ggcctttttg cgtttctaca aactcttttg tttatttttc taaatacatt    5760
caaatatgta tccgctcatc cccatcctat cgatgataag ctgtcaaaca tgagaattaa    5820
atcaatctaa agtatatatg agtaaacttg gtctgacagt taccaatgct taatcagtga    5880
ggcacctatc tcagcgatct gtctatttcg ttcatccata gttgcctgac tccccgtcgt    5940
gtagataact acgatacggg agggcttacc atctggcccc agtgctgcaa tgataccgcg    6000
agacccacgc tcaccggctc cagatttatc agcaataaac cagccagccg aagggccga    6060 gcgcagaagt ggtcctgcaa ctttatccgc ctccatccag tctattaatt gttgccggga    6120
agctagagta agtagttcgc cagttaatag tttgcgcaac gttgttgcca ttgctacagg    6180
catcgtggtg tcacgctcgt cgtttggtat ggcttcattc agctccggtt cccaacgatc    6240
aaggcgagtt acatgatccc ccatgttgtg caaaaaagcg gttagctcct tcggtcctcc    6300
gatcgttgtc agaagtaagt tggccgcagt gttatcactc atggttatgg cagcactgca    6360
taattctctt actgtcatgc catccgtaag atgcttttct gtgactggtg agtactcaac    6420
caagtcattc tgagaatagt gtatgcggcg accgagttgc tcttgcccgg cgtcaacacg    6480
ggataatacc gcgccacata gcagaacttt aaaagtgctc atcattggaa aacgctcttc    6540
ggggcgaaaa ctctcaagga tcttaccgct gttgagatcc agttcgatgt aacccactcg    6600
tgcacccaac tgatcttcag catcttttac tttcaccagc gtttctgggt gagcaaaaac    6660
aggaaggcaa aatgccgcaa aaaagggaat aagggcgaca cggaaatgtt gaatactcat    6720
actcttcctt tttcaatatt attgaagcat ttatcagggt tattgtctca tgagcggata    6780
catatttgaa tgtatttaga aaaataaaca ataggggtt ccgcgcacat ttccccgaaa     6840
agtgccacct                                                            6850
```

<210> SEQ ID NO 14
<211> LENGTH: 11
<212> TYPE: DNA
<213> ORGANISM: Staphylococcus aureus

<400> SEQUENCE: 14
aggatgggga t                                                           11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
acgatgggca t                                                              11

<210> SEQ ID NO 16
<211> LENGTH: 11
<212> TYPE: DNA
<213> ORGANISM: Staphylococcus aureus

<400> SEQUENCE: 16
aggatatgga t                                                              11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agcatatgca t                                                              11

<210> SEQ ID NO 18
<211> LENGTH: 15
<212> TYPE: DNA
<213> ORGANISM: Prevotella intermedia

<400> SEQUENCE: 18
cgagctagtt catgt                                                          15

<210> SEQ ID NO 19
<211> LENGTH: 50
<212> TYPE: DNA
<213> ORGANISM: Prevotella intermedia

<400> SEQUENCE: 19
aaagaccccg ggacctttac tataccttgg tattggcatc aggtgcggat                    50

<210> SEQ ID NO 20
<211> LENGTH: 15
<212> TYPE: DNA
<213> ORGANISM: Treponema denticola
<220> FEATURE:
<221> NAME/KEY: modified_base
<222> LOCATION: (4)..(11)
<223> OTHER INFORMATION: a, c, t, g, unknown or other

<400> SEQUENCE: 20
ccannnnnnn ntdcc                                                          15

<210> SEQ ID NO 21
<211> LENGTH: 13
<212> TYPE: DNA
<213> ORGANISM: Treponema denticola
<220> FEATURE:
<221> NAME/KEY: modified_base
<222> LOCATION: (6)..(10)
<223> OTHER INFORMATION: a, c, t, g, unknown or other

<400> SEQUENCE: 21
dtaaynnnnn tcc                                                            13

<210> SEQ ID NO 22
<211> LENGTH: 12
<212> TYPE: DNA
<213> ORGANISM: Treponema denticola
```

```
<220> FEATURE:
<221> NAME/KEY: modified_base
<222> LOCATION: (4)..(8)
<223> OTHER INFORMATION: a, c, t, g, unknown or other

<400> SEQUENCE: 22
ggannnnnrt ta                                                           12

<210> SEQ ID NO 23
<211> LENGTH: 36
<212> TYPE: DNA
<213> ORGANISM: Treponema denticola

<400> SEQUENCE: 23
gtttgagagt tgtgtaattt aagatgggtc tcaaac                                 36

<210> SEQ ID NO 24
<211> LENGTH: 36
<212> TYPE: DNA
<213> ORGANISM: Treponema denticola

<400> SEQUENCE: 24
gtttgagagt tatgtaattt aagatgggtc tcaaac                                 36

<210> SEQ ID NO 25
<211> LENGTH: 35
<212> TYPE: DNA
<213> ORGANISM: Treponema denticola

<400> SEQUENCE: 25
gtttgagagt tgtgtaattt aagatgcaac caaac                                  35

<210> SEQ ID NO 26
<211> LENGTH: 36
<212> TYPE: DNA
<213> ORGANISM: Treponema denticola

<400> SEQUENCE: 26
gtttgagagt tgtgtaattt aagatggatc tcaaac                                 36

<210> SEQ ID NO 27
<211> LENGTH: 30
<212> TYPE: DNA
<213> ORGANISM: Treponema denticola

<400> SEQUENCE: 27
tataggaggt ttcaaaatgg aaaaatcgaa                                        30

<210> SEQ ID NO 28
<211> LENGTH: 30
<212> TYPE: DNA
<213> ORGANISM: Treponema denticola

<400> SEQUENCE: 28
tatcaagttg agccttcttt aaagctccgc                                        30

<210> SEQ ID NO 29
<211> LENGTH: 30
<212> TYPE: DNA
<213> ORGANISM: Treponema denticola

<400> SEQUENCE: 29
tataggagtt ccagacccag caccatcacc                                        30
```

<210> SEQ ID NO 30
<211> LENGTH: 30
<212> TYPE: DNA
<213> ORGANISM: Treponema denticola

<400> SEQUENCE: 30
aaaatcgaat gtatcgcaag attcaaacca                                    30

<210> SEQ ID NO 31
<211> LENGTH: 30
<212> TYPE: DNA
<213> ORGANISM: Treponema denticola

<400> SEQUENCE: 31
tacaaaatcg aagcagaaga aaggaacttc                                    30

<210> SEQ ID NO 32
<211> LENGTH: 30
<212> TYPE: DNA
<213> ORGANISM: Treponema denticola

<400> SEQUENCE: 32
ggttccaatc ttttggaat gattaacaat                                     30

<210> SEQ ID NO 33
<211> LENGTH: 30
<212> TYPE: DNA
<213> ORGANISM: Treponema denticola

<400> SEQUENCE: 33
gattctgtat ttcaacgcga tgttgctaat                                    30

<210> SEQ ID NO 34
<211> LENGTH: 30
<212> TYPE: DNA
<213> ORGANISM: Treponema denticola

<400> SEQUENCE: 34
ctaacaaaag gtggaatttt accgaacaat                                    30

<210> SEQ ID NO 35
<211> LENGTH: 29
<212> TYPE: DNA
<213> ORGANISM: Treponema denticola

<400> SEQUENCE: 35
aattagttgt cattgaaggt gaagccgga                                     29

<210> SEQ ID NO 36
<211> LENGTH: 30
<212> TYPE: DNA
<213> ORGANISM: Treponema denticola

<400> SEQUENCE: 36
gcggaaaaac tatatcgtaa tcttcataga                                    30

<210> SEQ ID NO 37
<211> LENGTH: 30
<212> TYPE: DNA
<213> ORGANISM: Treponema denticola

<400> SEQUENCE: 37
gctggaacgc ctatagcgac gcaagctcct                                    30

<210> SEQ ID NO 38
<211> LENGTH: 30
<212> TYPE: DNA
<213> ORGANISM: Treponema denticola

<400> SEQUENCE: 38
cgctggaacg cctatagcga cgcaagctcc              30

<210> SEQ ID NO 39
<211> LENGTH: 30
<212> TYPE: DNA
<213> ORGANISM: Treponema denticola

<400> SEQUENCE: 39
ggttccaatc tttttggaat gattaacaat              30

<210> SEQ ID NO 40
<211> LENGTH: 30
<212> TYPE: DNA
<213> ORGANISM: Treponema denticola

<400> SEQUENCE: 40
catctagaat cctataaggc acgaagtaat              30

<210> SEQ ID NO 41
<211> LENGTH: 30
<212> TYPE: DNA
<213> ORGANISM: Treponema denticola

<400> SEQUENCE: 41 cctttttgt aactcctatt tgcagctatg               30

<210> SEQ ID NO 42
<211> LENGTH: 30
<212> TYPE: DNA
<213> ORGANISM: Treponema denticola

<400> SEQUENCE: 42
attacttttc gaaaaaaagc cgtattatag              30

<210> SEQ ID NO 43
<211> LENGTH: 30
<212> TYPE: DNA
<213> ORGANISM: Treponema denticola

<400> SEQUENCE: 43
tctttgtatt ataaagttag cagaggaaaa              30

<210> SEQ ID NO 44
<211> LENGTH: 30
<212> TYPE: DNA
<213> ORGANISM: Treponema denticola

<400> SEQUENCE: 44
gaatctacca ccctcaatac tccgcctatt              30

<210> SEQ ID NO 45
<211> LENGTH: 30
<212> TYPE: DNA
<213> ORGANISM: Treponema denticola

<400> SEQUENCE: 45
gtcaacatca ccgcgatcac tacaaacagc                                    30

<210> SEQ ID NO 46
<211> LENGTH: 30
<212> TYPE: DNA
<213> ORGANISM: Treponema denticola

<400> SEQUENCE: 46
gaatgaaaag gacaaggaaa aagctgccct                                    30

<210> SEQ ID NO 47
<211> LENGTH: 30
<212> TYPE: DNA
<213> ORGANISM: Treponema denticola

<400> SEQUENCE: 47
tgattatttg gaaggcatga gtaaatgctg                                    30

<210> SEQ ID NO 48
<211> LENGTH: 30
<212> TYPE: DNA
<213> ORGANISM: Treponema denticola

<400> SEQUENCE: 48
gcagtaactc acaagccact ttgagagttg                                    30

<210> SEQ ID NO 49
<211> LENGTH: 30
<212> TYPE: DNA
<213> ORGANISM: Treponema denticola

<400> SEQUENCE: 49
ttcgacgctt gtcgaaaagg caatcaaggc                                    30

<210> SEQ ID NO 50
<211> LENGTH: 30
<212> TYPE: DNA
<213> ORGANISM: Treponema denticola

<400> SEQUENCE: 50
cgagaagtta ttattctgaa cttcacatcg                                    30

<210> SEQ ID NO 51
<211> LENGTH: 30
<212> TYPE: DNA
<213> ORGANISM: Treponema denticola

<400> SEQUENCE: 51
ctttggtatc aattaggatt tcctaaagtc                                    30

<210> SEQ ID NO 52
<211> LENGTH: 30
<212> TYPE: DNA
<213> ORGANISM: Treponema denticola

<400> SEQUENCE: 52
tacaatgatt gcttgttgtt ctgatggaac                                    30

<210> SEQ ID NO 53
<211> LENGTH: 30
<212> TYPE: DNA
<213> ORGANISM: Treponema denticola

<400> SEQUENCE: 53
tagcctcacc attataaagc aattcgcatg                                              30

<210> SEQ ID NO 54
<211> LENGTH: 30
<212> TYPE: DNA
<213> ORGANISM: Treponema denticola

<400> SEQUENCE: 54
tgttacgtca aaaaatccaa taagttgaag                                              30

<210> SEQ ID NO 55
<211> LENGTH: 30
<212> TYPE: DNA
<213> ORGANISM: Treponema denticola

<400> SEQUENCE: 55
cctgataagg aagattggcg aaagaaggta                                              30

<210> SEQ ID NO 56
<211> LENGTH: 30
<212> TYPE: DNA
<213> ORGANISM: Treponema denticola

<400> SEQUENCE: 56
tgctacatca aataacccta caagttgaag                                              30

<210> SEQ ID NO 57
<211> LENGTH: 30
<212> TYPE: DNA
<213> ORGANISM: Treponema denticola

<400> SEQUENCE: 57
ccaaaagttc acagtcatcc gagtagacgt                                              30

<210> SEQ ID NO 58
<211> LENGTH: 30
<212> TYPE: DNA
<213> ORGANISM: Treponema denticola

<400> SEQUENCE: 58
ctatctactt tgggaaccc taattggtac                                               30

<210> SEQ ID NO 59
<211> LENGTH: 30
<212> TYPE: DNA
<213> ORGANISM: Treponema denticola

<400> SEQUENCE: 59
tttcttctgt ttgtccatgt ccaaacctcc                                              30

<210> SEQ ID NO 60
<211> LENGTH: 30
<212> TYPE: DNA
<213> ORGANISM: Treponema denticola

<400> SEQUENCE: 60
aacaatgtgt gattttcgg acttagtccc                                               30

<210> SEQ ID NO 61
<211> LENGTH: 30
<212> TYPE: DNA
<213> ORGANISM: Treponema denticola

```
<400> SEQUENCE: 61
aagggaataa ccttaccatt ctgtcttatg                              30

<210> SEQ ID NO 62
<211> LENGTH: 30
<212> TYPE: DNA
<213> ORGANISM: Treponema denticola

<400> SEQUENCE: 62
ttcccaaaag ttgatgctga tacgattggt                              30

<210> SEQ ID NO 63
<211> LENGTH: 30
<212> TYPE: DNA
<213> ORGANISM: Treponema denticola

<400> SEQUENCE: 63
aacaatcagc cgtgagggaa tacgccgcgt                              30

<210> SEQ ID NO 64
<211> LENGTH: 30
<212> TYPE: DNA
<213> ORGANISM: Treponema denticola

<400> SEQUENCE: 64
aggttaatga tgaaaaaaat aataactact                              30

<210> SEQ ID NO 65
<211> LENGTH: 30
<212> TYPE: DNA
<213> ORGANISM: Treponema denticola

<400> SEQUENCE: 65
gggcatatta tgcagatatg caacgaaacg                              30

<210> SEQ ID NO 66
<211> LENGTH: 30
<212> TYPE: DNA
<213> ORGANISM: Treponema denticola

<400> SEQUENCE: 66
cttggaaaag aatttataaa atgcgaagtt                              30

<210> SEQ ID NO 67
<211> LENGTH: 30
<212> TYPE: DNA
<213> ORGANISM: Treponema denticola

<400> SEQUENCE: 67
gaacatatgc tcgctctttc tcgagtactc                              30

<210> SEQ ID NO 68
<211> LENGTH: 30
<212> TYPE: DNA
<213> ORGANISM: Treponema denticola

<400> SEQUENCE: 68
aaactttgag gtactaaata aaacaagtca                              30

<210> SEQ ID NO 69
<211> LENGTH: 30
<212> TYPE: DNA
<213> ORGANISM: Treponema denticola
```

```
<400> SEQUENCE: 69
acctttcaat agtagcatcg ggcaaaccag                               30

<210> SEQ ID NO 70
<211> LENGTH: 30
<212> TYPE: DNA
<213> ORGANISM: Treponema denticola

<400> SEQUENCE: 70
gtctctagtt actttacgta taaactctat                               30

<210> SEQ ID NO 71
<211> LENGTH: 30
<212> TYPE: DNA
<213> ORGANISM: Treponema denticola

<400> SEQUENCE: 71
gggcatatta tgcagatatg caacgaaacg                               30

<210> SEQ ID NO 72
<211> LENGTH: 30
<212> TYPE: DNA
<213> ORGANISM: Treponema denticola

<400> SEQUENCE: 72
cttggaaaag aatttataaa atgcgaagtt                               30

<210> SEQ ID NO 73
<211> LENGTH: 30
<212> TYPE: DNA
<213> ORGANISM: Treponema denticola

<400> SEQUENCE: 73
atgcgatata tctatgactt tacctattct                               30

<210> SEQ ID NO 74
<211> LENGTH: 30
<212> TYPE: DNA
<213> ORGANISM: Treponema denticola

<400> SEQUENCE: 74
aaactttgag gtactaaata aaacaagtca                               30

<210> SEQ ID NO 75
<211> LENGTH: 30
<212> TYPE: DNA
<213> ORGANISM: Treponema denticola

<400> SEQUENCE: 75
atatcttttg tcgttaaagt tagtaaaaaa                               30

<210> SEQ ID NO 76
<211> LENGTH: 30
<212> TYPE: DNA
<213> ORGANISM: Treponema denticola

<400> SEQUENCE: 76
tttgaaattc cccaaatgtc aattgttttc                               30

<210> SEQ ID NO 77
<211> LENGTH: 30
<212> TYPE: DNA
```

<213> ORGANISM: Treponema denticola

<400> SEQUENCE: 77
gaaaatgcag gcggttccac tggagaggtt                              30

<210> SEQ ID NO 78
<211> LENGTH: 30
<212> TYPE: DNA
<213> ORGANISM: Treponema denticola

<400> SEQUENCE: 78
taattcaaaa aaggtcttg gtttgaaagg                               30

<210> SEQ ID NO 79
<211> LENGTH: 30
<212> TYPE: DNA
<213> ORGANISM: Treponema denticola

<400> SEQUENCE: 79
agcccgccct gcggaattgc acggcccgtt                              30

<210> SEQ ID NO 80
<211> LENGTH: 30
<212> TYPE: DNA
<213> ORGANISM: Treponema denticola

<400> SEQUENCE: 80
attgagcgtc aagcacccgg taagcccacc                              30

<210> SEQ ID NO 81
<211> LENGTH: 30
<212> TYPE: DNA
<213> ORGANISM: Treponema denticola

<400> SEQUENCE: 81
ttggttattc gacttttgat ttgagctatc                              30

<210> SEQ ID NO 82
<211> LENGTH: 30
<212> TYPE: DNA
<213> ORGANISM: Treponema denticola

<400> SEQUENCE: 82
ctcgctcgag cacaacaggt ggctgtccac                              30

<210> SEQ ID NO 83
<211> LENGTH: 30
<212> TYPE: DNA
<213> ORGANISM: Treponema denticola

<400> SEQUENCE: 83
tttccagcta gagcatcaaa gtttataggg                              30

<210> SEQ ID NO 84
<211> LENGTH: 34
<212> TYPE: DNA
<213> ORGANISM: Treponema denticola

<400> SEQUENCE: 84
gtttgagagt tgtgtaattt aagatggagc aaac                         34

<210> SEQ ID NO 85
<211> LENGTH: 30

```
<212> TYPE: DNA
<213> ORGANISM: Treponema denticola

<400> SEQUENCE: 85
aatcagcagg taaatcaaag atgtgctgta                                    30

<210> SEQ ID NO 86
<211> LENGTH: 30
<212> TYPE: DNA
<213> ORGANISM: Treponema denticola

<400> SEQUENCE: 86
gataaaattg tgcttaaatt atagccactc                                    30

<210> SEQ ID NO 87
<211> LENGTH: 30
<212> TYPE: DNA
<213> ORGANISM: Treponema denticola

<400> SEQUENCE: 87
attaaaaaaa acagcggaat gacttgaacc                                    30

<210> SEQ ID NO 88
<211> LENGTH: 30
<212> TYPE: DNA
<213> ORGANISM: Treponema denticola

<400> SEQUENCE: 88
gatttgctgc gcgaggcttt ggataaggct                                    30

<210> SEQ ID NO 89
<211> LENGTH: 30
<212> TYPE: DNA
<213> ORGANISM: Treponema denticola

<400> SEQUENCE: 89
agttgctgcc tcgttaaaat ttccttttac                                    30

<210> SEQ ID NO 90
<211> LENGTH: 30
<212> TYPE: DNA
<213> ORGANISM: Treponema denticola

<400> SEQUENCE: 90
aggagctaat tgaacacctt atcactttac                                    30

<210> SEQ ID NO 91
<211> LENGTH: 30
<212> TYPE: DNA
<213> ORGANISM: Treponema denticola

<400> SEQUENCE: 91
ccaccgcgta gtggcgaacc gcgcctatat                                    30

<210> SEQ ID NO 92
<211> LENGTH: 30
<212> TYPE: DNA
<213> ORGANISM: Treponema denticola

<400> SEQUENCE: 92
atttccgtca agtacttttc ttcattttct                                    30

<210> SEQ ID NO 93
```

```
<211> LENGTH: 30
<212> TYPE: DNA
<213> ORGANISM: Treponema denticola

<400> SEQUENCE: 93
ttattaagtc tatctagagg agttaatatg                              30

<210> SEQ ID NO 94
<211> LENGTH: 30
<212> TYPE: DNA
<213> ORGANISM: Treponema denticola

<400> SEQUENCE: 94
tttcttctgc ttgtccatgt ccaaacctcc                              30

<210> SEQ ID NO 95
<211> LENGTH: 30
<212> TYPE: DNA
<213> ORGANISM: Treponema denticola

<400> SEQUENCE: 95
ttatcaacct taggaaatcc taactgatac                              30

<210> SEQ ID NO 96
<211> LENGTH: 30
<212> TYPE: DNA
<213> ORGANISM: Treponema denticola

<400> SEQUENCE: 96
acaaaggcta ttacaacaca ggcccttcaa                              30

<210> SEQ ID NO 97
<211> LENGTH: 30
<212> TYPE: DNA
<213> ORGANISM: Treponema denticola

<400> SEQUENCE: 97
ttaaaaagtt acactctagc gagatattgg                              30

<210> SEQ ID NO 98
<211> LENGTH: 30
<212> TYPE: DNA
<213> ORGANISM: Treponema denticola

<400> SEQUENCE: 98
tgagttttat cggtccaata aataagttgg                              30

<210> SEQ ID NO 99
<211> LENGTH: 30
<212> TYPE: DNA
<213> ORGANISM: Treponema denticola

<400> SEQUENCE: 99
gaaagctata cacaatcctc ttttgctcaa                              30

<210> SEQ ID NO 100
<211> LENGTH: 30
<212> TYPE: DNA
<213> ORGANISM: Treponema denticola

<400> SEQUENCE: 100
tagggcttca ccccttagaa accaccttaa                              30
```

```
<210> SEQ ID NO 101
<211> LENGTH: 30
<212> TYPE: DNA
<213> ORGANISM: Treponema denticola

<400> SEQUENCE: 101
gtcgtagcac ctttgataag tttgccacca                                    30

<210> SEQ ID NO 102
<211> LENGTH: 30
<212> TYPE: DNA
<213> ORGANISM: Treponema denticola

<400> SEQUENCE: 102
caacttgaca ttttgtcgga gacgattact                                    30

<210> SEQ ID NO 103
<211> LENGTH: 30
<212> TYPE: DNA
<213> ORGANISM: Treponema denticola

<400> SEQUENCE: 103
gctcaatttg aatatgaaaa gcagctccag                                    30

<210> SEQ ID NO 104
<211> LENGTH: 30
<212> TYPE: DNA
<213> ORGANISM: Treponema denticola

<400> SEQUENCE: 104
agataagcgg gcggttatct atgctggtct                                    30

<210> SEQ ID NO 105
<211> LENGTH: 30
<212> TYPE: DNA
<213> ORGANISM: Treponema denticola

<400> SEQUENCE: 105
ctaaggcttt ctctatgtca cgataccaaa                                    30

<210> SEQ ID NO 106
<211> LENGTH: 30
<212> TYPE: DNA
<213> ORGANISM: Treponema denticola

<400> SEQUENCE: 106
ctcttagttt gtagatgtcg tttaatatta                                    30

<210> SEQ ID NO 107
<211> LENGTH: 30
<212> TYPE: DNA
<213> ORGANISM: Treponema denticola

<400> SEQUENCE: 107
atcaaatctg tctaaaggag attttaaatg                                    30

<210> SEQ ID NO 108
<211> LENGTH: 30
<212> TYPE: DNA
<213> ORGANISM: Treponema denticola

<400> SEQUENCE: 108
tccaaatatt gttgcaaaat gacagcctga                                    30
```

```
<210> SEQ ID NO 109
<211> LENGTH: 30
<212> TYPE: DNA
<213> ORGANISM: Treponema denticola

<400> SEQUENCE: 109
taggaggtgt atacctctct aagcctctgt                                          30

<210> SEQ ID NO 110
<211> LENGTH: 30
<212> TYPE: DNA
<213> ORGANISM: Treponema denticola

<400> SEQUENCE: 110
agagaaatta ttgttctgga cttcgcactt                                          30

<210> SEQ ID NO 111
<211> LENGTH: 30
<212> TYPE: DNA
<213> ORGANISM: Treponema denticola

<400> SEQUENCE: 111
catagagatt ttgacttctt aaataaacag                                          30

<210> SEQ ID NO 112
<211> LENGTH: 30
<212> TYPE: DNA
<213> ORGANISM: Treponema denticola

<400> SEQUENCE: 112
ataagagtag cggcaccttt aaagcctttc                                          30

<210> SEQ ID NO 113
<211> LENGTH: 30
<212> TYPE: DNA
<213> ORGANISM: Treponema denticola

<400> SEQUENCE: 113
aaaaaattca ttttaaacct ccattagcca                                          30

<210> SEQ ID NO 114
<211> LENGTH: 30
<212> TYPE: DNA
<213> ORGANISM: Treponema denticola

<400> SEQUENCE: 114
ttacaccaaa attcttttta ataaaatcag                                          30

<210> SEQ ID NO 115
<211> LENGTH: 29
<212> TYPE: DNA
<213> ORGANISM: Treponema denticola

<400> SEQUENCE: 115
ttgaatcttt aattaagtct agacttgat                                           29

<210> SEQ ID NO 116
<211> LENGTH: 30
<212> TYPE: DNA
<213> ORGANISM: Treponema denticola

<400> SEQUENCE: 116
actttaccct gattttgggt tcggacttta                                          30
```

<210> SEQ ID NO 117
<211> LENGTH: 30
<212> TYPE: DNA
<213> ORGANISM: Treponema denticola

<400> SEQUENCE: 117
agcagaaagc ggagcggtag caagcgaaag            30

<210> SEQ ID NO 118
<211> LENGTH: 30
<212> TYPE: DNA
<213> ORGANISM: Treponema denticola

<400> SEQUENCE: 118
tttggcggag cgttaaaaaa agctcaactt            30

<210> SEQ ID NO 119
<211> LENGTH: 30
<212> TYPE: DNA
<213> ORGANISM: Treponema denticola

<400> SEQUENCE: 119
ttgaccacgt tgccgatagg gaagggccgt            30

<210> SEQ ID NO 120
<211> LENGTH: 30
<212> TYPE: DNA
<213> ORGANISM: Treponema denticola

<400> SEQUENCE: 120
ttaaatggtg cgactggctc cgagcttggt            30

<210> SEQ ID NO 121
<211> LENGTH: 30
<212> TYPE: DNA
<213> ORGANISM: Treponema denticola

<400> SEQUENCE: 121
ctcagattga ggattattta aaaatagatt            30

<210> SEQ ID NO 122
<211> LENGTH: 30
<212> TYPE: DNA
<213> ORGANISM: Treponema denticola

<400> SEQUENCE: 122
actttctcca tttcaacccg aatatcttca            30

<210> SEQ ID NO 123
<211> LENGTH: 30
<212> TYPE: DNA
<213> ORGANISM: Treponema denticola

<400> SEQUENCE: 123
ttcatctacg cctaagttag gaaaagagtt            30

<210> SEQ ID NO 124
<211> LENGTH: 30
<212> TYPE: DNA
<213> ORGANISM: Treponema denticola

<400> SEQUENCE: 124

```
cctaagccgg ggaaaagggc taagactgta                                30
```

<210> SEQ ID NO 125
<211> LENGTH: 30
<212> TYPE: DNA
<213> ORGANISM: Treponema denticola

<400> SEQUENCE: 125

```
tttaaactca gctgcaactt cgggagaggc                                30
```

<210> SEQ ID NO 126
<211> LENGTH: 30
<212> TYPE: DNA
<213> ORGANISM: Treponema denticola

<400> SEQUENCE: 126

```
tactaggtct gctgagtttt atgtggattt                                30
```

<210> SEQ ID NO 127
<211> LENGTH: 31
<212> TYPE: DNA
<213> ORGANISM: Treponema denticola

<400> SEQUENCE: 127

```
tcctcccatg ttttgttctt ccgaggttga g                              31
```

<210> SEQ ID NO 128
<211> LENGTH: 30
<212> TYPE: DNA
<213> ORGANISM: Treponema denticola

<400> SEQUENCE: 128

```
catagaacag attggcgtag acttgtttac                                30
```

<210> SEQ ID NO 129
<211> LENGTH: 30
<212> TYPE: DNA
<213> ORGANISM: Treponema denticola

<400> SEQUENCE: 129

```
tgaaaaattg ttattttgga cttcgcattt                                30
```

<210> SEQ ID NO 130
<211> LENGTH: 30
<212> TYPE: DNA
<213> ORGANISM: Treponema denticola

<400> SEQUENCE: 130

```
aagctcttct tgttgtcttc ttacttgttc                                30
```

<210> SEQ ID NO 131
<211> LENGTH: 30
<212> TYPE: DNA
<213> ORGANISM: Treponema denticola

<400> SEQUENCE: 131

```
attaaagcta agccttgtta ttgtttcttg                                30
```

<210> SEQ ID NO 132
<211> LENGTH: 30
<212> TYPE: DNA
<213> ORGANISM: Treponema denticola

<400> SEQUENCE: 132

```
accaaaattg gtggcgaatc gcgcctatat                              30

<210> SEQ ID NO 133
<211> LENGTH: 30
<212> TYPE: DNA
<213> ORGANISM: Treponema denticola

<400> SEQUENCE: 133
cgttctcttt ctgagatttg gtctttaagt                              30

<210> SEQ ID NO 134
<211> LENGTH: 13
<212> TYPE: DNA
<213> ORGANISM: Staphylococcus aureus
<220> FEATURE:
<221> NAME/KEY: modified_base
<222> LOCATION: (4)..(9)
<223> OTHER INFORMATION: a, c, t, g, unknown or other

<400> SEQUENCE: 134
acannnnnnr tgg                                                13

<210> SEQ ID NO 135
<211> LENGTH: 11
<212> TYPE: DNA
<213> ORGANISM: Staphylococcus aureus
<220> FEATURE:
<221> NAME/KEY: modified_base
<222> LOCATION: (4)..(8)
<223> OTHER INFORMATION: a, c, t, g, unknown or other

<400> SEQUENCE: 135
atcnnnnncc t                                                  11

<210> SEQ ID NO 136
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
atgagtattc aacatttccg tgtcgccctt attccctttt ttgcggcatt ttgccttcct     60
gttttTgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagagcgtt ttccaatgat gagcactttt aaagttctgc tatgtggcgc ggtattatcc   240
cgtgttgacg ccgggcaaga gcaactcggt cgccgcatac actattctca gaatgacttg   300
gttgagtact caccagtcac agaaaagcat cttacggatg gcatgacagt aagagaatta   360
tgcagtgctg ccataaccat gagtgataac actgcggcca acttacttct gacaacgatc   420
ggaggaccga aggagctaac cgcttttttg cacaacatgg gggatcatgt aactcgcctt   480
gatcgttggg aaccggagct gaatgaagcc ataccaaacg acgagcgtga ccaccacgatg   540 cctgtagcaa tggcaacaac gttgcgcaaa ctattaactg gcgaactact tactctagct   600
tcccggcaac aattaataga ctggatggag gcggataaag ttgcaggacc acttctgcgc   660
tcggcccttc cggctggctg gtttattgct gataaatctg gagccggtga gcgtgggtct   720
cgcggtatca ttgcagcact ggggccagat ggtaagccct cccgtatcgt agttatctac   780
acgacgggga gtcaggcaac tatggatgaa cgaaatagac agatcgctga gataggtgcc   840
```
tcactgatta agcattggta a 861

<210> SEQ ID NO 137
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

| | |
|---|---|
| atgagtattc aacatttccg tgtcgccctt attcccttt ttgcggcatt ttgccttcct | 60 |
| gtttttgctc acccagaaac gctggtgaaa gtaaaagatg ctgaagatca gttgggtgca | 120 |
| cgagtgggtt acatcgaact ggatctcaac agcggtaaga tccttgagag ttttcgcccc | 180 |
| gaagagcgtt ttccaatgat gagcactttt aaagttctgc tatgtggcgc ggtattatcc | 240 |
| cgtgttgacg ccgggcaaga gcaactcggt cgccgcatac actattctca gaatgacttg | 300 |
| gttgagtact caccagtcac agaaaagcat cttacggatg gcatgacagt aagagaatta | 360 |
| tgcagtgctg ccataaccat gagtgataac actgcggcca acttacttct gacaacgatc | 420 |
| ggaggaccga aggagctaac cgcttttttg cacaacatgg gggatcatgt aactcgcctt | 480 |
| gatcgttggg aaccggagct gaatgaagcc ataccaaacg acgagcgtga cactacgatg | 540 |
| ccagtagcaa tggcaacaac gttgcgcaaa ctattaactg gcgaactact tactctagct | 600 |
| tcccggcaac aattaataga ctggatggag gcggataaag ttgcaggacc acttctgcgc | 660 |
| tcggcccttc cggctggctg gtttattgct gataaatctg gagccggtga gcgtgggtct | 720 |
| cgcggtatca ttgcagcact ggggccagat ggtaagccct cccgtatcgt agttatctac | 780 |
| acgacgggga gtcaggcaac tatggatgaa cgaaatagac agatcgctga gataggtgcc | 840 |
| tcactgatta agcattggta a | 861 |

<210> SEQ ID NO 138
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

-continued

```
Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
            165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
            245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```